United States Patent
Robl et al.

(10) Patent No.: US 6,927,227 B2
(45) Date of Patent: Aug. 9, 2005

(54) HETEROCYCLIC CONTAINING BIPHENYL AP2 INHIBITORS AND METHOD

(75) Inventors: Jeffrey A. Robl, Newtown, PA (US); David R. Magnin, Hamilton, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 10/321,137

(22) Filed: Dec. 17, 2002

(65) Prior Publication Data

US 2003/0199563 A1 Oct. 23, 2003

Related U.S. Application Data

(62) Division of application No. 09/519,079, filed on Mar. 6, 2000, now Pat. No. 6,548,529.
(60) Provisional application No. 60/127,745, filed on Apr. 5, 1999.

(51) Int. Cl.[7] .................. A61K 31/421; A61K 31/426; C07D 277/20; C07D 263/30; C07D 233/54
(52) U.S. Cl. ............... 514/365; 548/203; 548/235; 548/252; 548/314.7; 548/341.1; 514/374; 514/399
(58) Field of Search ................. 548/252, 341.1, 548/314.7, 203, 235; 514/399, 365, 374

(56) References Cited

U.S. PATENT DOCUMENTS 5,348,969 A * 9/1994 Romine et al. ............. 514/376

OTHER PUBLICATIONS

Krasovitskii et al (1985): STN International, CAPLUS Database (Columbus, Ohio), document No. 103:71231.*

Krasovitskii, B.M. et al., "Sterically Hindered Mono– and Bis(2,5–Diaryloxazoles) Containing Biphenyl Systems", Chemistry of Heterocyclic Compounds, vol. 21, pp. 149–153 (1985) (English translation of Khimiya Geterotsiklicheskikh Soedinenii, No. 2, pp. 184–188, Feb., 1985).

Schlögl, K. et al., "Optisch aktive Tricarbonylchrom–Komplexe der Diphensäure und ihrer Derivate—Enantiomerenreinheit, Circulardichroismus und absolute Konfiguration", Liebigs Ann. Chem., vol. 11, pp. 1877–1888 (1980).

* cited by examiner

Primary Examiner—Golam M M Shameem
(74) Attorney, Agent, or Firm—Laureles A. Duncan; Joseph C. Wang

(57) ABSTRACT aP2 inhibiting compounds are provided having the formula

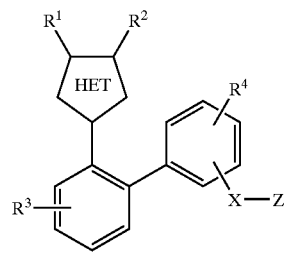

wherein $R^1$, $R^2$, $R^3$, $R^4$, X—Z and

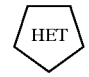

are as described herein.

A method is also provided for treating diabetes and related diseases, especially Type II diabetes, employing such aP2 inhibitor or a combination of such aP2 inhibitor and another antidiabetic agent such as metformin, glyburide, troglitazone and/or insulin.

12 Claims, No Drawings

HETEROCYCLIC CONTAINING BIPHENYL AP2 INHIBITORS AND METHOD

This application is a divisional application of Ser. No. 09/519,079 filed on Mar. 6, 2000, which issued as U.S. Pat. No. 6,548,529 B1 on Apr. 15, 2003, which is based on a provisional application having U.S. Ser. No. 60/127,745 filed on Apr. 5, 1999.

FIELD OF THE INVENTION

The present invention relates to heterocyclic containing biphenyls which are inhibitors of aP2 and to a method for treating diabetes, especially Type II diabetes, as well as hyperglycemia, hyperinsulinemia, obesity, Syndrome X, diabetic complications, atherosclerosis and related diseases, and other chronic inflammatory and autoimmune/inflammatory diseases, employing such heterocyclic containing biphenyls alone or in combination with one or more types of antidiabetic agents.

BACKGROUND OF THE INVENTION

Fatty acid binding proteins (FABPs) are small cytoplasmic proteins which bind to fatty acids such as oleic acids which are important metabolic fuels and cellular regulators. Dysregulation of fatty acid metabolism in adipose tissue is a prominent feature of insulin resistance and the transition from obesity to non-insulin dependent diabetes mellitus (NIDDM or Type II diabetes).

aP2 (adipocyte fatty binding protein), an abundant 14.6 KDa cytosolic protein in adipocytes, and one of a family of homologous intracellular fatty acid binding proteins (FABPs), is involved in the regulation of fatty acid trafficking in adipocytes and mediates fatty acid fluxes in adipose tissue. G. S. Hotamisligil et al, "Uncoupling of Obesity from Insulin Resistance Through a Targeted Mutation in aP2, the Adipocyte Fatty Acid Binding Protein", Science, Vol. 274, Nov. 22, 1996, pp. 1377–1379, report that aP2-deficient mice placed on a high fat diet for several weeks developed dietary obesity, but, unlike control-mice on a similar diet, did not develop insulin resistance or diabetes. Hotamisligil et al conclude that "aP2 is central to the pathway that links obesity to insulin resistance" (Abstract, page 1377).

DIALOG ALERT DBDR928 dated Jan. 2, 1997, Pharmaprojects No. 5149 (Knight-Ridder Information) discloses that a major drug company "is using virtual screening techniques to identify potential new antidiabetic compounds." It is reported that "the company is screening using aP2, a protein related to adipocyte fatty acid binding protein."

U.S. application Ser. No. 60/100,677, filed Sep. 17, 1998 (attorney file LA24*) discloses a method for treating diabetes employing an aP2 inhibitor.

DESCRIPTON OF THE INVENTION

In accordance with the present invention, heterocyclic containing biphenyl compounds are provided which have the structure

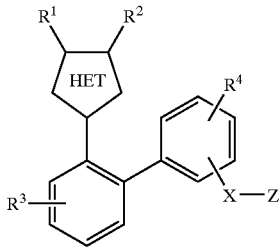

I where
R$^1$ and R$^2$ are the same or different and are independently selected from H, alkyl, cycloalkyl, cycloalkenyl, aryl, heteroaryl, heteroarylalkyl, aralkyl, cycloheteroalkyl and cycloheteroalkylalkyl;

R$^3$ is selected from hydrogen, halogen, alkyl, alkenyl, alkynyl, alkoxy, cycloalkyl, cycloalkylalkyl, cycloalkenyl, alkylcarbonyl, cycloheteroalkyl, cycloheteroalkylalkyl, cycloalkenylalkyl, haloalkyl, polyhaloalkyl, cyano, nitro, hydroxy, amino, alkanoyl, alkylthio, alkylsulfonyl, alkoxycarbonyl, alkylaminocarbonyl, alkylcarbonylamino, alkylcarbonyloxy, alkylaminosulfonyl, alkylamino, dialkylamino, all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, alkoxycarbonylamino, alkylsulfonyl, aminosulfinyl, aminosulfonyl, alkylsulfinyl, sulfonamido or sulfonyl;

R$^4$ is selected from hydrogen, halogen, alkyl, alkenyl, alkynyl, alkoxy, aryl, heteroaryl, arylalkyl, heteroarylalkyl, arylalkenyl, arylalkynyl, cycloalkyl, cycloalkylalkyl, polycycloalkyl, polycycloalkylalkyl, cycloalkenyl, cycloalkynyl, alkylcarbonyl, arylcarbonyl, cycloheteroalkyl, cycloheteroalkylalkyl, cycloalkenylalkyl, polycycloalkenyl, polycycloalkenylalkyl, polycycloalkynyl, polycycloalkynylalkyl, haloalkyl, polyhaloalkyl, cyano, nitro, hydroxy, amino, alkanoyl, aroyl, alkylthio, alkylsulfonyl, arylsulfonyl, alkoxycarbonyl, aryloxycarbonyl, alkylaminocarbonyl, arylaminocarbonyl, alkylcarbonylamino, alkylcarbonyloxy, alkylaminosulfonyl, arylaminosulfonyl, alkylamino, dialkylamino, all optionally substituted through available carbon atoms with 1, 2, 3, 4 or 5 groups selected from hydrogen, halo, alkyl, haloalkyl, polyhaloalkyl, alkoxy, haloalkoxy, polyhaloalkoxy, alkoxycarbonyl, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, hydroxyalkyl, nitro, cyano, amino, substituted amino, alkylamino, dialkylamino, thiol, alkylthio, arylthio, heteroarylthio, arylthioalkyl, alkylcarbonyl, arylcarbonyl, acyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, alkoxycarbonylamino, arylsulfinyl, arylsulfinylalkyl, arylsulfonyl, alkylsulfonyl, aminosulfinyl, aminosulfonyl, arylsulfonylamino, heteroarylcarbonylamino, heteroarylsulfinyl, heteroarylthio, heteroarylsulfonyl, alkylsulfinyl, sulfonamido or sulfonyl;

X is a bond or a linker group selected from $(CH_2)_n$, $O(CH_2)_n$, $S(CH_2)_n$, NHCO, CH=CH, cycloalkylene or $N(R^5)$ $(CH_2)_n$, (where n=0–5 and $R^5$ is H, alkyl, or alkanoyl);

Z is $CO_2H$ or tetrazole of the formula

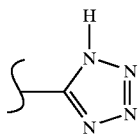

or its tautomer; and the group

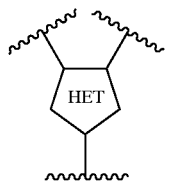

represents a heterocyclic group (including heteroaryl and cycloheteroalkyl groups) preferably containing 5-members within the ring and containing preferably 1–3 heteroatoms within the ring, and which may further optionally include one or two substituents which are alkyl, alkenyl, hydroxyalkyl, keto, carboxyalkyl, carboxy, cycloalkyl, alkoxy, formyl, alkanoyl, alkoxyalkyl or alkoxycarboxyl;

with the provisos that (1) n≠o when Z is $CO_2H$ and X is $O(CH_2)_n$, $S(CH_2)_n$ or $N(R^5)$ $(CH_2)_n$); and
(2) when

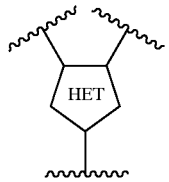

is

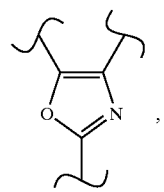

then X—Z may not be O-lower alkylene-$CO_2H$ or —O-lower alkylene-$CO_2$alkyl when $R^1$ and $R^2$ are both aryl or substituted aryl and $R^3$ and $R^4$ are each hydrogen;

and including pharmaceutically acceptable salts thereof, and prodrug esters thereof, and all stereoisomers thereof.

In addition, in accordance with the present invention, a method is provided for treating diabetes, especially Type II diabetes, and related diseases such as insulin resistance, hyperglycemia, hyperinsulinemia, elevated blood levels of fatty acids or glycerol, obesity, hypertriglyceridemia, Syndrome X, diabetic complications, atherosclerosis and other chronic inflammatory and autoimmune/inflammatory diseases, wherein a therapeutically effective amount of a compound of structure I (which inhibits aP2) is administered to a human patient in need of treatment.

The term "chronic inflammatory and autoimmune/inflammatory diseases" referred to above includes inflammatory bowel diseases, such as Crohn's disease and ulcerative colitis, rheumatoid arthritis, chronic obstructive pulmonary disease, emphysema, systemic lupus erythematosis, and other disease states involving tissue injury-, necrosis-, and/or infection-induced imbalanced inflammation associated with macrophage and leukocyte over-stimulation and excessive or dysregulated release of cellular mediators.

In addition, in accordance with the present invention, a method is provided for treating chronic and autoimmune/inflammatory diseases including inflammatory bowel diseases such as Crohn's disease and ulcerative colitis, rheumatoid arthritis, chronic obstructive pulmonary disease, emphysema, systemic lupus erythematosis, and other disease states involving tissue injury-, necrosis-, and/or infection-induced imbalanced inflammation associated with macrophage and leukocyte over-stimulation and excessive or dysregulated release of cellular mediators, wherein a therapeutically effective amount of an aP2 inhibitor is administered to a human patient in need of treatment.

In addition to compounds of formula I, other aP2 inhibitors useful in carrying out the above method for treating chronic inflammatory and autoimmune/inflammatory diseases are disclosed in U.S. application Ser. No. 09/390,275, filed Sep. 7, 1999 (file LA24a), which is incorporated herein by reference.

The conditions, diseases, and maladies collectively referred to as "Syndrome X" (also known as Metabolic Syndrome) are detailed in Johannsson *J. Clin. Endocrinol. Metab.*, 82, 727–34 (1997).

The conditions, diseases and maladies collectively referred to as "diabetic complications" include retinopathy, neuopathy and nephropathy, and other known complications of diabetes.

In addition, in accordance with the present invention, a method is provided for treating diabetes and related diseases as defined above and hereinafter, as well as obesity, hypertriglyceridemia, Syndrome X, diabetic complications and other chronic inflammatory and autoimmune/inflammatory diseases, wherein a therapeutically effective amount of a combination of a compound of structure 1 and 1, 2, 3 or more other types of therapeutic agents is administered to a human patient in need of treatment.

The term "other type of therapeutic agents" as employed herein refers to one or more antidiabetic agents (other than aP2 inhibitors of formula I), one or more anti-obesity agents, one or more lipid-lowering agents (including anti-atherosclerosis agents), one or more anti-hypertensive agents, one or more anti-platelet agents, and/or one or more anti-infective agents.

In the above method of the invention, the compound of structure I will be employed in a weight ratio to the other type of therapeutic agent (depending upon its mode of operation) within the range from about 0.01:1 to about 500:1, preferably from about 0.1:1 to about 100:1.

Examples of the group

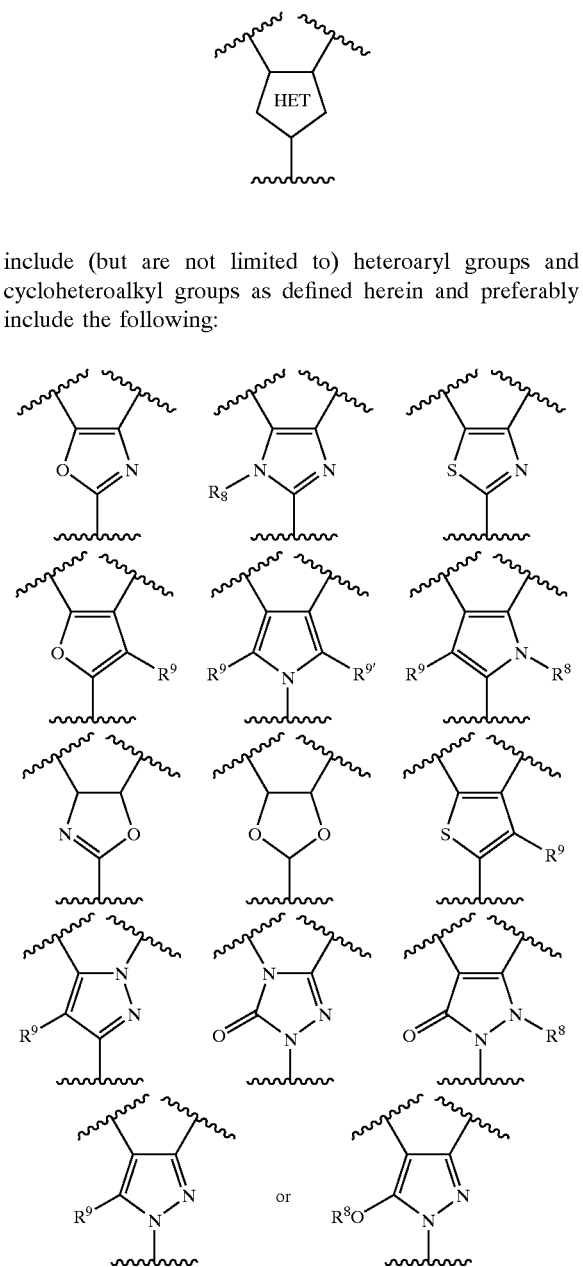

include (but are not limited to) heteroaryl groups and cycloheteroalkyl groups as defined herein and preferably include the following:

where $R^8$ is selected from H, alkyl, haloalkyl, hydroxyalkyl, alkoxyalkyl, or alkenyl, and $R^9$ and $R^{9'}$ are the same or different and are selected independently from H, alkyl, alkoxy, alkenyl, formyl, $CO_2H$, $CO_2$(lower alkyl), hydroxyalkyl, alkoxyalkyl, CO(alkyl), carboxylalkyl, haloalkyl, alkenyl or cycloalkyl.

With respect to the $R^8$, $R^9$ and $R^{9'}$ groups, alkyl by itself or as part of another group will preferably contain 1 to 6 carbons.

Examples of X—Z moieties include (but are not limited to)

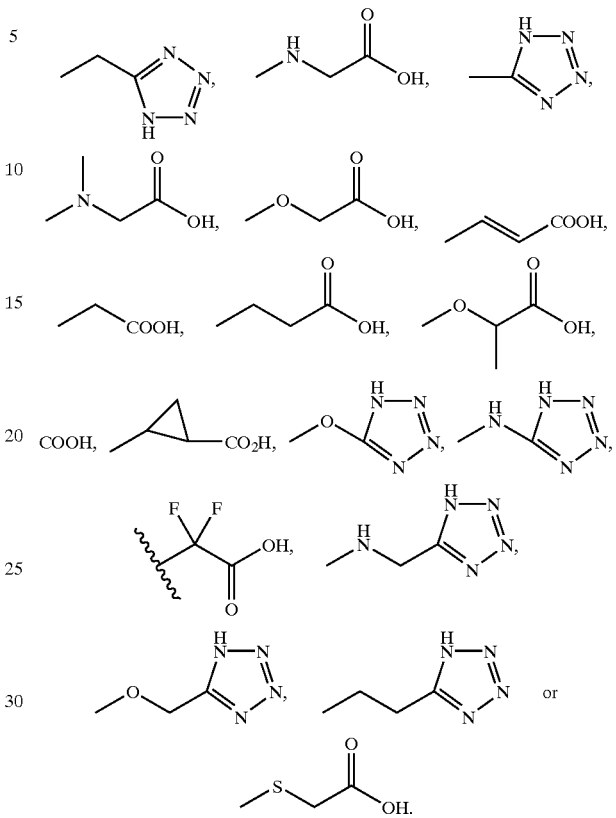

Preferred are compounds of formula I where

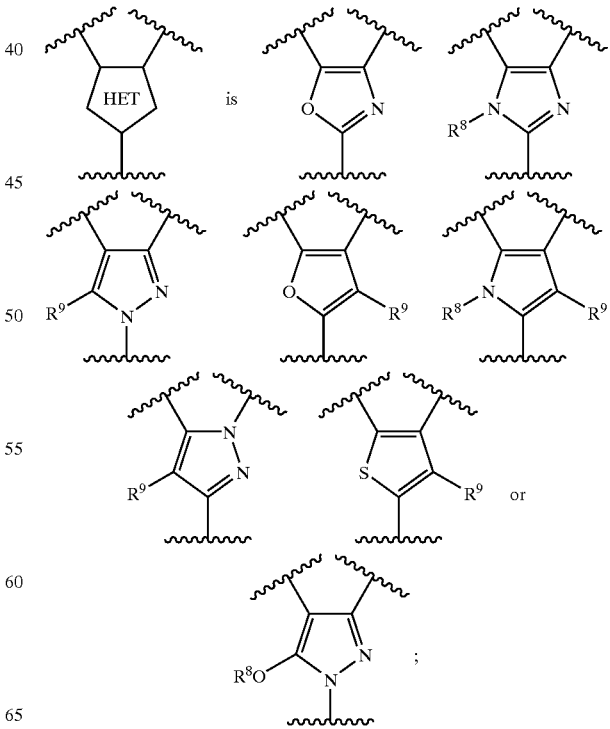

(where $R^8$ is hydrogen, alkyl, fluoroalkyl or alkoxyalkyl, and where $R^9$ is hydrogen, alkyl, fluoroalkyl, alkoxy or hydroxyalkyl).

$R^1$ and $R^2$ are each phenyl, substituted phenyl or cycloalkyl; $R^3$ and $R^4$ are the same or different are independently selected from H, halo, alkyl or alkoxy; X is $OCH_2$, $NHCH_2$, $CH_2$ or $CH_2CH_2$; and Z is $CO_2H$ or tetrazole.

More preferred are compounds of formula I where

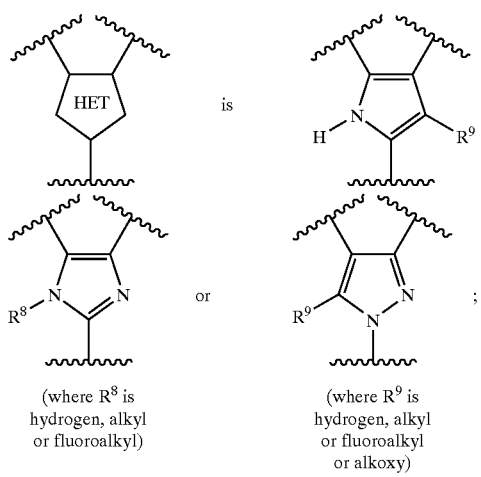

(where $R^8$ is hydrogen, alkyl or fluoroalkyl)

(where $R^9$ is hydrogen, alkyl or fluoroalkyl or alkoxy)

$R^1$ and $R^2$ are each phenyl; $R^3$ and $R^4$ are each H; X is $OCH_2$, $CH_2$ or $NHCH_2$; and Z is $CO_2H$ or tetrazole.

DETAILED DESCRIPTION OF THE INVENTION

Compounds of the invention of general structure I may be synthesized from intermediate II as shown in the schemes set out below. The groups $R^1$, $R^2$, $R^3$, and $R^4$, in intermediate II, are the same as described above with respect to the formula I compounds of the invention while A is a precursor to X—Z and is detailed below.

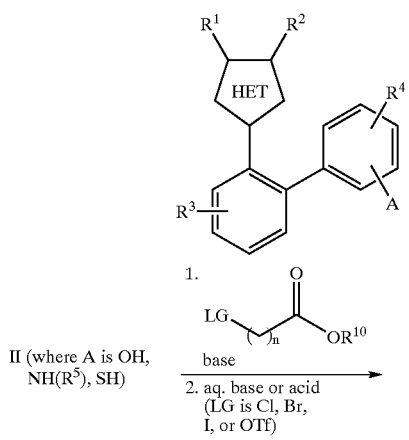

II (where A is OH, NH($R^5$), SH)

1. 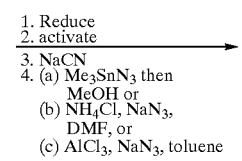
base
2. aq. base or acid
(LG is Cl, Br, I, or OTf)

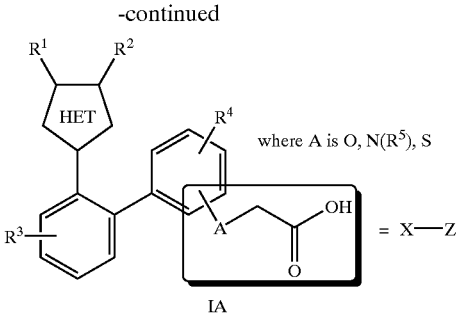

IA

II (where A is OH, NH($R^5$), SH)

1. 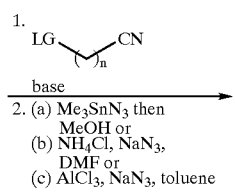
base
2. (a) $Me_3SnN_3$ then MeOH or
(b) $NH_4Cl$, $NaN_3$, DMF or
(c) $AlCl_3$, $NaN_3$, toluene

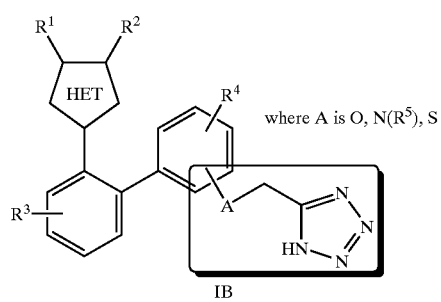

IB

II (where A is OH, SH)

1. BrCN
2. $NH_4Cl$, $NaN_3$, DMF

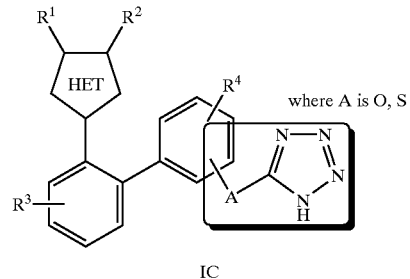

IC

II (where A is CHO) → Oxidize →

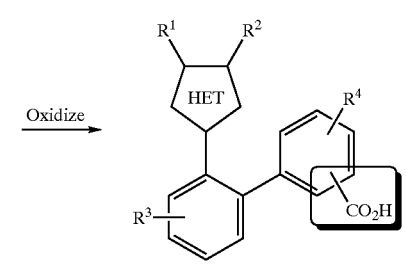

ID

II (where A is CHO)
1. Reduce
2. activate
3. NaCN
4. (a) $Me_3SnN_3$ then MeOH or
(b) $NH_4Cl$, $NaN_3$, DMF, or
(c) $AlCl_3$, $NaN_3$, toluene I, or OTf and E may be CHO, CN, $CO_2R^{10}$, OH, $N(R^5)H$, $NO_2$, $SR^{10}$, $OR^{10}$, $OSi(R^{10})_3$, or preferably X—Z or a protected variant thereof and where $R^{11}$ is $CO_2R^{10}$, CHO, CN, —NH—N=C($R^2$)(CH$_2R^1$), $NH_2$, or —CONH—N=CH($R^2$)

with the proviso that when W or G is ZnBr or ZnCl, E or $R^{11}$ may not be a reactive group such as CHO.

Compound V, depicted below where Y is

[structure]

can be utilized to make heterocycles of the type VIA–VIN by standard methods described in the literature, for example, as shown below.

where $R^{10}$ is lower alkyl or benzyl.

The biphenyl portion of the molecule may be prepared by reaction of compound III with substituted aryl IV via Stille or Suzuki type coupling to give compounds of the type V.

where W is $B(OH)_2$, $SnBu_3$, or ZnBr or ZnCl and G is Cl, Br, I, or OTf or G is $B(OH)_2$ or $SnBu_3$ and W is Cl, Br,

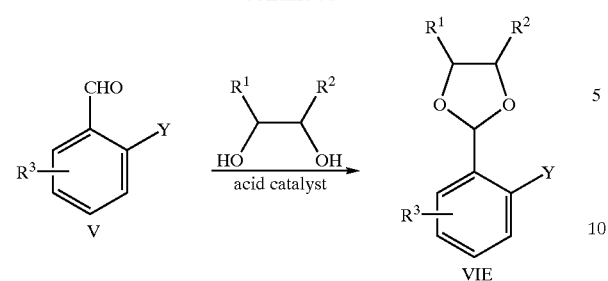
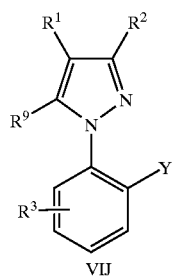
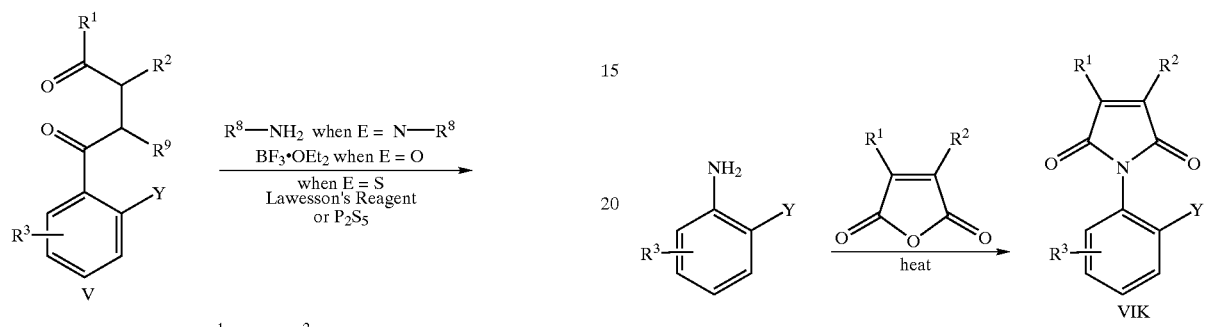
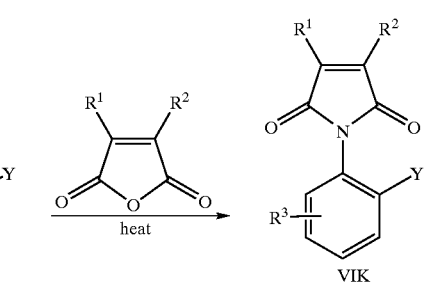
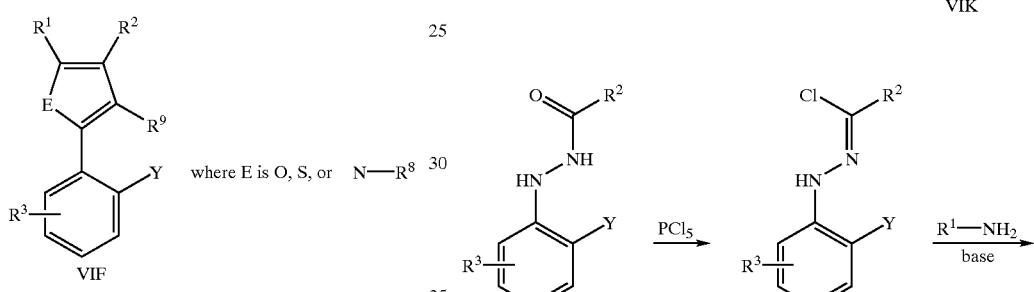
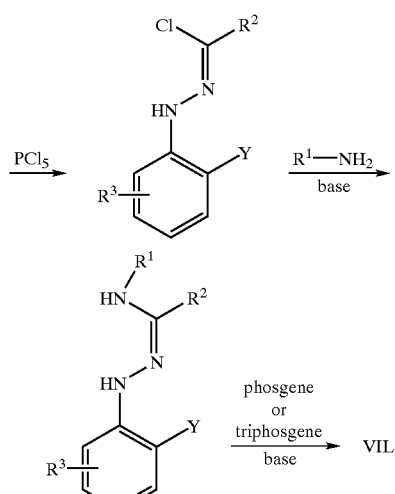
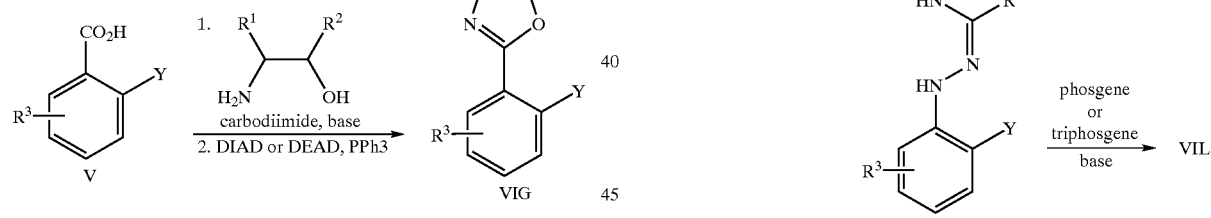
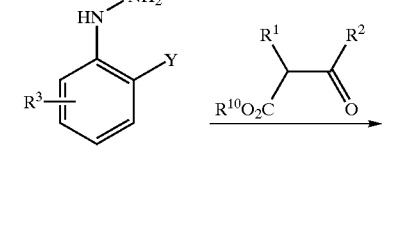
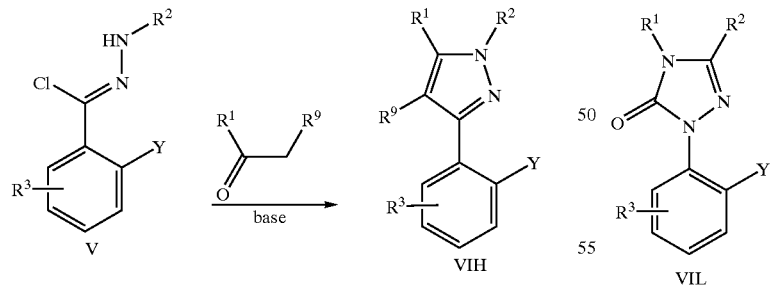
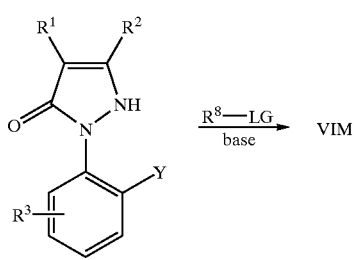
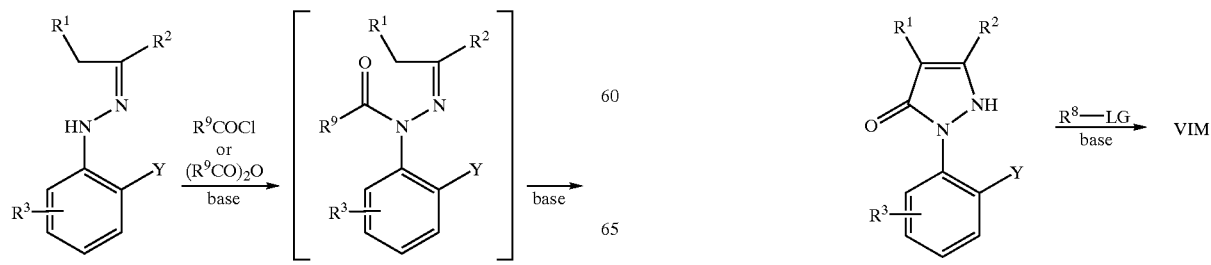

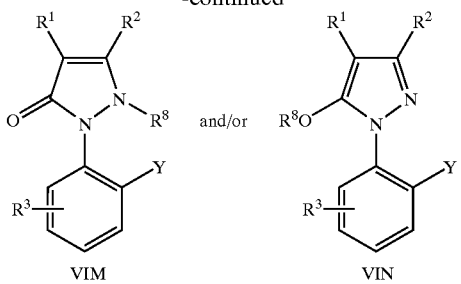

Alternately, and in some cases more preferably, compounds of the type VII may be converted to the desired heterocycles by these aforementioned methodologies and subsequently converted to compounds of type II via biphenyl coupling reactions.

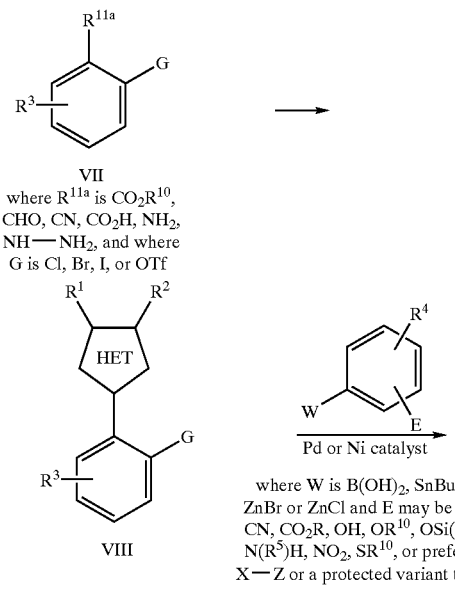

with the proviso that when W is ZnCl or ZnBr, E cannot be a reactive group such as CHO.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio and/or any of the $R^3$ groups or substituents for $R^3$.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

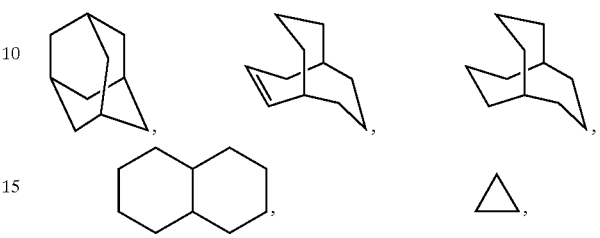

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the $R^4$ groups or substituents for $R^4$.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the $R^3$ groups, or the $R^3$ substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the $R^3$ groups, or the $R^3$ substituents set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_n$ or $(CH_2)_p$ (where, p is 1 to 8, preferably 1 to 5, and n is 1 to 5, preferably 1 to 3, which includes alkylene, alkenylene or alkynylene groups) as defined herein, may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino or alkylcarbonyloxy.

Examples of $(CH_2)_n$ or $(CH_2)_p$, alkylene, alkenylene and alkynylene include

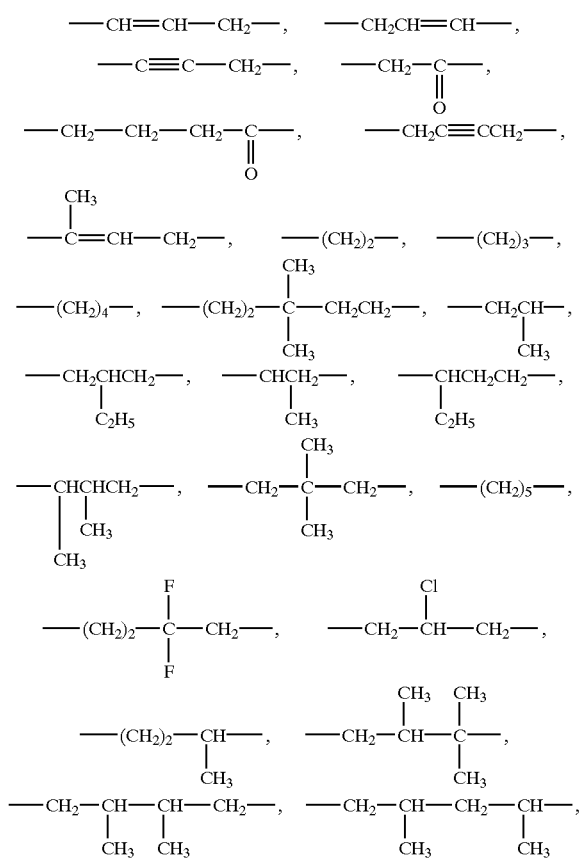

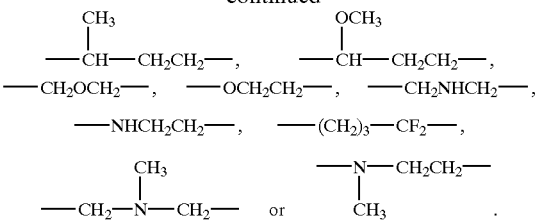

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

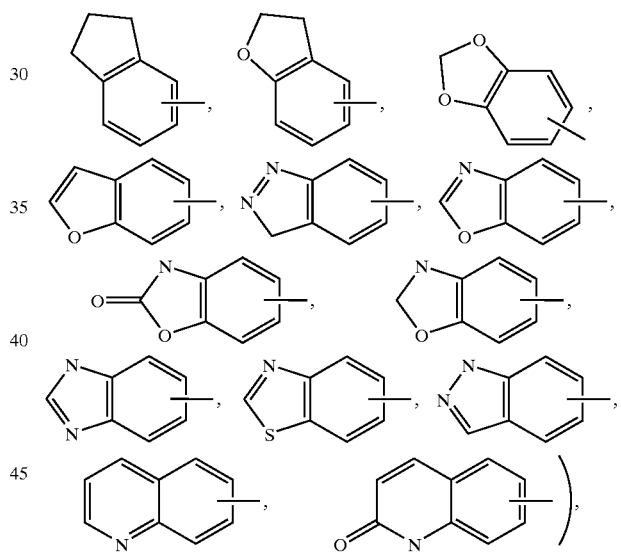

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfon-aminocarbonyl and/or any of the $R^4$ groups or the $R^4$ substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the $R^4$ groups or $R^4$ substituents thereof as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the $R^3$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

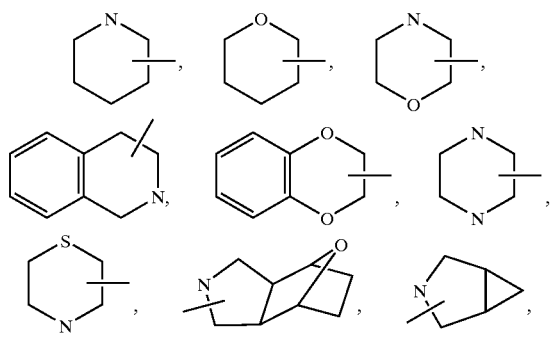

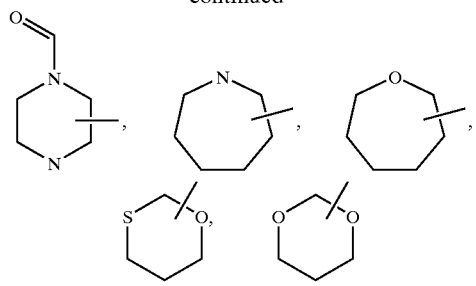

and the like. The above groups may include 1 to 4 substituents such as alkyl, halo, oxo and/or any of of the $R^4$ groups, or the $R^4$ substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the $R^4$ groups or the $R^4$ substituents set out above. Examples of heteroaryl groups include the following:

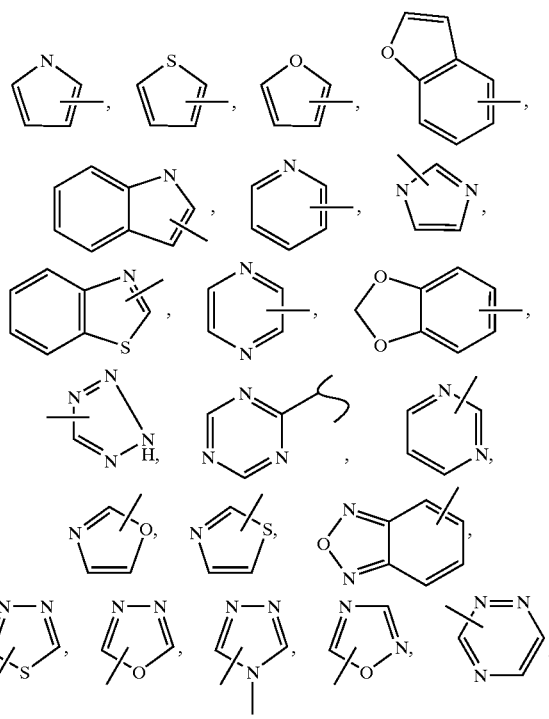

and the like.

The term "cycloheteroalkylalkyl" as used herein alone or as part of another gorup refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for carboxylic acids such as similar carboxylic acid esters such as methyl, ethyl benzyl and the like. Other examples include the following groups: (1-alkanoyloxy)alkyl such as,

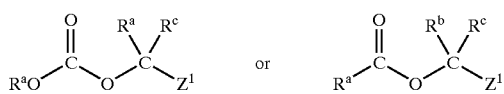

wherein $R^a$, $R^b$ and $R^c$ are H, alkyl, aryl or aryl-alkyl; however $R^aO$ cannot be HO, and where $Z^1$ is

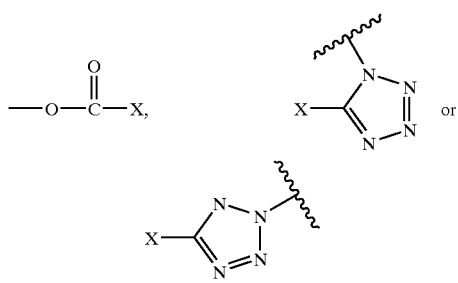

(where X is previously defined).
Examples of such prodrug esters include
$CH_3CO_2CH_2$—

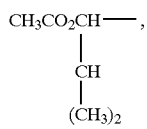

$t\text{-}C_4H_9CO_2CH_2$—, or

Other examples of suitable prodrug esters include

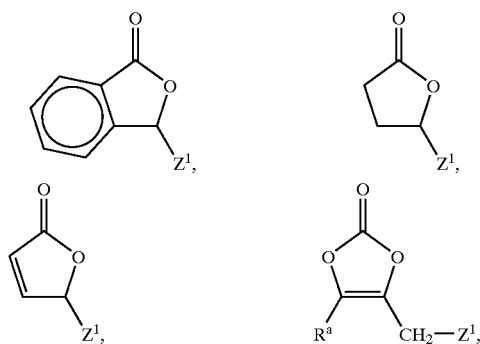

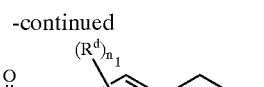

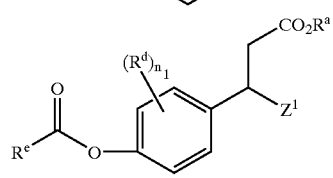

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Where the compounds of structure I are in acid form it may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, ethylenediamine, t-butylamine, t-octylamine, dehydroabietylamine.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compounds of structure I may be used in combination with one or more other types of therapeutic agents which may be administered orally in the same dosage form, in a separate oral dosage form or by injection.

The other type of therapeutic agent which may be optionally employed in combination with the aP2 inhibitor of formula I may be 1,2,3 or more antidiabetic agents or antihyperglycemic agents including insulin secretagogues or insulin sensitizers, or other antidiabetic agents preferably having a mechanism of action different from aP2 inhibition and may include biguamides, sulfonyl ureas, glucosidase inhibitors, PPAR γ agonists, such as thiazolidinediones, SGLT2 inhibitors, PPAR α/γ dual agonists, dipeptidyl peptidase IV (DP4) inhibitors, and/or meglitinides, as well as insulin, and/or glucagon-like peptide-1 (GLP-1).

It is believed that the use of the compounds of structure I in combination with 1, 2, 3 or more other antidiabetic agents produces antihyperglycemic results greater than that possible from each of these medicaments alone and greater than the combined additive anti-hyperglycemic effects produced by these medicaments.

The other antidiabetic agent may be an oral antihyperglycemic agent preferably a biguamide such as metformin or phenformin or salts thereof, preferably metformin HCl.

Where the other antidiabetic agent is a biguamide, the compounds of structure I will be employed in a weight ratio to biguamide within the range from about 0.01:1 to about 100:1, preferably from about 0.1:1 to about 5:1.

The other antidiabetic agent may also preferably be a sulfonyl urea such as glyburide (also known as glibenclamide), glimepiride (disclosed in U.S. Pat. No.

4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.5:1 to about 50:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.2:1 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1–36) amide, GLP-1(7–36) amide, GLP-1(7–37) (as disclosed in U.S. Pat. No. 5,614,492 to Habener, the disclosure of which is incorporated herein by reference), as well as AC2993 (Amylen) and LY-315902 (Lilly), which may be administered via injection, intranasal, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. provisional application No. 60/155,400, filed Sep. 22, 1999, (attorney file LA29) the disclosure of which is incorporated herein by reference, employing dosages as set out therein, which compounds designated as preferred are preferred for use herein.

The other antidiabetic agent may be an SGLT2 inhibitor such as disclosed in U.S. provisional application No. 60/158,773, filed Oct. 12, 1999 (attorney file LA49), employing dosages as set out herein. Preferred are the compounds designated as preferred in the above application.

The other antidiabetic agent may be a DP4 inhibitor such as disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The aP2 inhibitor of formula I will be employed in a weight ratio to the meglitinide, PPAR γ agonist, PPAR α/γ dual agonist, SGLT2 inhibitor or DP4 inhibitor within the range from about 0.01:1 to about 100:1, preferably from about 0.2:1 to about 10:1.

The hypolipidemic agent or lipid-lowering agent which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-Trifluoroethoxy)benzoyl]amino]-1-piperidinyl] butyl]-N-(2,2,2-trifluoroethyl)-9H-fluorene-9-carboxamide

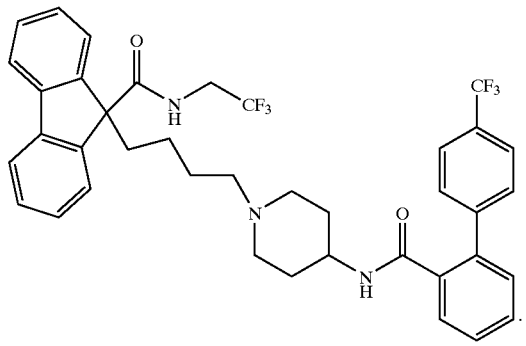

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, atavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. No. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. No. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

Preferred hypolipidemic agents are pravastatin, lovastatin, simvastatin, atorvastatin, fluvastatin, cerivastatin, atavastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties, Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin.

The other type of therapeutic agent which may be optionally employed with the aP2 inhibitor of formula I may be 1, 2, 3 or more of an anti-obesity agent including a beta 3 adrenergic agonist, a lipase inhibitor, a serotonin (and dopamine) reuptake inhibitor, a thyroid receptor beta drug and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor beta compound which may be optionally employed in combination with a compound of formula I may be a thyroid receptor ligand as disclosed in WO97/21993 (U. Cal SF), WO99/00353 (KaroBio) and GB98/284425 (KaroBio), with compounds of the KaroBio applications being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The other type of therapeutic agent which may be optionally employed with the aP2 inhibitor of formula I may be 1, 2, 3 or more of an antihypertensive agent including an ACE inhibitor, a vasopeptidase inhibitor, an angiotensin II antagonist, a calcium channel blocker, a potassium channel opener, an alpha-blocker, a beta blocker, a centrally acting alpha agonist, and/or a diuretic.

The ACE inhibitor which may be optionally employed in combination with a compound of formula I may be lisinopril, enalapril, quinapril, benazepril, fosinopril, fentiapril, ramipril, captopril, enalaprilat, moexipril, tranolapril, perindopril, ceranopril, zofenopril or cetapril.

Preferred ACE inhibitors are captopril, as well as fosinopril, enalapril, lisinopril, quinapril, benazepril, fentiapril, ramipril, and moexipril.

The vasopeptidase inhibitor (also known as NEP/ACE inhibitors) which may be optionally employed with the aP2 inhibitor of formula I may be omapatrilat (most preferred) and [S-(R*,R*)]-hexahydro-6-[(2-mercapto-1-oxo-3-phenylpropyl)amino]-2,2-dimethyl-7-oxo-1H-azepine-1-acetic acid (BMS 189,921 also preferred), as well as those disclosed in U.S. Pat. Nos. 5,362,727, 5,366,973, 5,225,401, 4,722,810, 5,223,516, 4,749,688. U.S. Pat. No. 5,504,080, U.S. Pat. No. 5,552,397, U.S. Pat. No. 5,612,359, U.S. Pat. No. 5,525,723, European Patent Application 0599,444, 0481,522, 0599,444, 0595,610, European Patent Application 0534363.A2, 534,396 and 534,492, and European Patent Application 0629627.A2.

Preferred are those NEP/ACE inhibitors which are designated as preferred in the above patents/applications which U.S. patents/applications are incorporated herein by reference.

The angiotensin II receptor antagonist (also referred to herein as angiotensin II antagonist or AII antagonist) which may be optionally employed in combination with a compound of formula I may be irbesartan, losartan, valsartan, candesartan, telmisartan, tasosartan and/or eprosartan, with irbesartan or losartan being preferred.

The calcium channel blocker (also referred to as a calcium antagonist) which may be optionally employed in combination with a compound of formula I may be amlodipine, diltiazem, nifedipine, verapamil, feldodipine, nisoldipine, isradipine and/or nicardipine, with amlodipine, diltiazem, verapamil and nifedipine being preferred.

The alpha-blocker which may be optionally employed in combination with a compound of formula I may be terazosin, doxazosin or prazosin, all of which are preferred.

The beta-blocker which may be optionally employed in combination with a compound of formula I may be nadolol, atenolol, propranolol, metoprolol, carvediol or sotalol, with atenolol and nadolol being preferred.

The potassium channel opener which may be optionally employed in combination with a compound of formula I may be minoxidil.

The centrally acting α agonist antihypertensive agent which may be optionally employed in combination with a compound of formula I may be clonidine or guanfacine, with clonidine being preferred.

The diuretic which may be optionally employed in connection with a compound of formula I may be hydrochlorothiazide, torasemide, furosemide, spironolactone and/or indapamide, with hydrochlorothiazide and furosemide being preferred.

The antiplatelet agent (also known as platelet aggregation inhibitor) which may be optionally employed in combination with a compound of formula I may be aspirin, clopidogrel, ticlopidine, dipyridamole, abciximab, tirofiban, eptifibatide, anagrelide and/or ifetroban, with aspirin and clopidogrel being preferred.

The anti-infective agent which may be optionally employed in combination with a compound of formula I may be an anti-infective that is effective against chlamydial infections, such as azithromycin, gatifloxacin, ciprofloxacin, levofloxacin and trovafloxacin, with azithromycin and gatifloxacin being preferred.

The various antihypertensive agents and antiplatelet agents and anti-infective agents described above may be employed in the same dosage form with the compound of formula I or in different dosage forms, in dosages and regimens as generally known in the art or in the PDR.

In carrying our the method of the invention, a pharmaceutical composition will be employed containing the compounds of structure I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 20 and 2,000 mg per day, which can be administered in a single dose or in the form of individual doses from 1–4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

aP2 inhibitor activity of the compounds of the invention may be determined by use of an in vitro assay system which measures the potentiation of inhibition of aP2 by displacement of a fluorescent substrate from aP2 by the inhibitor. Inhibition constants (Ki values) for the aP2 inhibitors of the invention may be determined by the method described below:

Production of Purified Recombinant Human aP2 Protein. Recombinant human aP2 protein is produced by standard recombinant DNA technology. In the typical case, aP2 is produced by heterologous expression in $E.\ coli$ strain BL21 (D53) transformed with pET11a vector containing the full length human aP2 cDNA (Baxa, C. A., Sha, R. S., Buelt, M. K., Smith, A. J., Matarese, V., Chinander, L. L., Boundy, K. L., and Bernlohr, D. A. (1989). Human adipocyte lipid-binding protein: purification of the protein and cloning of its complementary DNA. Biochemistry 28: 8683–8690 and Xu, Z., Buelt, M. K., Banaszak, L. J., and Bernlohr, D. A. (1991). Expression, purification and crystallization of the adipocyte lipid binding protein. J. Biol. Chem. 266: 14367–14370). Purification of aP2 from $E.\ coli$ is conducted as described by Xu, yielding essentially homogeneous aP2 protein with molecular weight 14600 daltons and free of endogenous fatty acids. The purified aP2 is capable of binding up to one mole of free fatty acid per mole protein. The binding and structural properties of recombinant aP2 protein were previously shown to be identical to aP2 protein isolated from adipose tissue.

In vitro assay of aP2 inhibitors. Inhibitors of aP2 are evaluated in a homogeneous fluorescent-based competition assay using recombinant aP2 protein and 1,8-anilino-naphthalene-sulfonic acid (1,8-ANS) as assay substrate. This competition assay was adapted from generalized procedures described previously (Kane, C. D. and Bernlohr, D. A. (1996). A simple assay for intracellular lipid-binding proteins using displacement of 1-anilino-8-sulfonic acid. (1996) Anal. Biochem. 233: 197–204 and Kurian E., Kirk, W. R. and Prendergast, F. G. (1996) Affinity of fatty acid for r-rat intestinal fatty acid binding protein. Biochemistry, 35, 3865–3874). The method relies on the increase in fluorescence quantum yield of 1,8-ANS upon binding to the fatty acid binding site of aP2. The assay is run using appropriate concentrations of inhibitor, 1,8-ANS, and aP2 protein, in order to calculate the inhibitor binding constant (Ki) for compounds being evaluated. The Ki calculation was based on the procedure previously described for calculation of dissociation constants described by Kurian. Lower Ki values indicate higher affinities of compounds binding to aP2.

In the assay as conducted for the inhibitors described herein, a series of aliquots of aP2 (5 $\mu$M) in solution in 10 mM potassium phosphate buffer (pH 7.0) are mixed with an equimolar concentration of test compound, followed by the addition of a series of increasing concentrations of 1,8-ANS (from 0 to 5 $\mu$M). The assay typically is conducted in 96-well plate format with reagents added using robotic instrumentation (Packard Multiprobe 104). The fluorescence value for each test is determined using a Cytofluor-4000 multi-well fluorescence plate reader (Perceptive Biosystems) using excitation wavelength 360 nm and emission wavelength 460 nm, or using other suitable spectrofluorometer. In preparation for the assay, test compounds are initially prepared at 10 mM in dimethylsulfoxide. All subsequent dilutions and assay additions are made in 10 mM potassium phosphate buffer, pH 7.0.

X-ray crystallography of the inhibitor-aP2 complex can be performed by one skilled in the art using contemporary biophysical methodologies and commercial instrumentation. Such crystallographic data can be used to conclusively determine if a compound used in the present invention has embodied the structural requirement necessary for inhibition of aP2. An example of such an X-ray crystallographic determination is presented below:

Crystals of aP2 complexed with the inhibitors were typically grown by the hanging drop method. aP2, at 8.3 mg/ml, was pre-equilibrated with 1–5 mM of the inhibitor in 0.1 M Tris-HCl pH 8.0, 1% w/v DMSO for four hours. 2 μl drops containing equilibrated protein and reservoir solution at a 1:1 ratio were suspended on plastic cover slips and equilibrated against a 1 ml reservoir containing 2.6–3.0 M ammonium sulfate in 0.1 M Tris-HCl pH 8.0. Crystals typically appeared in 2–3 days and reached maximum size within 2 weeks. Data was typically collected on a single flash-frozen crystal (Oxford Cryosystems) using a Rigaku rotating anode and an R-axis II image plate detector of a Bruker multiwire area detector. Diffraction from aP2 crystals was excellent. Diffraction was consistently observed to better than 2.0 Å resolution often to beyond 1.5 Å resolution. Data was processed either with DENZO/SCALEPACK (R-axis II data), or Xengen (Bruker data). XPLOR was used for structure refinement and model building was done using the molecular modeling package CHAIN. After a single round of refinement, examination of the $F_o$-$F_c$ map typically allowed facile building of the inhibitor into aP2 binding cavity. Iterative fitting and refinement were continued until improvement was no longer seen in the electron density map or R-free.

The following working Examples represent preferred embodiments of the invention.

EXAMPLE 1

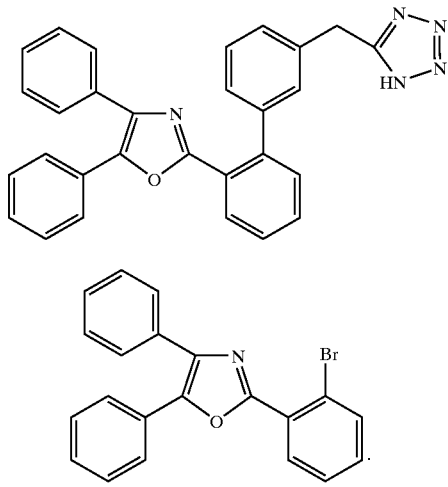

A

A solution of 2-bromo-benzoic acid (21.8 g, 108 mmol), 4-dimethyl amino pyridine (1 g, 8.19 mmol), 1-(3-dimethylaminopropyl)-3-ethylcarbodiimide hydrochloride (22.6 g, 118 mmol) and benzoin (20 g, 94.2 mmol) in dichloromethane (200 mL) was stirred at room temperature for 4 hr. The reaction mixture was washed with water (2×50 mL), brine (50 mL), dried over anhydrous $MgSO_4$ and concentrated to give the ketoester as a colorless oil (36 g).

A mixture of ketoester (36 g, 94.2 mmol) and ammonium acetate (36 g, 471 mmol) in glacial acetic acid (350 mL) was stirred at reflux for 1.5 hr. The reaction mixture was cooled, diluted with water, and extracted with ethyl acetate (3×300 mL). The combined organic layers were washed with water (2×100 mL), saturated aqueous sodium bicarbonate solution (2×100 mL), and brine (100 mL), dried over anhydrous $MgSO_4$ and concentrated to get yellow-orange oil. The crude product was recrystallized from hot methanol to get the title compound as off-white solid (21.6 g, 61%).

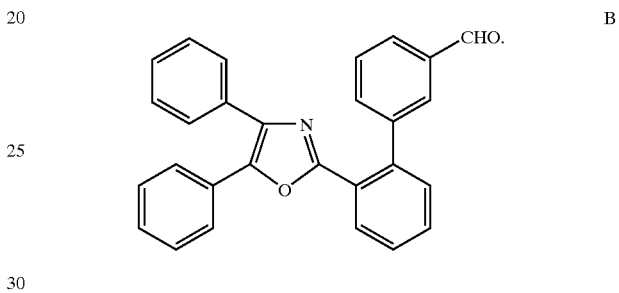

B

Nitrogen was bubbled through a solution of Part A compound (1.48 g, 3.93 mmol), 3-formyl phenyl boronic acid (766 mg, 5.11 mmol) and aqueous sodium carbonate (3.2 mL, 2M, 6.4 mmol) in toluene (10 mL) and ethanol (4.2 mL) at room temperature for 30 min. Tetrakis (triphenylphosphine) palladium(0) (150 mg, 0.13 mmol) was added and the mixture was stirred at 80° C. for 14 hr under argon. The reaction mixture was cooled to room temperature and extracted with ethyl acetate. The combined organic extracts were washed with brine, dried over anhydrous $MgSO_4$ and concentrated. The crude product was purified by flash chromatography on silica gel, eluting with a step gradient of 1:9 to 2:8 ethyl acetate/hexane to give title compound as a colorless oil (800 mg, 51%).

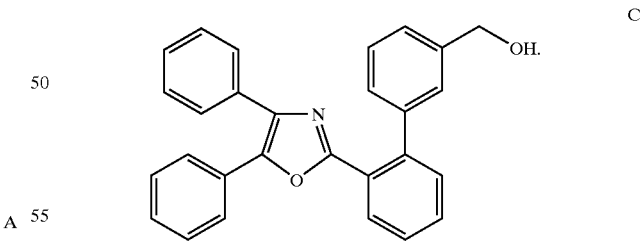

C

Sodium borohydride (19 mg, 0.5 mmol) was added slowly to a solution of Part B compound (494 mg, 1.23 mmol) in anhydrous methanol (2 mL) at 0° C. The reaction was stirred for 2 hr at 0° C., and then warmed to room temperature. The pH was adjusted to 2 with conc. HCl and concentrated. The residue was partitioned between ethyl acetate and water. The organic layer was washed with water, dried ($MgSO_4$) and concentrated to give the title compound as a white foam (360 mg, 89%).

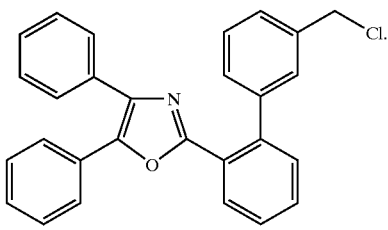

D

To a stirred solution of Part C compound (7.5 g, 18.6 mmol) in dioxane (62 mL) at room temperature was added zinc chloride (78 mg, 0.54 mmol) followed by thionyl chloride (2.74 mL, 37.5 mmol). The reaction was stirred for 1 hr and concentrated. The residue was dissolved in ethyl acetate, washed with brine, dried over anhydrous MgSO$_4$ and concentrated to give the title compound as a viscous oil (8.0 g, 100%).

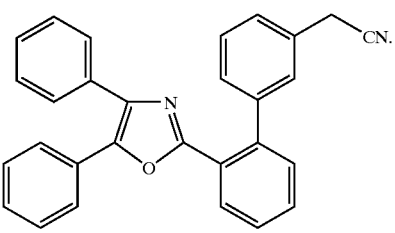

E

A solution of Part D compound (8.0 g, 18.6 mmol) and sodium cyanide (1.39 g, 28.2 mmol) in acetonitrile (75 mL) and water (7 mL) was stirred at reflux for 14 hr. The reaction mixture was cooled to room temperature, concentrated. The residue was partitioned between dichloromethane and water. The organic layer was dried (MgSO$_4$) and concentrated. The crude product was purified by flash chromatography on silica gel, eluting with a step gradient of 5:95 to 15:85 ethyl acetate/hexane to give title compound as a white solid (6.4 g, 83.6%).

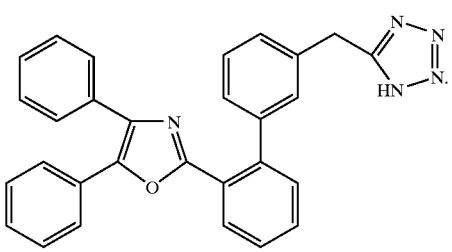

F

A solution of Part E compound (6.18 g, 15.0 mmol) and azidotrimethyltin (4.32 g, 21.0 mmol) in xylene (50 mL) was refluxed for 18 hr. The reaction mixture was cooled to room temperature, methanol (150 mL) was added and the mixture was stirred for 30 min and concentrated. The crude product was purified by flash chromatography on silica gel, eluting with a step gradient of 3:7 to 5:5 ethyl acetate/hexane and then with 95:5 dichloromethane/methanol to give title compound as a white solid (5.96 g, 87%). The compound can be recrystallized from hot ethanol.

EXAMPLE 2

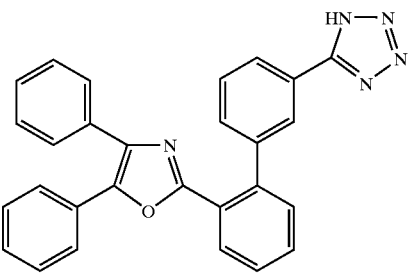

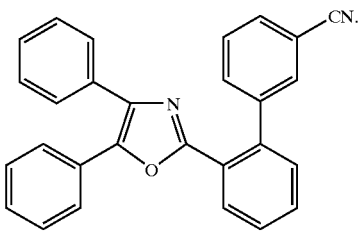

A

Example 1 Part B compound (401 mg, 1 mmol) was added to a solution of silicon tetrachloride (170 mg, 115 μL, 1 mmol) and sodium azide (195 mg, 3 mmol) in anhydrous acetonitrile (3 mL) at 0° C. The reaction mixture was warmed to room temperature, then to 50° C. and stirred for 24 hr. The reaction was cooled to room temperature and poured into aqueous saturated sodium carbonate solution. The pH of the mixture was adjusted between 9–10 with sodium carbonate solution and it was extracted with chloroform (3×10 mL). The combined organic layers were washed with water, dried over anhydrous MgSO$_4$ and concentrated. The crude product was purified by flash chromatography on silica gel, eluting with a step gradient of 3:97 to 5:95 ethyl acetate/hexane to give title compound as a colorless oil (200 mg, 50%).

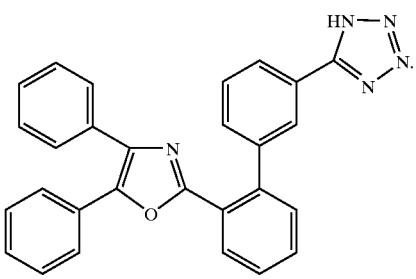

B

A solution of Part A compound (199 mg, 0.5 mmol) and azidotrimethyltin (145 mg, 0.7 mmol) in xylene (5 mL) was heated at 100° C. for 18 hr. The reaction mixture was cooled to room temperature, methanol (8 mL) was added, stirred for 30 min, filtered and concentrated. Flash chromatography on silica gel, eluting with 1:4 ethyl acetate/hexane and then with 95:5:0.15 dichloromethane/methanol/acetic acid gave impure product. Furthur purification by flash chromatography on silica gel, eluting with a step gradient of 1:4 to 1:1 ethyl acetate/hexane and then with 95:5 to 90:10 dichloromethane/methanol gave the title compound as a foam (70 mg, 32%).

EXAMPLE 3

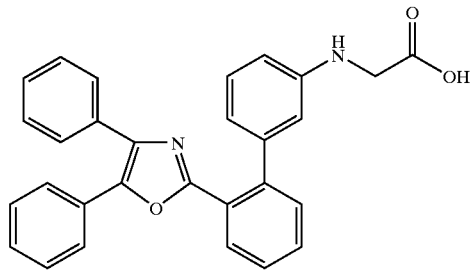

A

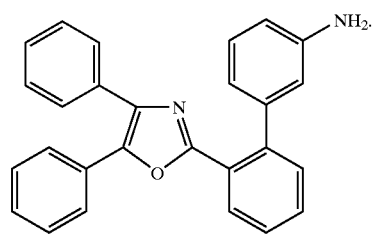

Nitrogen was bubbled through a solution of Example 1 Part A compound (5 g, 13.29 mmol), 3-amino phenyl boronic acid (2.37 g, 17.29 mmol) and sodium carbonate (11 mL, 2M, 22 mmol) in toluene (40 mL) and ethanol (15 mL) at room temperature for 30 min. Tetrakis (triphenylphosphine)-palladium(0) (508 mg, 0.43 mmol) was added and the reaction mixture was heated at 80° C. for 18 hr. The reaction mixture was cooled to room temperature and partitioned between diethyl ether and water. The organic layer was washed with water, brine, dried over anhydrous $MgSO_4$ and concentrated. The crude product was purified by flash chromatography eluting with 1:3 ethyl acetate/hexane to give title compound as a pale yellow foam (2.56 g, 49%).

B

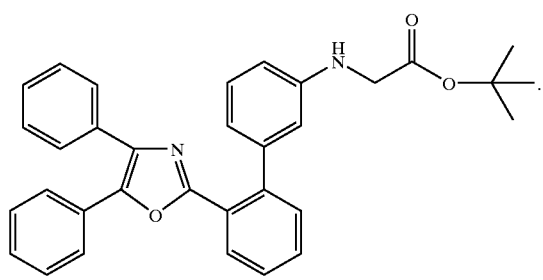

To a slurry of Part A compound (2.56 g, 6.60 mmol) and potassium carbonate (918 mg, 6.60 mmol) in anhydrous dimethyl formamide (20 mL) was added tert-butyl bromoacetate (975 µL, 6.60 mmol). The reaction mixture was stirred at room temperature for 18 hr. Additional tert-butyl bromoacetate (150 µL, 1.01 mmol) was added and the mixture was stirred for 7 hr. The reaction was partitioned between diethyl ether and aqueous sodium bicarbonate solution. The organic layer was washed with water, and brine, then dried over anhydrous $MgSO_4$ and concentrated. The crude product was purified by flash chromatography eluting with 15:85 ethyl acetate/hexane to give title compound as a foam (2.230 g, 67%).

C

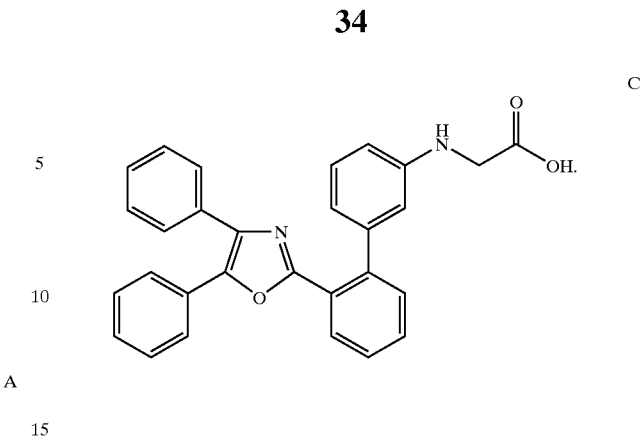

A solution of Part B compound (2.230 g, 4.4 mmol) in trifluoroacetic acid (15 mL) and dichloromethane (40 mL) was stirred at room temperature for 18 hr. The reaction mixture was concentrated, the residue was partitioned between ethyl acetate and water. The aqueous layer was basified with 1N NaOH and then the pH was adjusted between 3–4 with 10% citric acid solution. The organic layer was separated and washed with water and brine, dried over anhydrous $MgSO_4$ and concentrated. The crude product was purified by flash chromatography eluting with 7:93 methanol/dichloromethane to give an oily foam which was triturated from ethyl acetate/hexane to get the title compound as a yellow foam (1.692 g, 86%).

EXAMPLE 4

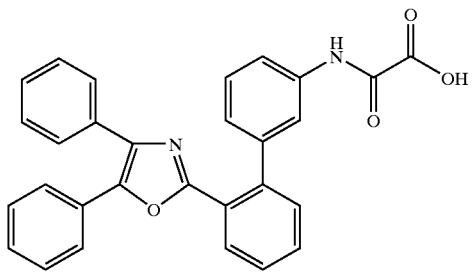

To a solution of Example 3 Part A compound (149 mg, 0.38 mmol) in dichloromethane (2 mL) was added diisopropylethylamine (100 µL), followed by ethyl oxalyl chloride (147 µL, 0.42 mmol). The reaction was stirred for 2 hr, partitioned between ethyl acetate and aqueous HCl (1N). The organic layer was washed with water, saturated sodium bicarbonate solution, and brine, dried over anhydrous $MgSO_4$ and concentrated to get the crude ester as a yellow-brown foam (189 mg). To a solution of the crude ester in methanol (3 mL) was added dropwise aqueous NaOH (~800 µL, 1N) until the solution became turbid. Precipitate was formed after stirring the solution overnight. The reaction was partitioned between ethyl acetate and aqueous HCl (1N). The organic layer was washed with water, and brine, dried over anhydrous $MgSO_4$ and concentrated. The crude product was triturated with ethyl acetate and hexane to give the title compound as an off-white solid (118 mg, 67%).

EXAMPLE 5

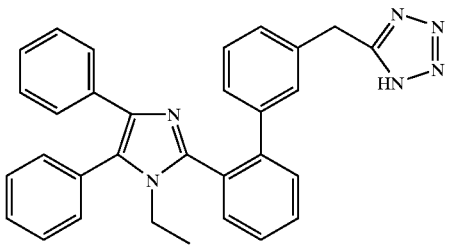

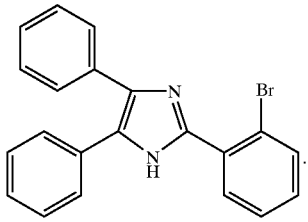
A

A mixture of benzil (10 g, 47.6 mmol) and ammonium acetate (44 g, 564 mmol) in glacial acetic acid (260 mL) was treated with 2-bromobenzaldehyde (5.5 mL, 47.6 mmol) and stirred at 105° C. for 3 hr. The reaction mixture was cooled, diluted with water, and the precipitate was filtered. The solid was dissolved in warm ethyl acetate. The organic layer was washed with water, and brine, dried over anhydrous $MgSO_4$ and concentrated. The crude product was triturated from ethyl acetate/hexane to give the title compound as an off-white solid (16.55 g, 93%).

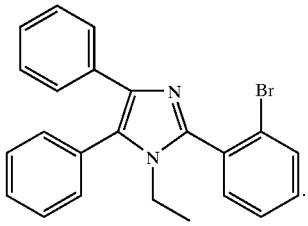
B

To a solution of Part A compound (2.5 g, 6.67 mmol) and ethyl iodide (1.15 g, 7.3 mmol) in anhydrous dimethylformamide (17 mL) was added potassium carbonate (922 mg, 6.67 mmol). The reaction mixture was stirred at room temperature overnight, partitioned between ethyl acetate/water. The organic layer was washed with water, dried over anhydrous $MgSO_4$ and concentrated to give the title compound as a semi-solid (2.5 g, 94%).

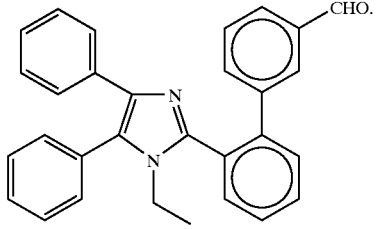
C

Nitrogen was bubbled through a solution of Part B compound (2.0 g, 4.96 mmol), 3-formyl phenyl boronic acid (966 mg, 6.44 mmol) and aqueous sodium carbonate (4 mL, 2M, 8 mmol) in toluene (15 mL) and ethanol (8 mL) at room temperature for 30 min. Tetrakis(triphenylphosphine) palladium(0) (190 mg, 0.16 mmol) was added and the mixture was stirred at 80° C. for 36 hr under argon. The reaction mixture was cooled to room temperature and extracted with ethyl acetate. The combined organic extracts were washed with brine, dried over anhydrous $MGSO_4$ and concentrated. The crude product was purified by flash chromatography on silica gel, eluting with a step gradient of 1:9 to 2:8 ethyl acetate/hexane to give title compound as an oil (1.7 g, 80%).

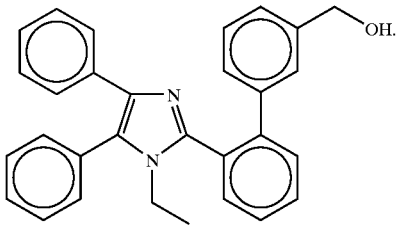
D

Sodium borohydride (57 mg, 1.51 mmol) was added slowly to a solution of Part C compound (900 mg, 2.1 mmol) in anhydrous methanol (5 mL) at 0° C. The reaction was stirred for 2 hr at 0° C. Additional sodium borohydride (57 mg, 1.51 mmol) was added and stirring was continued for 2 hr and then the reaction mixture was warmed to room temperature. The mixture was partitioned between ethyl acetate/chloroform and water. The organic layer was washed with water, dried ($MgSO_4$) and concentrated to give the title compound as a white foam (650 mg, 72%).

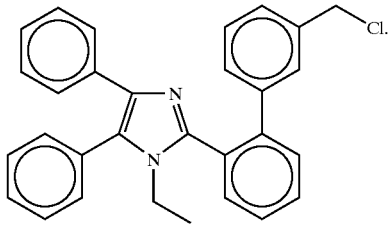
E

To a stirred solution of Part D compound (645 mg, 1.5 mmol) in dioxane (8 mL) at room temperature was added zinc chloride (6 mg, 0.045 mmol) followed by thionyl chloride (220 µL, 3.0 mmol). The reaction was stirred for 1 hr and concentrated. The residue was dissolved in ethyl acetate, washed with brine and 5% aqueous sodium bicarbonate solution, dried over anhydrous $MgSO_4$ and concentrated to give the title compound as a foam (650 mg, 95%).

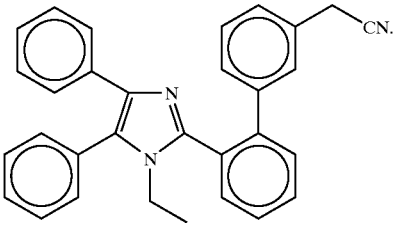
F

A solution of Part E compound (600 mg, 1.34 mmol) and sodium cyanide (92 mg, 1.88 mmol) in acetonitrile (6 mL)

and water (400 μL) was stirred at reflux overnight. Additional sodium cyanide (92 mg, 1.88 mmol) in water (400 μL) was added and the refluxing continued for 6 hr. Additional sodium cyanide (50 mg, 1.01 mmol) in water (400 μL) was added and refluxing was continued for 2 hr. The reaction mixture was cooled to room temperature and concentrated. The residue was partitioned between dichloromethane and water. The organic layer was dried (MgSO₄) and concentrated. The crude product was purified by flash chromatography on silica gel, eluting with a step gradient of 10:90 to 30:70 ethyl acetate/hexane to give title compound as a white solid (300 mg, 51%).

carbonate (2 mL, 2M, 4 mmol) in toluene (7 mL) and ethanol (4 mL) at room temperature for 30 min. Tetrakis (triphenylphosphine) palladium(0) (95 mg, 0.08 mmol) was added and the mixture was stirred at 80° C. overnight under argon. The reaction mixture was cooled to room temperature and extracted with ethyl acetate. The combined organic extracts were washed with brine, dried over anhydrous MgSO₄ and concentrated. The crude product was purified by flash chromatography on silica gel, eluting with a step gradient of 2:8 to 3:7 ethyl acetate/hexane to give title compound as a white solid (400 mg, 39%).

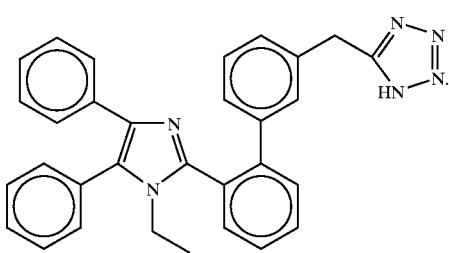

G

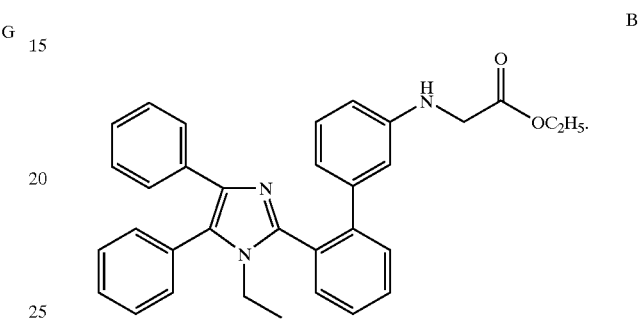

B

A solution of Part F compound (255 mg, 0.58 mmol) and azidotrimethyltin (167 mg, 0.81 mmol) in xylene (2 mL) was heated at 130° C. overnight. The reaction mixture was cooled to room temperature, methanol (8 mL) was added and the mixture was stirred for 30 min. The milky white precipitate was filtered and the filtrate was concentrated. The crude product was purified by flash chromatography on silica gel, eluting with a step gradient of 1:1 ethyl acetate/hexane and then with 95:5 dichloromethane/methanol to give title compound as a white foam (216 mg, 77%).

The mixture of Part A compound (400 mg, 0.96 mmol), diisopropylethylamine (333 μL, 1.92 mmol), and ethylbromoacetate (95 μL, 0.86 mmol) in anhydrous dimethylformamide (3 mL) was stirred at room temperature overnight. The reaction mixture was partitioned between ethyl acetate and water. The organic layer was washed with water, brine, dried over anhydrous MgSO₄ and concentrated. The crude product was purified by flash chromatography on silica gel, eluting with a step gradient of 2:8 to 3:7 ethyl acetate/hexane to give title compound as a foam (400 mg, 83%).

EXAMPLE 6

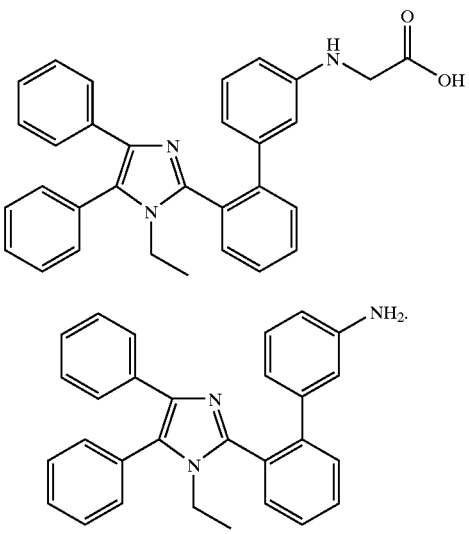

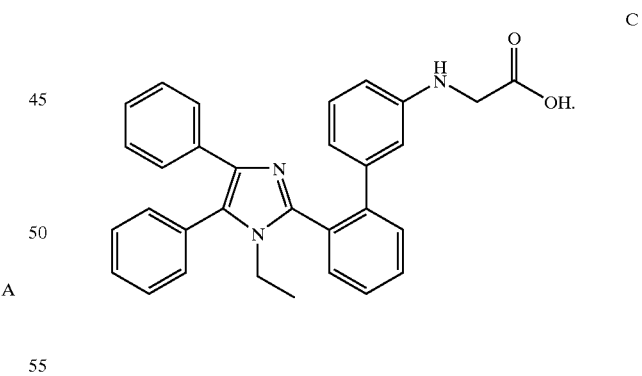

C

A

A solution of Part B compound (400 mg, 0.77 mmol) in aqueous sodium hydroxide (2.3 mL, 1N, 2.3 mmol) and methanol (15 mL) was stirred at room temperature for 2 hr. The reaction mixture was concentrated to a white suspension in water bath at 30° C. The suspension was dissolved in distilled water. The pH was adjusted to 4 by aqueous citric acid (1N). The white precipitate was dissolved in ethyl acetate. The organic layer was washed with water, brine, dried over anhydrous MgSO₄ and concentrated to give the title compound as a foam (350 mg, 96%).

Nitrogen was bubbled through a solution of Example 5 Part B compound (1.0 g, 4.96 mmol), 3-aminophenyl boronic acid (442 mg, 3.22 mmol) and aqueous sodium

EXAMPLE 7

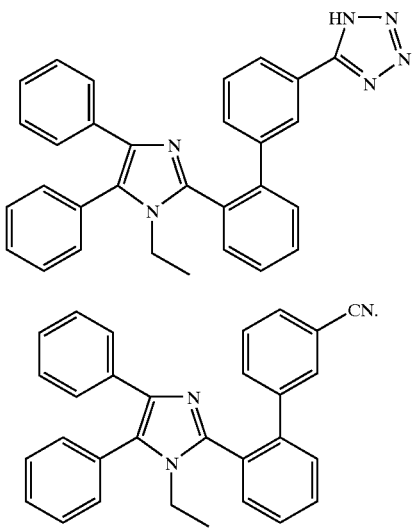

A

EXAMPLE 8

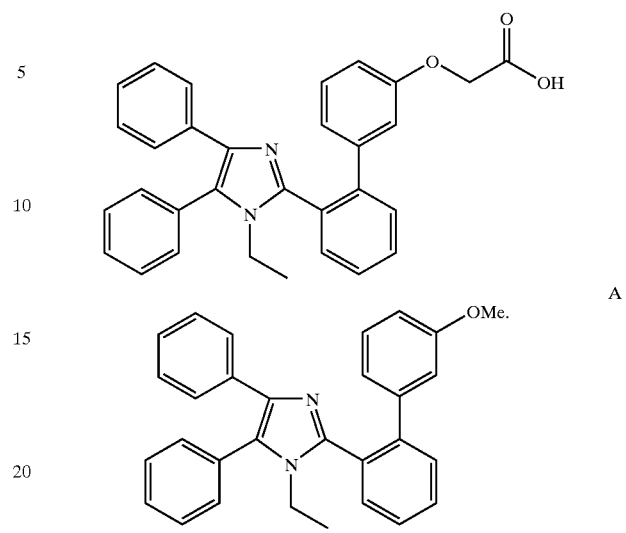

A

Example 5 Part C compound (214 mg, 0.5 mmol) was added to a solution of silicon tetrachloride (58 μL, 0.5 mmol) and sodium azide (98 mg, 1.5 mmol) in anhydrous acetonitrile (3 mL) at 0° C. The reaction mixture was warmed to room temperature, then to 50° C. and stirred for 48 hr. The reaction was cooled to room temperature and poured into aqueous saturated sodium carbonate solution. The pH of the mixture was adjusted between 9–10 with sodium carbonate solution and it was extracted with chloroform twice. The combined organic layers were washed with water, dried over anhydrous $MGSO_4$ and concentrated. The crude product was purified by flash chromatography on silica gel, eluting with a step gradient of 15:85 to 20:80 ethyl acetate/hexane to give title compound as a foam (56 mg, 26%).

Nitrogen was bubbled through a solution of Example 5 Part B compound (4.925 g, 17.2 mmol), 3-methoxy phenyl boronic acid (3.50 g, 23.0 mmol) and 2M aqueous sodium carbonate (14 mL) in toluene (50 mL) and absolute ethanol (20 mL) at room temperature for 30 min. Tetrakis (triphenylphosphine) palladium(0) (795 mg, 0.68 mmol) was added and the mixture was stirred at 80° C. for 18 hr under argon. The reaction mixture was cooled to room temperature and partitioned between ethyl acetate/diethyl ether and water. The organic layer was washed with brine, dried over anhydrous $MgSO_4$ and concentrated. The crude product was purified by flash chromatography on silica gel, eluting with 1:3 ethyl acetate/hexane to give title compound as a light yellow foam (7.34 g, 99%).

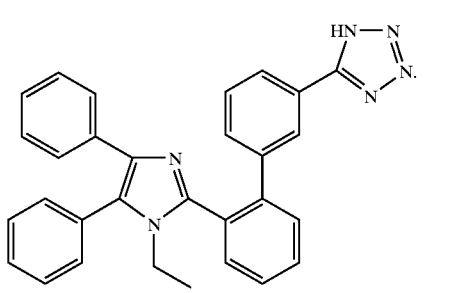

B

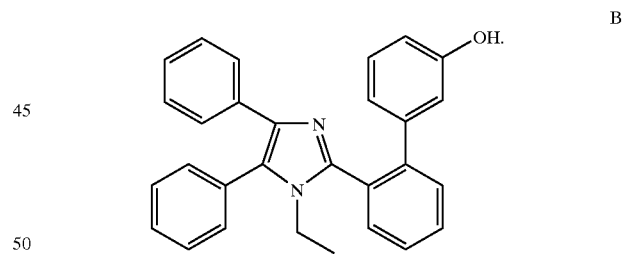

B

A solution of Part A compound (50 mg, 0.11 mmol) and azidotrimethyltin (34 mg, 0.16 mmol) in xylene (3 mL) was heated at 100° C. for 48 hr. The reaction mixture was concentrated to remove all xylene. Fresh xylene (250 μL) and azidotrimethyltin (34 mg, 0.16 mmol) was added and the mixture was heated at 130° C. overnight. The reaction mixture was cooled to room temperature, methanol (8 mL) was added, stirred for 30 min, filtered and concentrated. Flash chromatography on silica gel, eluting with a step gradient of 1:4 to 1:1 ethyl acetate/hexane and then with 95:5 to 90:10 dichloromethane/methanol gave the title compound as a foam (45 mg, 87%).

To a solution of Part A compound (7.341 g, 17.07 mmol) in anhydrous dichloromethane (100 mL) at 0° C. was added boron tribromide in dichloromethane (38 mL, 1M, 38 mmol). The reaction was stirred for 1.5 hr, quenched with aqueous sodium bicarbonate solution and extracted with ethyl acetate. The organic layer was washed with water, and brine, then dried over anhydrous $MgSO_4$, filtered quickly and concentrated. The solid was triturated with ether/ethyl acetate/methanol to give the title compound as a white solid (3.156 g, 91% purity). The mother liquor was concentrated and purified by flash chromatography on silica gel, eluting with 15:85 ethyl acetate/hexane to give title compound which was triturated from ether/dichloromethane to give a white solid (626 mg, >95% purity).

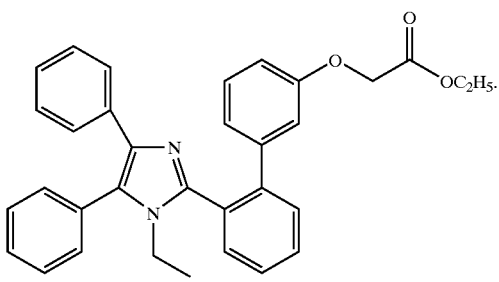

C

A slurry of Part B compound (91% pure, 3.15 g) in anhydrous dimethylformamide (35 mL) was warmed to partially dissolve the phenol. The mixture was cooled to 30° C. and potassium carbonate (920 mg, 6.6 mmol) was added followed by ethyl bromoacetate (1.35 mL, 12.12 mmol). The reaction mixture was stirred at room temperature for 24 hr. Additional potassium carbonate (920 mg, 6.6 mmol) and ethyl bromoacetate (1.35 mL, 12.12 mmol) was added and stirring was continued for 40 hr. The reaction mixture was partitioned between ethyl acetate and water. The organic layer was washed with water, and brine, then dried over anhydrous MgSO$_4$ and concentrated. The crude product was purified by flash chromatography on silica gel, eluting with 1:9 ethyl acetate/dichloromethane to give title compound as a white foam (2.678 g, 77%).

D

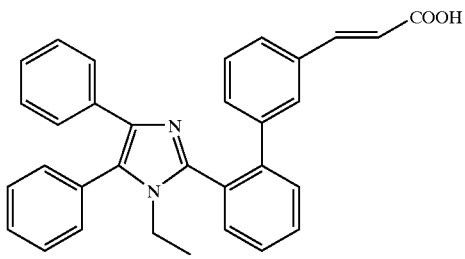

A solution of Part C (2.670 g, 5.31 mmol) compound in 1,4-dioxane (15 mL) was treated with sodium hydroxide solution (13 mL, 1N, 13 mmol). The reaction mixture was stirred at 50° C. for 45 min. The reaction mixture was cooled to room temperature and acidified with aqueous citric acid solution (25 mL, 10%). The mixture was diluted with water (120 mL) and stirred vigorously for 30 min. The precipitate was filtered, washed with water and dried to give the title compound as a white solid (2.533 g 100%)

EXAMPLE 9

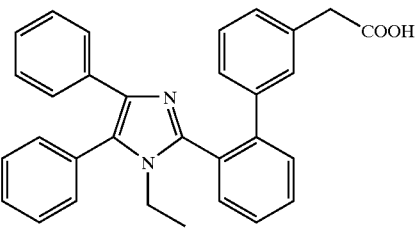

Neat triethyl phosphonate (201 μL, 1.28 mmol) was added dropwise to a stirred suspension of sodium hydride (52 mg, 1.28 mmol) in anhydrous tetrahydrofuran (2 mL). The mixture was stirred at room temperature for 1 hr followed by slow addition of Example 5 Part C compound (500 mg, 1.16 mmol) in anhydrous tetrahydrofuran (2 mL). The reaction mixture stirred for 5 hr. Additional sodium hydride (20 mg, 0.50 mmol) was added and stirring was continued for 1 hr. The reaction mixture was partitioned between diethyl ether and water. The organic layer was washed with water, dried over anhydrous MgSO$_4$ and concentrated. The residue was purified by flash chromatography on silica gel, eluting with 3:7 ethyl acetate/hexane to give the Example 9 ethyl ester (167 mg, 29%).

A portion of the ester was hydrolyzed during the work up. The above aqueous layer was acidified with aqueous citric acid to pH 2. The separated solid was extracted with ether. The organic layer was washed with water, dried over anhydrous MgSO$_4$ and concentrated. The crude product was purified by flash chromatography on silica gel, eluting with a step gradient of 2:98 to 1:9 methanol/dichloromethane to give title compound as a foam (30 mg, 6%). The title compound is also readily obtained by base hydrolysis of the intermediate ester.

EXAMPLE 10

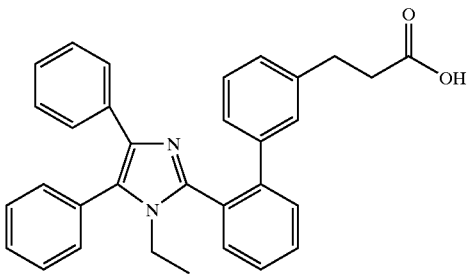

A solution of Example 5 Part F compound (44 mg, 0.1 mmol) in aqueous sodium hydroxide (250 μL, 10N, 2.5 mmol) and ethanol (2 mL) was refluxed for 5 hr and then stirred at room temperature for 14 hr. The reaction mixture was concentrated and the residue was dissolved in water. The pH was adjusted to 4 by acetic acid. The precipitate was filtered and dissolved in chloroform. The organic solution was washed with brine, dried over anhydrous MgSO$_4$ and concentrated. The crude product was purified by flash chromatography on silica gel, eluting with a step gradient of 2:8 ethyl acetate/hexane and then with 95:5 to 90:10 dichloromethane/methanol to give title compound as a foam (34 mg, 62%).

EXAMPLE 11

A

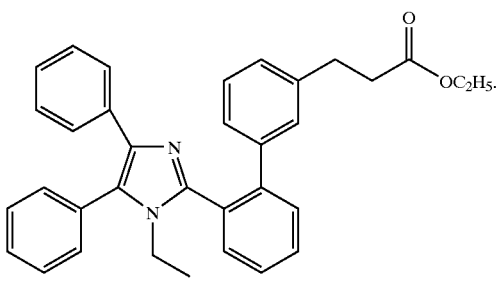

A slurry of the ester described in Example 9 (100 mg, 0.20 mmol) and 10% palladium on carbon (20 mg) in methanol (3 mL) was stirred in a parr shaker under hydrogen (40 psi) for 2 hr. The reaction mixture was filtered through a pad of Celite 525 and concentrated to give the title compound as a colorless oil (100 mg, 98%).

B

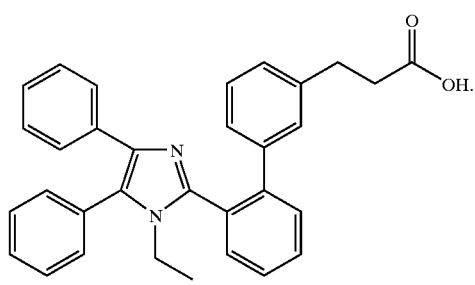

A solution of Part A compound (100 mg, 0.2 mmol) in aqueous potassium hydroxide (600 μL, 2N, 1.2 mmol) and tetrahydrofuran (2 mL) was refluxed for 48 hr. The reaction mixture was concentrated and the residue was dissolved in water. The pH was adjusted to 2 by aqueous HCl(1N). The white precipitate was extracted into ethyl acetate. The combined organic extracts were washed with brine, dried over anhydrous MgSO$_4$ and concentrated to give a foam. The crude product was purified by flash chromatography on silica gel, eluting with a step gradient of 98:2 to 95:5 dichloromethane/methanol to give title compound as a foam (32 mg, 34%).

EXAMPLE 12

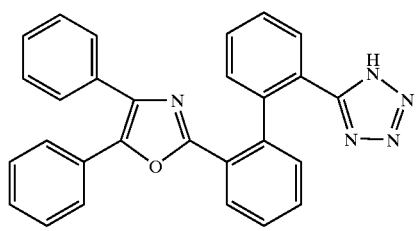

A

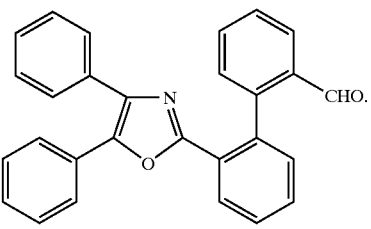

Nitrogen was bubbled through a solution of Example 1 Part A compound (10 g, 26.57 mmol), 1-formyl phenyl boronic/acid (5.18 g, 34.55 mmol) and aqueous sodium carbonate (21.25 mL, 2M, 42.5 mmol) in toluene (70 mL) and ethanol (27 mL) at room temperature for 30 min. Tetrakis (triphenylphosphine) palladium(0) (1 g, 0.86 mmol) was added and the mixture was stirred at 80° C. for 14 hr under argon. The reaction mixture concentrated and diluted with ethyl acetate/water. The aqueous layer was extracted with ethyl acetate (2×200 mL). The combined organic extracts were washed with brine, dried over anhydrous MgSO$_4$ and concentrated. The crude product was purified by flash chromatography on silica gel, eluting with a step gradient of 1:19 to 2:8 ethyl acetate/hexane to give title compound as a yellow solid (6.11 g, 57.3%). Less pure fractions were also collected 2.84 g.

B

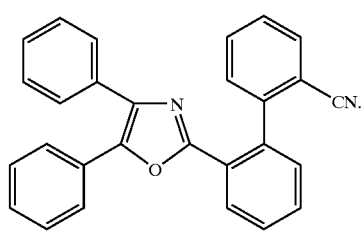

Part A compound (1 g, 2.49 mmol) was added to a solution of silicon tetrachloride (285 μL, 2.49 mmol) and sodium azide (0.486 g, 7.47 mmol) in anhydrous acetonitrile (10 mL) at 0° C. The reaction mixture was warmed to room temperature, then to 50° C. and stirred for 18 hr. The reaction was cooled to room temperature and poured into a mixture of ethyl acetate and aqueous saturated sodium carbonate solution. The pH of the mixture was adjusted between 9–10 with sodium carbonate solution and the aqueous layer was extracted with ethyl acetate (3×100 mL). The combined organic layers were washed with brine, dried over anhydrous MgSO$_4$ and concentrated the title compound as a yellow oil (1.06 g, 107%).

C

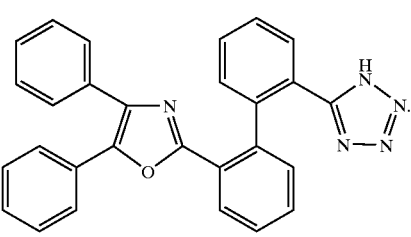

A solution of Part B compound (0.20 g, 0.50 mmol) and azidotrimethyltin (0.140 g, 0.70 mmol) in p-xylene (2 mL) was refluxed for 18 hr. The reaction mixture was cooled to room temperature, methanol (10 mL) was added and the mixture was stirred for 30 min and concentrated. The crude product was purified by flash chromatography on silica gel, eluting with a step gradient of 8:2 ethyl acetate/hexane to 9:1:0.5 dichloromethane/methanol/acetic acid to give title compound as a solid (0.107 g, 48.6%)

EXAMPLE 13

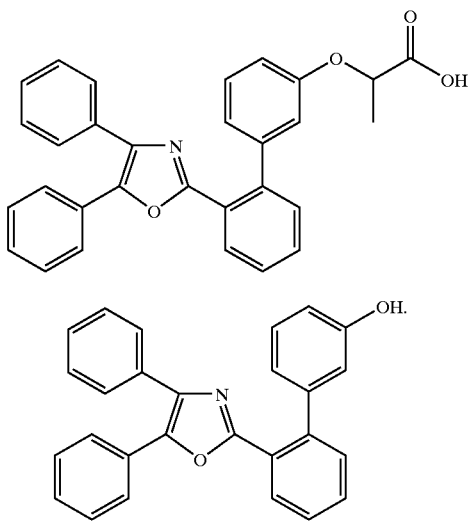

To a solution of Example 1 Part A compound (7.52 g, 20 mmol) in anhydrous tetrahydrofuran (100 mL) at −78° C. was added dropwise n-butyl lithium in hexane (9.3 mL, 2.5 N, 23.25 mmol). The reaction mixture was stirred for 15 min followed by addition of sublimed zinc bromide (5.2 g. 23.1 mmol) in anhydrous tetrahydrofuran (40 mL). To this blue solution was added O-t-butyldimethylsilyl-3-iodophenol (6.7 g, 21.1 mmol) in tetrahydrofuran (40 mL) followed by tetrakis(triphenylphosphine) palladium(0) (1.2 g, 0.96 mmol). The reaction was stirred at −78° C. for 30 min and then at room temperature for 20 hr. The reaction mixture was quenched with saturated aqueous ammonium chloride solution and extracted with diethyl ether thrice. The combined organic layers were dried over anhydrous MgSO$_4$ and concentrated to get crude amber oil.

To a solution of the crude amber oil in anhydrous tetrahydrofuran (100 mL) was added dropwise tetrabutyl ammonium fluoride in tetrahydrofuran (25 mL, 1 M, 25 mmol). The solution was stirred at room temperature for 1 hr, quenched with saturated aqueous ammonium chloride solution and extracted with diethyl ether thrice. The combined organic layers were washed with saturated aqueous ammonium chloride solution, dried over anhydrous MgSO$_4$ and concentrated. The crude product was purified by flash chromatography on silica gel, eluting with 2:8 ethyl acetate/hexane to give title compound as a yellow foam (4.6 g, 59%).

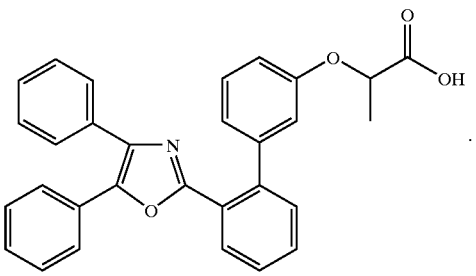

To a slurry of Part A compound (200 mg, 0.51 mmol) and cesium carbonate (217 mg, 0.67 mmol) in anhydrous dimethylformamide (10 mL) was added ethyl 2-bromopropionate (121 mg, 0.67 mmol). The reaction mixture was stirred at room temperature for 18 h, diluted with water (20 mL), extracted with ethyl acetate (3×20 mL). The organic layer was washed with water, and brine, then dried over anhydrous MgSO$_4$ and concentrated to get the crude ester as a yellow oil.

A solution of crude ester in aqueous sodium hydroxide solution (5 mL, 1N) and dioxane (5 mL) was refluxed for 20 min. The reaction mixture was cooled, concentrated, diluted with water and pH was adjusted to 1 with HCl (1N). The mixture was extracted with ethyl acetate (3×20 mL). The combined organic layers were washed with water, and brine, dried over anhydrous MgSO$_4$ and concentrated. The crude product was purified by flash chromatography on silica gel, eluting with 75:25 ethyl acetate/methanol to give title compound as a off-white powder (208 mg, 88%).

EXAMPLE 14

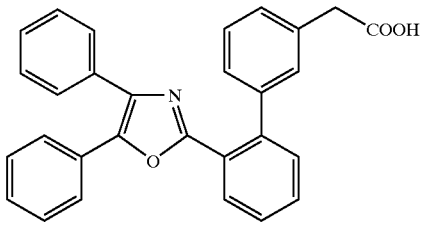

A solution of Example 1 Part E compound (165 mg, 0.4 mmol) in aqueous sodium hydroxide (1 mL, 10N, 10 mmol) and ethanol (3 mL) was refluxed for 5 h and then stirred at room temperature for 14 h. The reaction mixture was concentrated and the residue was dissolved in water. The pH was adjusted to 4 by acetic acid. The precipitate was filtered and dissolved in chloroform. The organic solution was filtered and the filtrate was concentrated to get the title compound as an off-white solid (95 mg, 55%).

EXAMPLE 15

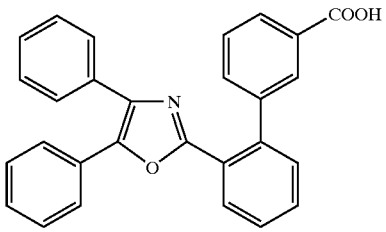

To a solution of Example 1 Part C compound (75 mg, 0.18 mmol) in tetrahydrofuran (4 mL) at 0° C. was added sulfamic acid (19 mg, 0.18 mmol) as a solid. To this cold solution was added dropwise a solution of sodium chlorite (20 mg, 0.18 mmol) in water (2 mL) over 10 min. The reaction was stirred for 1 hr and then partitioned between ether and brine. The organic layer was dried over anhydrous $MgSO_4$ and concentrated. The crude product was purified by flash chromatography on silica gel, eluting with a step gradient 2:8 ethyl acetate/hexane to 5:95 methanol/dichloromethane to give title compound as a white solid (53 mg, 71%).

EXAMPLE 16

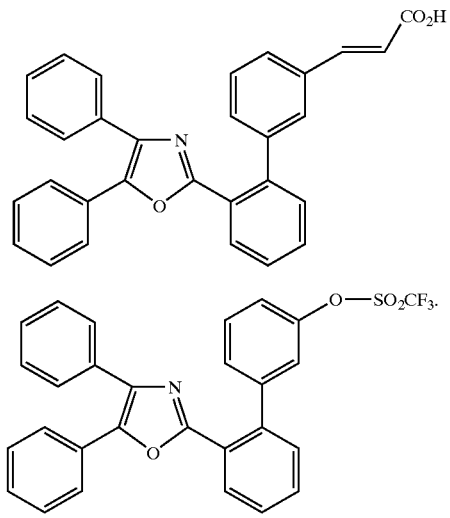

To a solution of Example 13 Part A compound (389 mg, 1 mmol) and triethylamine (420 μL, 3 mmol) in dichloromethane (25 mL) at 0° C. was added slowly triflic anhydride (185 μL, 1.1 mmol). The reaction was warmed to room temperature over 2 hr, washed with water, dried over anhydrous $MgSO_4$ and concentrated. The crude product was purified by flash chromatography on silica gel, eluting with 1:4 ethyl acetate/hexane to give title compound as a brown oil (485 mg, 93%).

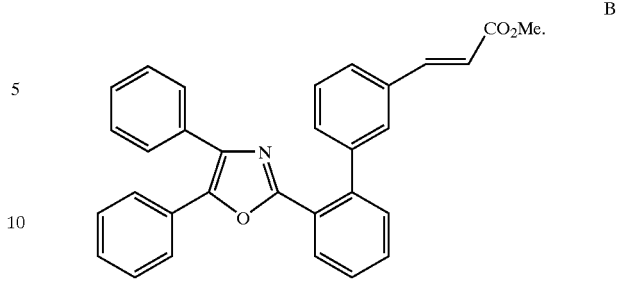

A mixture of Part A compound (485 mg, 0.93 mmol), triethylamine (142 μL, 1.02 mmol), 1,3-bis(diphenylphosphino) propane (11 mg, 0.02 mmol), methyl acrylate (167 μL, 1,86 mmol) and palladium acetate (5.2 mg, 0.02 mmol) in dimethylformamide (10 mL) was refluxed overnight at 100° C. The reaction mixture was cooled to room temperature, diluted with dichloromethane. The organic layer was washed with aqueous 1 N HCl, water, brine, dried over anhydrous $MgSO_4$ and concentrated. The crude product was purified by flash chromatography on silica gel, eluting with 15:85 ethyl acetate/hexane to give title compound as an off-white powder (234 mg, 55%).

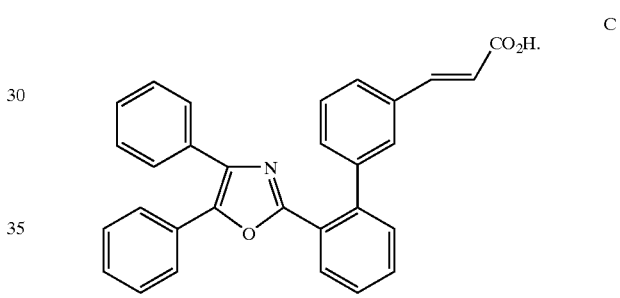

A solution of Part B compound (234 mg, 0.51 mmol) in 1,4-dioxane (5 mL) and sodium hydroxide (5 mL, 1M, 5 mmol) was refluxed for 0.5 hr. The reaction mixture was cooled to room temperature, pH was adjusted to 2 with HCl solution (1 M), and then extracted with ethyl acetate (2×20 mL). The combined organic layers were washed water, and brine, then dried over anhydrous $MgSO_4$ and concentrated to give the title compound as a white solid (198 mg, 87%). mp 190–192° C.

EXAMPLE 17

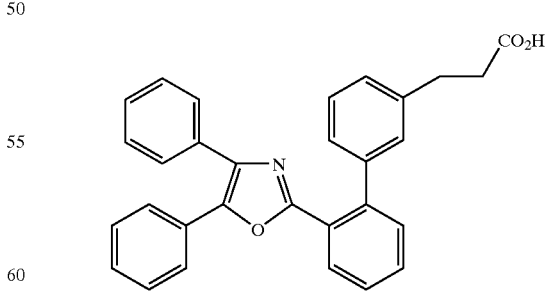

A slurry of Example 16 Part C compound (136 mg, 0.31 mmol) and 10% palladium on carbon (100 mg) in tetrahydrofuran (20 mL) was stirred under hydrogen atmosphere overnight. The reaction was filtered and concentrated. The residue was dissolved in ethyl acetate, washed with water and brine, dried over anhydrous MgSO4 and concentrated to give the title compound as a white solid (124 mg, 90%). mp 91–93° C.

EXAMPLE 18

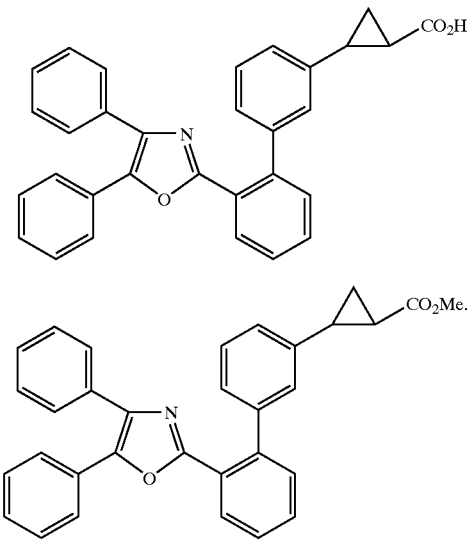

A

1-Methyl-3-nitro-1-nitrosoguanidine was added to a mixture of ether and aqueous potassium hydroxide solution at 0° C. The yellow ether layer was decanted into a flask containing solid potassium hydroxide cooled to 0° C. The ether was decanted into a solution of Example 16 Part B compound in dichloromethane at 0° C. Palladium acetate was added to this mixture and the reaction was stirred for 12 h. The reaction mixture was filtered through a pad of Celite 525 and the filtrate was concentrated to give a brown oil. The crude product was purified by flash chromatography on silica gel, eluting with 1:4 ethyl acetate/hexane to give title compound as a yellow oil (90 mg g, 92%).

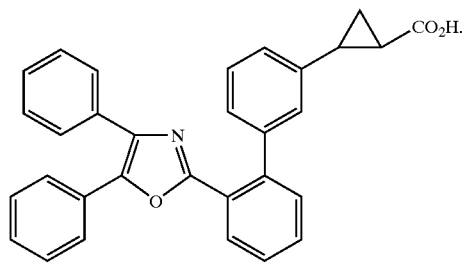

B

A solution of Part A (90 mg, 0.203 mmol) and lithium hydroxide (9 mg, 0.223 mmol) in tetrahydrofuran (5 mL) and water (5 mL) was stirred at room temperature overnight. Acidified with concentrated HCl to pH<7, extracted with ethyl acetate (3×20 mL). The combined organic layers were washed with water, and brine, then dried over MgSO$_4$ and concentrated. The crude product was purified by flash chromatography on silica gel, eluting with 4:6 ethyl acetate/hexane to give title compound as a white foam (82 mg, 88%).

EXAMPLE 19

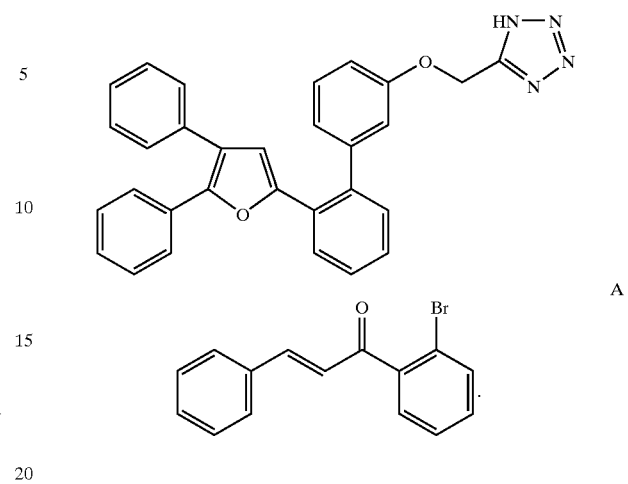

A

To a solution of 2'-bromoacetophenone (6.7 mL, 50 mmol) and potassium hydroxide (14.03 g, 150 mmol) in methanol (100 mL) was added benzaldehyde (15.3 mL, 150 mmol) at room temperature. The reaction mixture was stirred for 30 min, and poured into a mixture of acetic acid and water (1:2, 300 mL) at 0° C. The mixture was extracted with dichloromethane (3×100 mL). The combined organic layers were washed with saturated aqueous ammonium chloride solution, brine, then dried over anhydrous MgSO$_4$ and concentrated. The crude product was distilled under vacuum to remove benzaldehyde. The residue was purified by flash chromatography eluting with 9:11 dichloromethane/hexane to give title compound as a light yellow oil (10.4 g, 72%).

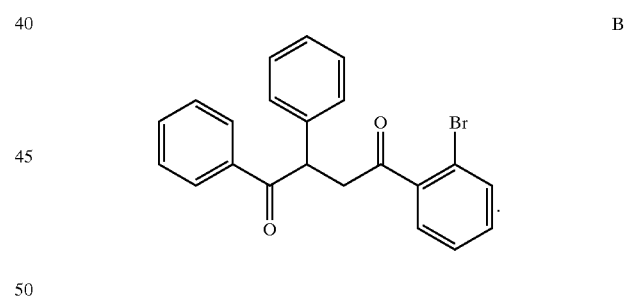

B

A solution of Part A compound (9.18 g, 31.9 mmol), benzaldehyde (3.4 mL, 33.5 mmol), triethylamine (2.6 mL, 18.5 mmol) and 3,4-dimethyl-5-(2-hydroxyethyl)thiazolium iodide (1.82 g, 6.4 mmol) in ethanol (45 mL) was refluxed for 40 hr. The orange red solution was evaporated under reduced pressure to remove ethanol. The residue was dissolved in dichloromethane (200 mL). The organic layer was washed with dilute HCl (1M, 200 mL), saturated aqueous sodium bicarbonate solution (200 mL), water, and brine, then dried over anhydrous MgSO$_4$ and concentrated. The orange red residue was purified by flash chromatography eluting with a step gradient of 50% to 66% dichloromethane in hexane to give title compound as a colorless oil (9.80 g, 78%).

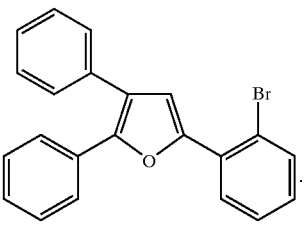

C

A solution of Part B compound (1.31 g, 3.34 mmol) and boron trifluoride diethyl etherate (0.42 mL, 3.34 mmol) in toluene (15 mL) was refluxed for 3 hr. The reaction mixture was cooled to room temperature and diluted with hexane (250 mL). The organic layer was washed with saturated aqueous sodium bicarbonate solution (200 mL), water, and brine, then dried over anhydrous MgSO$_4$ and concentrated. The light yellow oil was purified by flash chromatography eluting 1:9 dichloromethane/hexane to give title compound as a colorless oil (1.10 g, 88%).

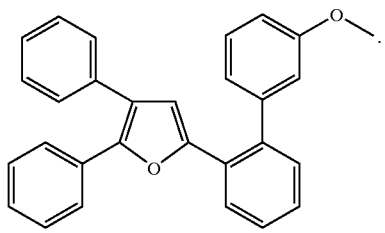

D

Nitrogen was bubbled through a solution of Part C compound (1.0 g, 2.66 mmol), 3-methoxy phenylboronic acid (526 mg, 3.46 mmol) and sodium carbonate (9.3 mL, 2M, 18.6 mmol) in toluene (7 mL) and ethanol (2.8 mL) at room temperature for 30 min. Tetrakis(triphenylphosphine)-palladium(0) (100 mg, 0.086 mmol) was added and the reaction mixture was stirred at 90° C. for 16 h under nitrogen. The reaction mixture was cooled to room temperature and extracted with ethyl acetate (2×50 mL). The combined organic layers were washed with brine, dried over anhydrous MgSO$_4$ and concentrated. The crude product was purified by flash chromatography eluting with 1:3 dichloromethane/hexane to give title compound as a white foam (1.01 g, 94%).

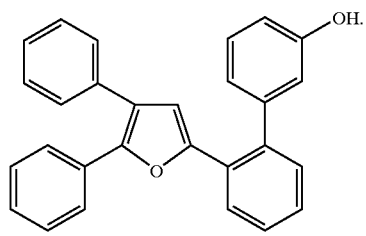

E

To a mixture of Part D compound (791 mg, 1.97 mmol) and lithium iodide (3.95 g, 29.5 mmol) was added dimethyl formamide (7 mL) at room temperature. The reaction mixture was refluxed at 170° C. overnight under argon, cooled to room temperature, diluted with water and extracted with ether (3×35 mL). The combined organic layers were washed with saturated aqueous sodium bicarbonate solution (80 mL), water, and brine, then dried over anhydrous MgSO$_4$ and concentrated. The crude product was purified by flash chromatography eluting with 1:3 ethyl acetate/hexane to give title compound as a white foam (651 mg, 85%).

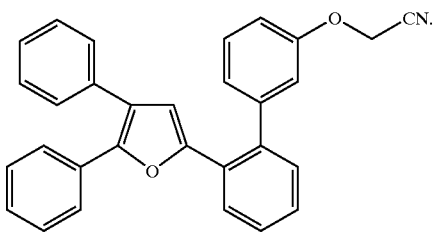

F

To a solution of Part E compound (368 mg, 0.95 mmol) in anhydrous dimethylformamide (2.5 mL) was added sodium hydride (38 mg, 60%, 0.95 mmol). The reaction was stirred at room temperature for 20 min followed by addition of bromoacetonitrile (0.10 mL, 1.44 mmol). The reaction mixture was stirred at 50° C. overnight, cooled to room temperature, diluted with water and extracted with ether (3×40 mL). The combined organic layers were washed with saturated aqueous sodium bicarbonate solution (80 mL), water, and brine, then dried over anhydrous MgSO$_4$ and concentrated. The crude product was purified by flash chromatography eluting with 1:9 dichloromethane/hexane to give title compound as a white foam (306 mg, 75%).

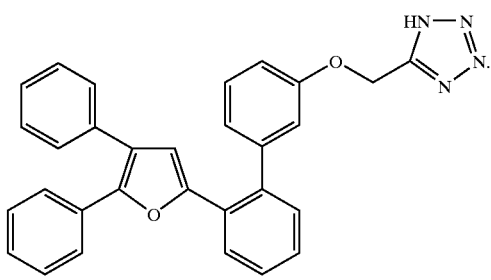

G

A solution of Part F compound (174 mg, 0.41 mmol) and azidotrimethyltin (126 mg, 0.61 mmol) in toluene (2 mL) was refluxed overnight. The reaction mixture was cooled to room temperature, methanol (5 mL) was added, stirred for 30 min, and concentrated. The residue was dissolved in dichloromethane (100 mL), washed with water, and brine, then dried over anhydrous MgSO$_4$ and concentrated. The crude product was purified by flash chromatography eluting with 1:9 methanol/ethyl acetate to give title compound as a white solid (110 mg, 57%).

EXAMPLE 20

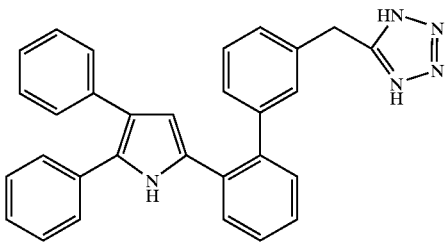

-continued

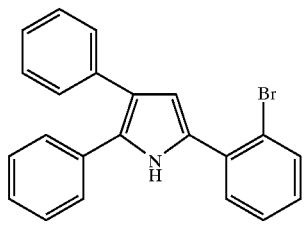

A

A solution of Example 19 Part B compound (787 mg, 2.0 mmol) and ammonium acetate (800 mg, 10.4 mmol) in acetic acid (5 mL) was refluxed, protected by a drying tube, for 3 hr. The reaction mixture was cooled to room temperature and poured slowly into aqueous saturated sodium bicarbonate and the reaction mixture was extracted with ethyl acetate. The organic layer was dried (MgSO$_4$) and concentrated. The crude product was purified by flash chromatography on silica gel, eluting with 11:39 dichloromethane/hexane, to give title compound as a white foam (508 mg, 68%).

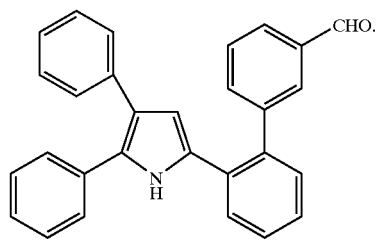

B

Nitrogen was bubbled through a solution of Part A compound (775 mg, 2.07 mmol), 3-formyl phenylboronic acid (405 mg, 2.7 mmol) and aqueous sodium carbonate (3.3 mL, 2 M, 6.6 mmol) in toluene (5.5 mL) and ethanol (2.2 mL) at room temperature for 30 min. Tetrakis(triphenylphosphine)-palladium(0) (80 mg, 0.07 mmol) was added and the reaction mixture was stirred at 80° C. for 14 hr under argon. The reaction mixture was cooled to room temperature and extracted with ethyl acetate twice. The combined organic extracts were washed with brine, dried (MgSO$_4$) and concentrated. The crude product was purified by flash chromatography on silica gel, eluting with 2:1 dichloromethane/hexane to give title compound as a white foam (598 mg, 72%).

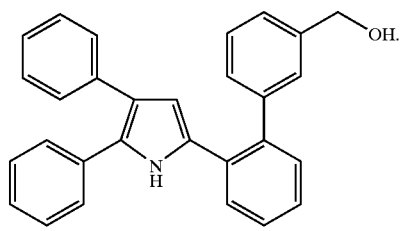

C

Lithium borohydride in tetrahydrofuran (0.5 mL, 2M, 1 mmol) was added slowly to a solution of Part B compound (495 mg, 1.24 mmol) in tetrahydrofuran (3 mL) at room temperature under argon. The reaction was stirred for 30 min, quenched cautiously with aqueous saturated sodium bicarbonate solution, stirred for 10 min and extracted with ethyl acetate. The organic extract was dried (MgSO$_4$) and concentrated. The residue was dissolved in dichloromethane and filtered through a pad of silica gel (25 g). The pad was washed with dichloromethane (200 mL). The filtrate was dried (MgSO$_4$) and concentrated to give the title compound as a white foam (490 mg, 98%).

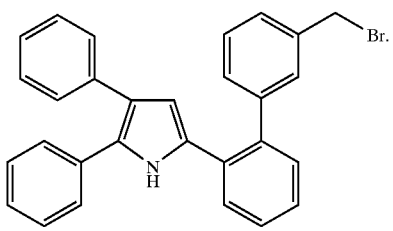

D

To a solution of Part C compound (214 mg, 0.53 mmol) and carbon tetrabromide (200 mg, 0.60 mmol) in dichloromethane (2 mL) was added triphenylphosphine (158 mg, 0.53 mmol) at room temperature. The solution was stirred for 1 hr, evaporated onto silica gel and purified by flash chromatography on silica gel, eluting with 3:7 dichloromethane/hexane to give the title compound (180 mg, 73%) as a light yellow foam.

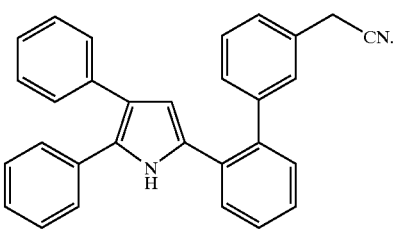

E

A solution of Part D compound (175 mg, 0.37 mmol) and sodium cyanide (200 mg, 0.60 mmol) in dimethylsulfoxide (1 mL) was stirred for 3 hr at 50° C. under argon. The reaction mixture was cooled to room temperature, diluted with water and filtered. The solid was washed with water and dried to give the title compound as an off-white solid (140 mg, 91%).

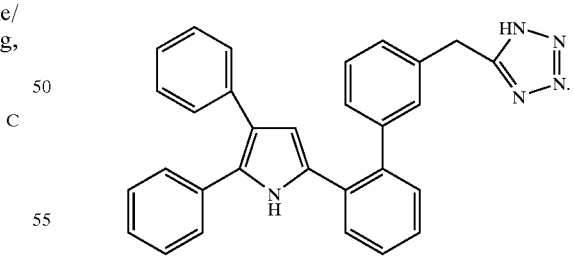

F

A solution of Part E compound (135 mg, 0.33 mmol) and azidotrimethyltin (100 mg, 0.49 mmol) in toluene (2 mL) was heated to 140° C. for 18 hr under argon. The reaction mixture was cooled to room temperature. After adding methanol (5 mL), the reaction was stirred for 30 min and concentrated. The crude product was purified by flash chromatography on silica gel, eluting with 1:5 methanol/dichloromethane to give title compound as a tan solid (105 mg, 70%).

EXAMPLE 21

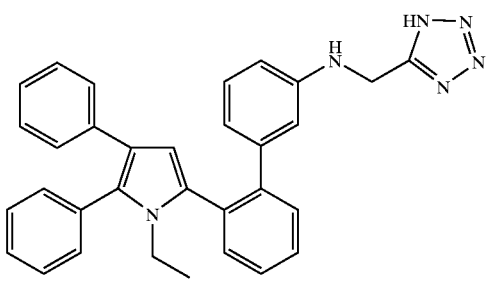

A

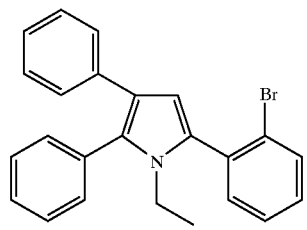

A solution of Example 19 Part B compound (1.164 g, 2.96 mmol), ethylamine hydrochloride (1.22 g, 15 mmol) and sodium acetate (1.23 g, 15 mmol) in acetic acid (10 mL) was refluxed for 52 h under argon. The reaction mixture was cooled to room temperature and added slowly to saturated aqueous sodium bicarbonate solution (100 mL). The mixture was extracted with dichloromethane (2×100 mL) and the combined organic layers were washed, dried (MgSO$_4$) and concentrated. The crude product was purified by flash chromatography eluting with 1:7 dichloromethane/hexanes to give title compound as a white foam (556 mg, 47%).

B

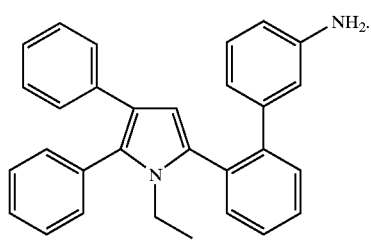

Nitrogen was bubbled through a solution of Part A compound (547 mg, 1.35 mmol), 3-amino phenylboronic acid (327 mg, 2.4 mmol) and aqueous sodium carbonate (3.0 mL, 2M, 6 mmol) in toluene (5 mL) and ethanol (2 mL) at room temperature for 30 min. Tetrakis(triphenylphosphine)-palladium(0) (55 mg, 0.05 mmol) was added and the reaction mixture was stirred at 80° C. for 14 h under argon. The reaction mixture was cooled to room temperature and extracted twice with ethyl acetate. The combined organic layers were washed with brine, dried (MgSO$_4$) and concentrated. The crude product was purified by flash chromatography eluting with 11:9 dichloromethane/hexanes to give title compound as a white foam (379 mg, 68%).

C

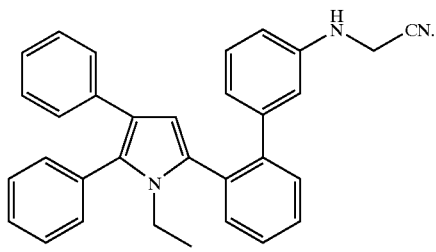

To a slurry of Part B compound (373 mg, 0.90 mmol) and potassium carbonate (200 mg, 1.4 mmol) in anhydrous DMF (2 mL) was added bromoacetonitrile (70 RL, 1.0 mmol). The reaction mixture was stirred at 50° C. overnight, cooled to room temperature, diluted with water, and extracted with ether(3×50 mL). The combined organic layers were washed with water and brine, then dried (MgSO$_4$) and concentrated. The crude product was purified by flash chromatography eluting with 3:7 dichloromethane/hexanes to give title compound as a colorless oil (174 mg, 43%).

D

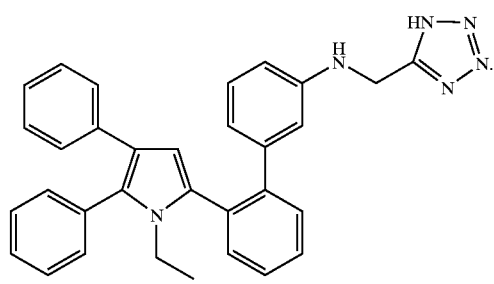

A solution of Part C compound (120 mg, 0.38 mmol) and azidotrimethyltin (100 mg, 0.5 mmol) in toluene (2 mL) was refluxed overnight under argon. The reaction mixture was cooled to room temperature, methanol (5 mL) was added, stirred for 1 hr, and concentrated to give crude title compound as a yellow oil (140 mg). A portion of the impure product (85 mg) was purified by preparative HPLC (C-18 reverse phase, eluting with methanol/0.1% aqueous TFA) to give the title compound (47 mg, 34%) as a white solid, mp 109–111° C.

EXAMPLE 22

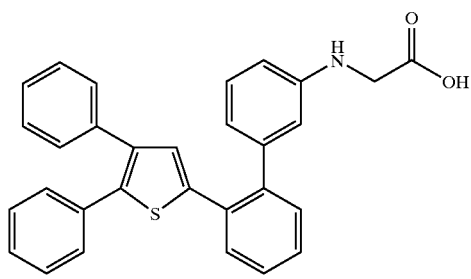

-continued

A

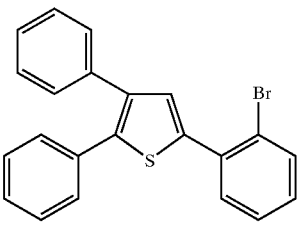

A solution of Example 19 Part B compound (3.26 g, 8.3 mmol) and Lawesson's reagent (7 g, 17 mmol) in toluene (15 mL) was refluxed for 24 hr under argon. Additional Lawesson's reagent (2 g, 4.94 mmol) was added and the solution was refluxed for an additional 24 hr. The reaction mixture was cooled to room temperature and diluted with ether. The organic layer was washed with saturated aqueous sodium bicarbonate solution, water and brine, then dried ($MgSO_4$) and concentrated. The crude product was purified by flash chromatography, eluting with 1:24 dichloromethane/hexanes to give title compound as a white solid (2.65 g) with the corresponding furan as an impurity (20%). The mixture was recrystallized from hexanes to give the product as a white solid (850 mg, 93% pure, 28% yield).

B

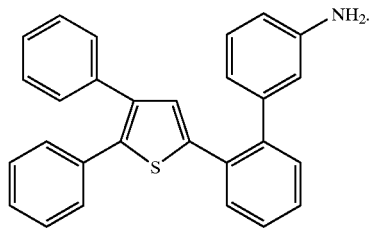

Nitrogen was bubbled through a solution of Part A compound (663 mg, 1.69 mmol), 3-aminophenylboronic acid (410 mg, 2.20 mmol) and aqueous sodium carbonate (3.7 mL, 2M, 7.4 mmol) in toluene (6 mL) and ethanol (2.5 mL) at room temperature for 30 min. Tetrakis (triphenylphosphine)-palladium(0) (67 mg, 0.06 mmol) was added and the reaction mixture was refluxed for 16 h under argon. The reaction mixture was cooled to room temperature, diluted with brine (10 mL) and extracted with ethyl acetate. The combined organic layers were washed with brine, dried ($MgSO_4$) and concentrated. The crude product was purified by flash chromatography, eluting with 3:1 dichloromethane/hexanes to give title compound as a white foam (680 mg, 100%).

C

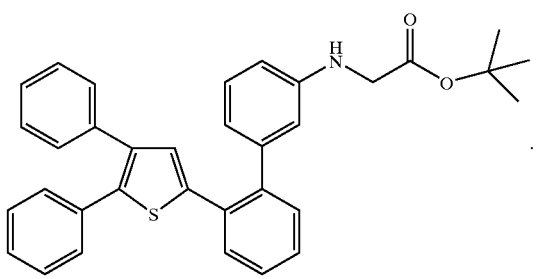

To a slurry of Part B compound (354 mg, 0.878 mmol) and potassium carbonate (250 mg, 1.8 mmol) in anhydrous DMF (3 mL) was added tert-butyl bromoacetate (130 μL, 0.88 mmol). The reaction mixture was stirred at 50° C. under argon overnight, cooled to room temperature, diluted with water and extracted with ether (3×20 mL). The combined organic layers were washed with water and brine, then dried ($MgSO_4$) and concentrated. The crude product was purified by flash chromatography eluting with 2:3 dichloromethane/hexanes to give title compound as a colorless oil (118 mg, 26%).

D

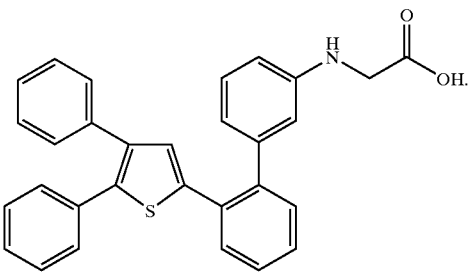

A solution of Part C compound (115 mg, 0.222 mmol) in trifluoroacetic acid (1 mL) and dichloromethane (1 mL) was stirred at room temperature for 14 h under argon. The reaction mixture was evaporated from ethanol (4 mL) twice. The residue was dissolved in ethyl acetate and hexane was added to give an oily product. The solvent was decanted and the product was dried under vacuum at 60° C. to give the title compound as a white foam (47 mg, 62%), 87% pure and containing 7.8% of the analogous furan.

EXAMPLE 23

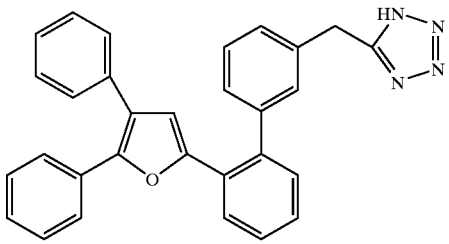

A

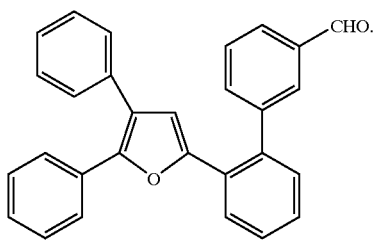

Nitrogen was bubbled through a solution of Example 19 Part C compound (1.0 g, 2.66 mmol), 3-formyl phenylboronic_acid (520 mg, 3.5 mmol) and aqueous sodium carbonate (9.3 mL, 2M, 18.6 mmol) in toluene (7 mL) and ethanol (2.8 mL) at room temperature for 30 min. Tetrakis(triphenyl-phosphine) palladium(0) (100 mg, 0.09 mmol) was added and the mixture was stirred at 80° C. for 14 hr under argon. The reaction mixture was cooled to room temperature and extracted with ethyl acetate (2×30 mL). The combined organic extracts were washed with brine, dried ($MgSO_4$) and concentrated. The crude product was purified by flash chromatography on silica gel, eluting with 1:3 dichloromethane/hexane to give title compound as a white foam (525 mg, 49%).

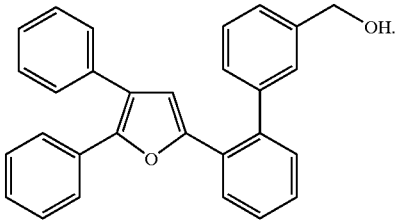

B

Lithium aluminum hydride in tetrahydrofuran (0.7 mL, 1M, 0.7 mmol) was added slowly to a solution of Part A compound (494 mg, 1.23 mmol) in tetrahydrofuran (3 mL) at room temperature under argon. The reaction was stirred for 15 min, quenched cautiously with aqueous potassium hydrogen sulfate solution (5%) and extracted with ethyl acetate. The organic layer was dried (MgSO$_4$) and concentrated to give the title compound as a white foam (471 mg, 95%).

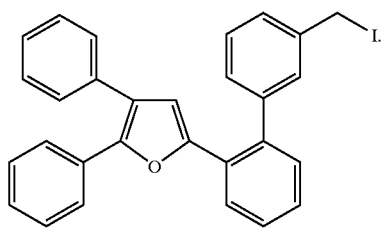

C

To a solution of Part B compound (465 mg, 1.15 mmol), triphenylphosphine (303 mg, 1.16 mmol) and imidazole (172 mg, 2.5 mmol) in tetrahydrofuran (5 mL) under argon was added a solution of iodine (293 mg, 1.15 mmol) in THF (1 mL) over 5 min. The reaction mixture was stirred for 10 min and then diluted with ethyl acetate. The organic layer was washed with sodium bisulfite solution (5%), dried (MgSO$_4$) and concentrated. The crude product was purified by flash chromatography on silica gel, eluting with hexane to give title compound as a colorless oil (304 mg, 51%).

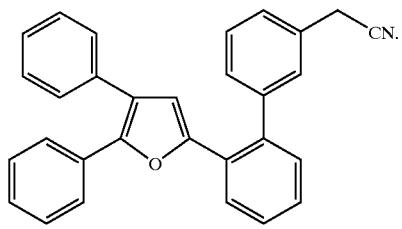

D

A solution of Part C compound (299 mg, 0.584 mmol) and potassium cyanide (300 mg, 4.6 mmol) in DMSO (3 mL) was stirred at 50° C. for 13 h. The reaction mixture was cooled to room temperature, diluted with water, and extracted with diethyl ether (3×20 mL). The organic layer was dried (MgSO$_4$) and concentrated to give the title compound as a yellow oil (193 mg, 80%).

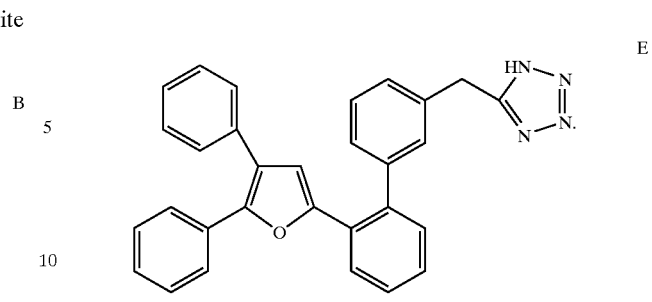

E

A solution of Part D compound (190 mg, 0.46 mmol) and azidotrimethyltin (140 mg, 0.68 mmol) in toluene (3 mL) was refluxed for 18 h under argon. The reaction mixture was cooled to room temperature, methanol (5 mL) was added and the mixture was stirred for 30 min. After evaporating the solvents, the crude product was recrystallized from ethyl acetate/hexane to give title compound as a white solid (77 mg, 37%), mp 188–190° C.

EXAMPLE 24

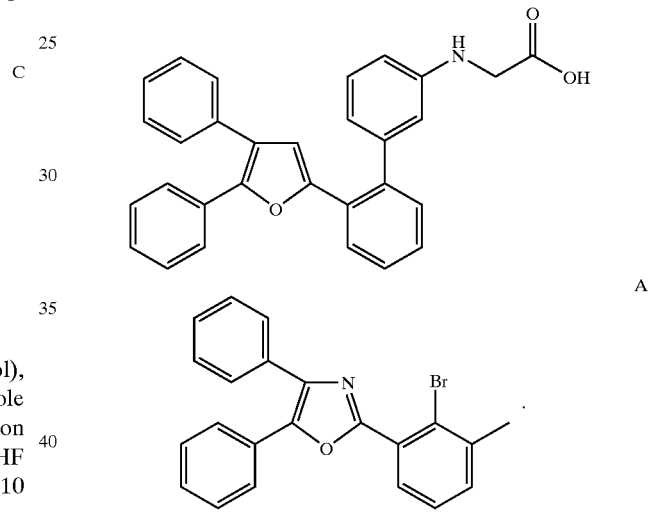

A

To a solution of 2-bromo-3-methyl benzoic acid (2.15 g, 10 mmol), 4-dimethyl amino pyridine (211 mg, 1.73 mmol) and benzoin (2.07 g, 9.56 mmol) in dichloromethane (30 mL) was added 1-(3-dimethylaminopropyl)-3-ethylcarbodiimide hydrochloride (2.09 g, 10.6 mmol) at room temperature. The resulting pale yellow solution was stirred for 48 hr, treated with HCl (20 mL, 0.5 N) and extracted with ethyl acetate (2×150 mL). The combined organic layers were washed with HCl (20 mL, 0.5 N), saturated sodium bicarbonate solution (20 mL), and brine (20 mL), dried over anhydrous MgSO$_4$ and concentrated. The crude product was purified by flash chromatography on silica gel, eluting with 5:95 ethyl acetate/hexane to give the ketoester as a colorless oil (2.83 g, 67%).

A mixture of crude ketoester (2.81 g, 6.9 mmol) and ammonium acetate (2.63 g, mmol) in glacial acetic acid (25 mL) was stirred at 110° C. for 4 h. The reaction mixture was concentrated to half the volume, cooled to 0° C. and diluted with water. The mixture was extracted with ethyl acetate (2×150 mL). The combined organic layers were washed with water (3×30 mL), saturated aqueous sodium bicarbonate solution (2×30 mL), and brine(30 mL), dried over anhydrous MgSO$_4$ and concentrated. The crude product was purified by flash chromatography on silica gel, eluting with 5:95 ethyl acetate/hexane to give title compound as a white solid (2.46 g, 91%). mp 83–85° C.

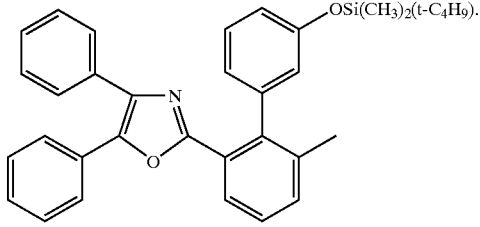

B

To a solution of Part A compound (500 mg, 1.28 mmol) in anhydrous tetrahydrofuran (7 mL) at −78° C. was added dropwise n-butyl lithium in hexane (600 μL, 2.5 N, 1.47 mmol). The reaction mixture was stirred for 15 min followed by addition of zinc bromide (330 mg, 1.47 mmol) in anhydrous tetrahydrofuran (3.3 mL). To this light green solution was added 1-(t-butyldimethylsilyloxy)-3-iodobenzene (428 mg, 1.37 mmol) in tetrahydrofuran (1 mL) followed by tetrakis(triphenylphosphine) palladium(0) (74 mg, 0.06 mmol). The reaction was stirred at −78° C. for 30 min and then at room temperature for 20 h. The reaction was quenched with aqueous ammonium chloride solution (5 mL, 25%) and extracted with diethyl ether (2×25 mL). The combined organic layers were washed with aqueous ammonium chloride solution (5 mL, 25%), brine (5 mL), dried over anhydrous MgSO$_4$ and concentrated. The crude product was purified by flash chromatography on silica gel, eluting 2:98 ethyl acetate/hexane to give title compound as a syrup (229 mg, 34.6%).

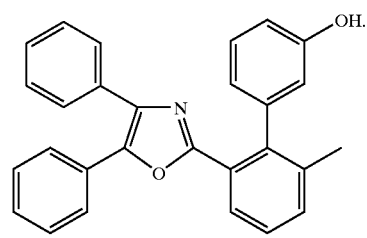

C

To a solution of Part B compound (229 mg, 0.44 mmol) in anhydrous tetrahydrofuran (4 mL) was added dropwise tetrabutylammonium fluoride in tetrahydrofuran (400 μL, 1 M, 0.4 mmol). The yellow solution was stirred at room temperature for 72 h, quenched with aqueous ammonium chloride solution (2 mL, 25%) and extracted with diethyl ether (2×25 mL). The combined organic layers were washed with aqueous ammonium chloride solution (2 mL, 25%), dried over anhydrous MgSO$_4$ and concentrated. The crude product was purified by flash chromatography on silica gel, eluting with a step gradient of 2:98 to 5:95 ethyl acetate/hexane to give title compound as a syrup (163 mg, 92%).

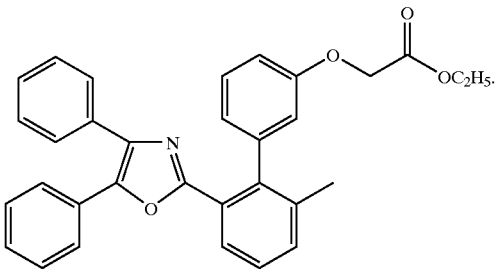

D

To a slurry of Part C compound (41 mg, 0.10 mmol) and potassium carbonate (25 mg, 0.18 mmol) in anhydrous dimethylformamide (0.5 mL) was added ethyl bromoacetate (15 μL, 0.14 mmol). The reaction mixture was stirred at room temperature for 20 h, diluted with ethyl acetate (20 mL). The organic layer was washed with water (3×1 mL), and brine (1 mL), then dried over anhydrous MgSO$_4$ and concentrated. The crude ester was used directly for the next step.

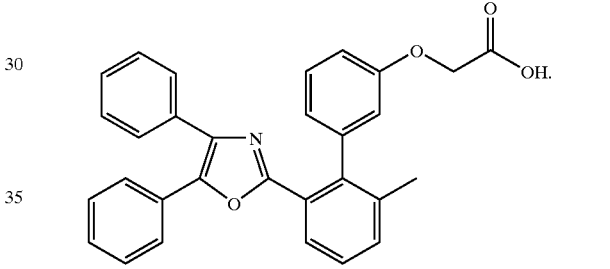

E

A solution of Part D (41 mg, 0.084 mmol) compound and sodium hydroxide solution (250 μL, 1N, 0.25 mmol) in methanol (1 mL) and water (1 mL) was stirred at room temperature for 1.5 h. The reaction mixture was concentrated, diluted with water and HCl (200 μL, 1N), extracted with ethyl acetate (2×10 mL). The combined organic layers were washed with water (2×1 mL), and brine (1 mL), dried over anhydrous MgSO$_4$ and concentrated to give the title compound as a beige foam (41 mg, 100%).

EXAMPLE 25

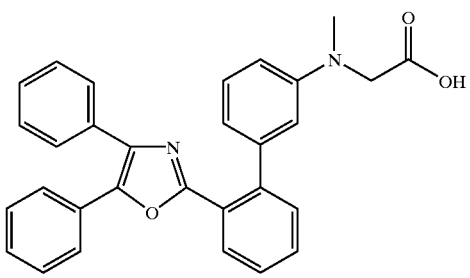

-continued

A

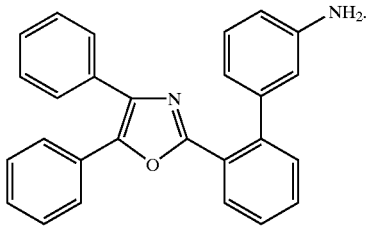

A solution of Example 1 Part A compound (1.25 g, 3.22 mmol) and tetrakis(triphenylphosphine) palladium(0) (117 mg, 0.10 mmol) in toluene (7.5 mL) was stirred for 10 min. 3-Aminophenyl boronic acid(637 mg, 3.96 mmol) was added to the solution followed by aqueous sodium carbonate (3.3 mL, 2M, 6.6 mmol). The reaction mixture was stirred at 80° C. for 20 hr under argon, cooled to room temperature and concentrated. The residue was partitioned between ethyl acetate (2×90 mL) and water (9 mL). The combined organic layers were washed with brine, dried over anhydrous MgSO$_4$ and concentrated. The crude product was purified by flash chromatography on silica gel, eluting with a step gradient of 1:9 to 1:4 ethyl acetate/hexane to give title compound as an oil (1.445 g, 100%).

B

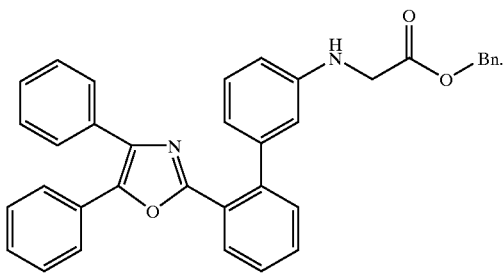

The mixture of Part A compound (1.445 g, 3.22 mmol), diisopropylethylamine (1.12 mL, 6.44 mmol), and benzylbromoacetate (610 µL, 3.7 mmol) in anhydrous dimethylformamide (15 mL) was stirred at room temperature for 17 hr. The reaction mixture was diluted with ethyl acetate (250 mL). The organic layer was washed with water (3×40 mL), brine (40 mL), dried over anhydrous MgSO$_4$ and concentrated. The crude product was purified by flash chromatography on silica gel, eluting with a step gradient of 1:9 to 1:4 ethyl acetate/hexane to give title compound as an oil (1.57 g, 91%).

C

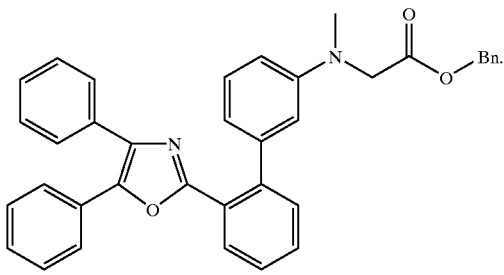

To a slurry of Part B compound (100 mg, 0.19 mmol) and potassium carbonate (26 mg, 0.19 mmol) in anhydrous dimethylformamide (1 mL) was added methyl iodide (17 µL, 0.28 mmol). The reaction mixture was stirred at room temperature for 16 h. Additional methyl iodide (60 µL, 0.99 mmol) was added and the reaction was stirred for 24 hr. Methyl iodide (40 µL, 0.66 mmol) was added again and the reaction was stirred for 20 hr. The reaction mixture was diluted with ethyl acetate (25 mL). The organic layer was washed with water (3×2 mL), and brine (2 mL), then dried over anhydrous MgSO$_4$ and concentrated. The golden oil was purified by flash chromatography on silica gel, eluting with 1:9 ethyl acetate/hexane to give title compound as colorless oil (73 mg, 70%).

D

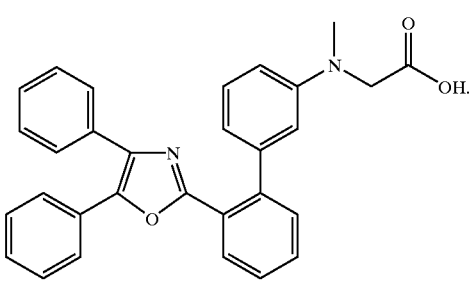

A suspension of Part C compound (73.5 mg, 0.13 mmol) and 20% palladium hydroxide on carbon (12.9 mg) in ethyl acetate (3 mL) was stirred under hydrogen atmosphere (1 atm) for 5 h. Additional catalyst (12 mg) was added and the reaction was stirred for 5 h. The reaction mixture was filtered through a pad of Celite® 525. The solids were washed with ethyl acetate (2×10 mL) and concentrated. The crude product was purified by flash chromatography on silica gel, eluting with a step gradient of 1:4 ethyl acetate/hexane to 95:5 dichloromethane/methanol to give title compound as a foam (14 mg, 24%).

EXAMPLE 26

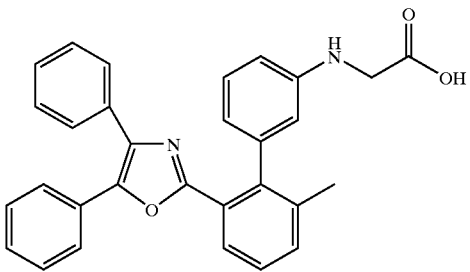

A

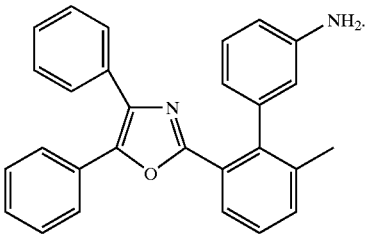

A solution of Example 24 Part A compound (700 mg, 1.79 mmol) and tetrakis(triphenylphosphine) palladium(0) (63 mg, 0.055 mmol) in toluene (4 mL) was stirred for 10 min.

3-aminophenyl boronic acid (344 mg, 2.15 mmol) was added to the solution followed by aqueous sodium carbonate (1.8 mL, 2M, 3.6 mmol). The reaction mixture was stirred at 80° C. for 20 h under argon, cooled to room temperature and concentrated. The residue was partitioned between dichloromethane (2×50 mL) and water (5 mL). The combined organic layers were washed with brine, dried over anhydrous MgSO₄ and concentrated. The crude product was purified by flash chromatography on silica gel, eluting with 1:9 ethyl acetate/hexane to give title compound as a white foam (623 mg, 86%).

B

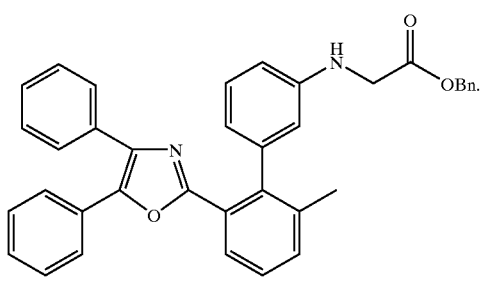

The mixture of Part A compound (300 mg, 0.72 mmol), diisopropylethylamine (0.25 mL, 1.44 mmol), and benzylbromoacetate (130 μL, 0.79 mmol) in anhydrous dimethylformamide (3 mL) was stirred at room temperature for 20 hr. The reaction mixture was diluted with ethyl acetate (100 mL). The organic layer was washed with water (2×10 mL), brine (10 mL), dried over anhydrous MgSO₄ and concentrated. The crude product was purified by flash chromatography on silica gel, eluting with a step gradient of 5:95 to 1:9 ethyl acetate/hexane to give title compound as a white foam (341 mg, 86%).

C

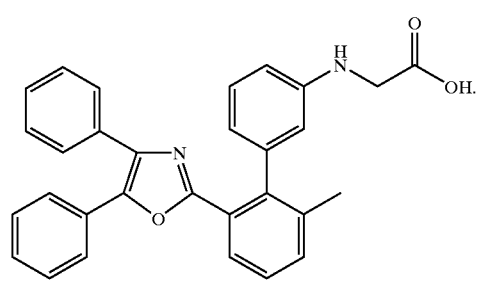

A suspension of Part B compound (311 mg, 0.56 mmol) and 20% palladium hydroxide on carbon (50 mg) in ethyl acetate (10 mL) was stirred under hydrogen atmosphere (1 atm) for 5 h. The reaction mixture was filtered through a pad of Celite® 525. The solids were washed with ethyl acetate (3×10 mL) and concentrated. The crude product was triturated with 1:5 dichloromethane/pentane (25 mL) to give the title compound as an off-white precipitate which was washed with pentane and dried (222 mg, 86%). mp 175–177° C.

EXAMPLE 27

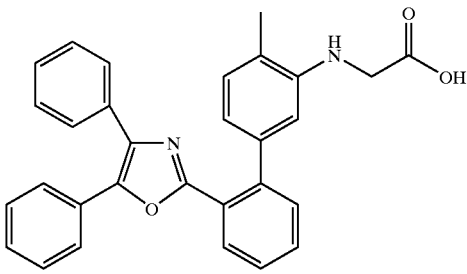

A

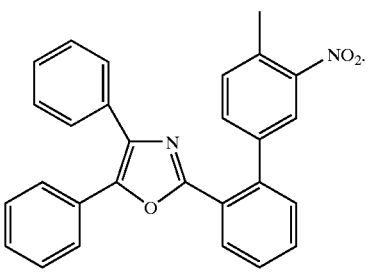

To a solution of 2-(3-nitro-p-toluyl)-benzoic acid (325 mg, 1.26 mmol), 4-dimethylaminopyridine (41 mg, 0.34 mmol) and benzoin (404 mg, 1.90 mmol) in dichloromethane (6 mL) was added 1-(3-dimethylaminopropyl)-3-ethylcarbodiimide hydrochloride (408 mg, 2.09 mmol) at room temperature. The resulting pale yellow solution was stirred for 16 h, treated with HCl (4 mL, 0.5 N) and extracted with ethyl acetate (2×30 mL). The combined organic layers were washed with HCl (4 mL, 0.5 N), saturated sodium bicarbonate solution (4 mL), and brine (4 mL), dried over anhydrous MgSO₄ and concentrated to give a light yellow oil.

A mixture of crude ketoester and ammonium acetate (500 mg, 6.49 mmol) in glacial acetic acid (5 mL) was stirred at 105° C. for 4 h. The reaction mixture was concentrated and extracted with ethyl acetate (2×50 mL). The combined organic layers were washed with water (3×12 mL), saturated aqueous sodium bicarbonate solution (2×12 mL), and brine (7 mL), dried over anhydrous Na₂SO₄ and concentrated. The crude product was purified by flash chromatography on silica gel, eluting with 5:95 ethyl acetate/hexane to give title compound as a white foam (265 mg, 48%). mp 108–110° C.

B

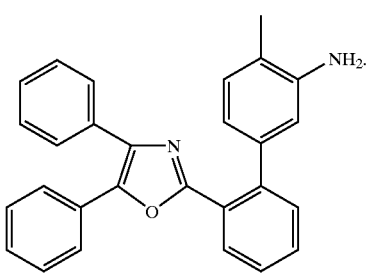

A suspension of Part A compound (265 mg, 0.61 mmol) and 20% palladium hydroxide on carbon (50 mg) in ethyl acetate (10 mL)) was stirred under hydrogen atmosphere (1 atm) for 41 h. The reaction mixture was filtered through a pad of Celite® 525. The solids were washed with ethyl acetate (3×10 mL) and concentrated. The crude product was purified by flash chromatography on silica gel, eluting with a step gradient of 5:95 to 1:9 ethyl acetate/hexane to give title compound as a white foam (259 mg, 100%).

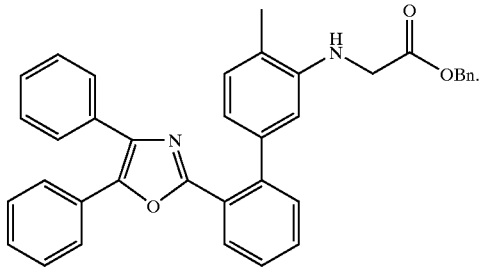
C

The mixture of Part B compound (255 mg, 0.63 mmol), diisopropylethylamine (0.22 mL, 1.26 mmol), and benzyl-bromoacetate (120 μL, 0.72 mmol) in anhydrous dimethyl-formamide (3 mL) was stirred at room temperature for 20 h. The reaction mixture was diluted with ethyl acetate (250 mL). The organic layer was washed with water (3×8 mL), brine (8 mL), dried over anhydrous MgSO$_4$ and concentrated. The crude product was purified by flash chromatography on silica gel, eluting with 1:9 ethyl acetate/hexane to give title compound as a white foam (226 mg, 65%).

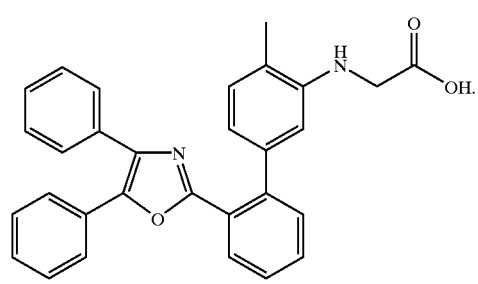
D

A suspension of Part C compound (226 mg, 0.41 mmol) and 20% palladium hydroxide on carbon (37 mg) in ethyl acetate (7.5 mL)) was stirred under hydrogen atmosphere (1 atm) for 5 h. The reaction mixture was filtered through a pad of Celite® 525. The solids were washed with ethyl acetate (3×10 mL) and concentrated. The crude product was triturated with 1:4 dichloromethane/hexane (25 mL) to get the title compound as a cream colored precipitate which was washed with hexane and dried (188 mg, 100%). mp 182–184° C.

EXAMPLE 28

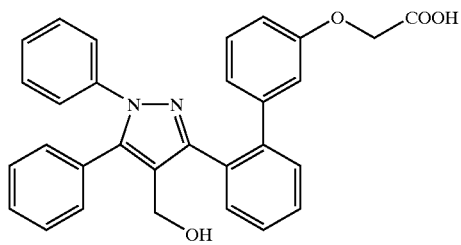

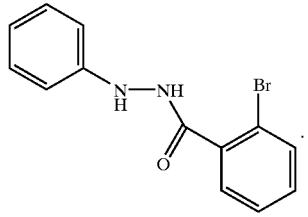
A

2-Bromobenzoyl chloride (15.2 mL, 0.118 mol) was added dropwise to a stirred solution of phenyl hydrazine (11.6 mL, 0.118 mol) and triethylamine (16.0 mL, 0.115 mol) in ether (400 mL) at 0° C. over 30 min. The reaction was warmed to room temperature. The solids formed were filtered and washed with ether thrice. The solids were dissolved in dichloromethane washed with water, and brine, dried over anhydrous MgSO4 and concentrated. The crude was recrystalized from ethyl acetate to get the title compound (12.1 gm, 35%)

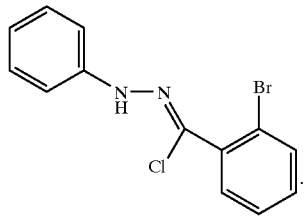
B

A solution of Part A compound (5 gm, 17.2 mmol) and phosphorus pentachloride (4.22 gm, 19.3 mmol) in ether (100 mL) was refluxed for 19 hr. The reaction mixture was cooled to room temperature and treated with a solution of phenol (7.38 gm, 78.4 mmol) in ether (10 mL). After 10 min, methanol (7.3 mL) was added, the mixture was stirred for 5 min and concentrated. The residue was purified by flash chromatography on silica gel eluting with 10% EtOAc in hexane to give title compound as a light brown 0:1 (2.07 g, 39%).

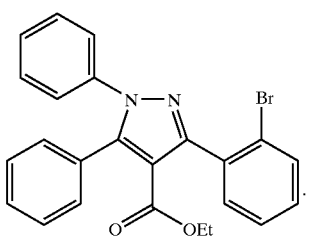
C

A solution of Part B compound (2.0 gm, 6.46 mmol) in absolute ethanol (9.4 mL) was added to a solution of ethylbenzoyl acetate (1.26 mL, 6.55 mmol) and 21% sodium ethoxide in ethanol (2.09 mL, 6.44 mmol) in absolute ethanol (12.6 mL). The reaction was stirred at room temperature for 4 h, quenched with 2N HCl (7.5 mL) and concentrated. The residue was triturated with ether. The organic layer was washed with water, and brine, dried over anhydrous MgSO4 and concentrated. The residue was purified by flash chromatography on silica gel eluting with a step gradient of 5% to 10% EtOAc in hexane to give the title compound as a thick oil (1.1 g, 38%).

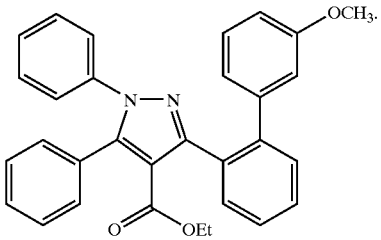

D

Nitrogen was bubbled through a solution of Part C compound (1.145 g, 2.56 mmol), 3-methoxyphenyl boronic acid (478 mg, 3.15 mmol) and aqueous sodium carbonate (2.6 mL, 2M, 5.2 mmol) in toluene (6 mL) and ethanol (2.6 mL) at room temperature for 15 min. Tetrakis (triphenylphosphine) palladium(0) (93 mg, 0.08 mmol) was added and the mixture was stirred at 80° C. for 20 h under argon. The reaction mixture was cooled to room temperature, diluted with water and extracted with ethyl acetate. The combined organic extracts were washed with brine, dried over anhydrous MgSO4 and concentrated. The crude product was purified by flash chromatography on silica gel, eluting with a step gradient of 5% to 10% ethyl acetate in hexane to give the title compound (1.215 g, 100%).

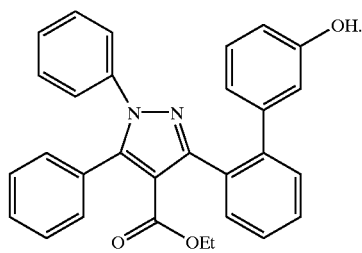

E

To a solution of Part D compound (948 mg, 1.99 mmol) in dry dichloromethane (10 mL) at 0° C. was added boron tribromide in dichloromethane (1M, 4.1 mL, 4.1 mmol). The reaction was stirred at 0° C. for 3 h and the at room temperature overnight. The mixture was diluted with water followed by 1N HCl and extracted with ethyl acetate. The combined organic extracts were washed with brine, dried over anhydrous MgSO4 and concentrated. The crude product was purified by flash chromatography on silica gel, eluting with a step gradient of 10% to 50% ethyl acetate in hexane to give title compound (688 mg, 75%).

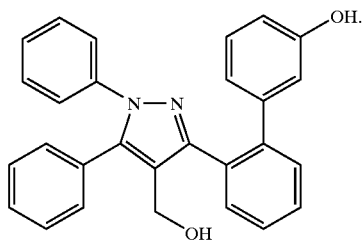

F

A solution of Part E compound (670 mg, 1.45 mmol) in anhydrous ether (3.6 mL) was added to a slurry of lithium aluminium hydride (114 mg, 2.85 mmol) in anhydrous ether (6 mL) at 0° C. The reaction was stirred at 0° C. for 3 h and at room temperature for 4 h. Anhydrous THF (10 mL) was added to the reaction mixture and it was stirred for 4 h. The reaction was cooled to 0° C. and quenched with 10% HCl and extracted with ethyl acetate. The combined organic extracts were washed with brine, dried over anhydrous MgSO4 and concentrated. The crude product was purified by flash chromatography on silica gel, eluting with a step gradient of 10% to 20% to 50% ethyl acetate in hexane to give the title compound (474 mg, 78%).

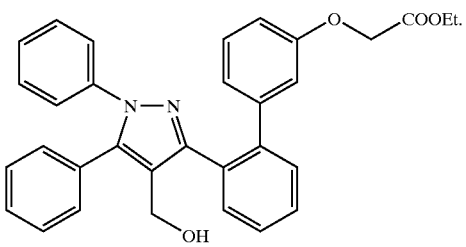

G

To a slurry of Part F compound (472 mg, 1.13 mmol) and potassium carbonate (180 mg, 1.3 mmol) in anhydrous dimethylformamide (5 mL) was added ethyl bromoacetate (150 µL, 1.3 mmol). The reaction mixture was stirred at room temperature for 48 h, diluted with ethyl acetate and water. The organic layer was washed with water and brine, then dried over anhydrous MgSO$_4$ and concentrated. The crude was purified by flash chromatography on silica gel, eluting with a step gradient of 25% to 33% ethyl acetate in hexane to give the title compound as an oil (410 mg, 74%).

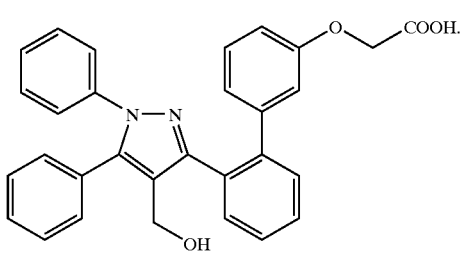

H

A solution of Part G compound (60 mg, 0.12 mmol) in aqueous sodium hydroxide (350 µL, 1N, 3.5 mmol) and methanol (1.4 mL) was heated to 50° C. for 3 h. The reaction mixture was concentrated and the residue was diluted with water. The pH was adjusted to 1 with 1N HCl. The mixture was extracted with ethyl acetate. The combined organic layers were washed with brine, dried over anhydrous MgSO$_4$ and concentrated to give title compound as a foam (63.8 mg, 100%).

EXAMPLE 29

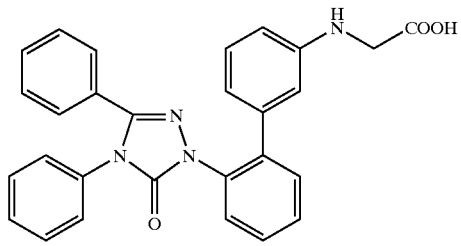

-continued

A

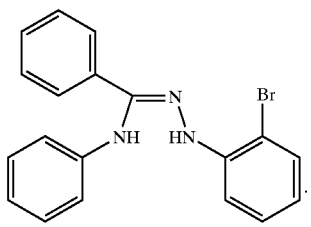

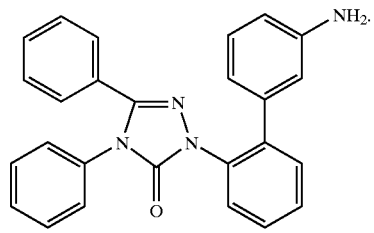

Following the same experimental procedure as in Example 28 Part D, coupling between Part B compound and 3-amino phenyl boronic acid afforded the title compound (yield 99%).

D

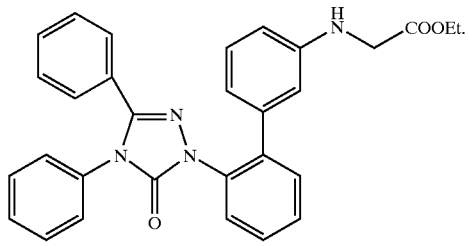

A solution of

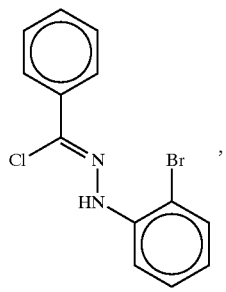

Following the same experimental procedure as in Example 28 Part G, alkylation of Part C compound with ethyl bromoacetate afforded the title compound (yield 34%).

E

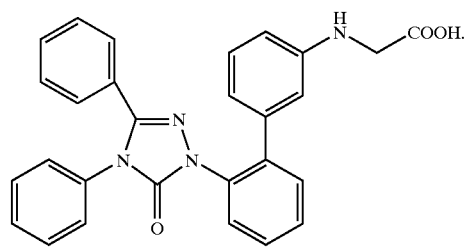

generated in analogy to the procedure used in Example 28 Part B, (2 g, 6.46 mmol) in anhydrous benzene (10 mL) was added to a solution of aniline (650 μL, 7.13 mmol) and triethyl amine (970 μL, 6.96 mmol) in anhydrous benzene (10.8 mL) at 50° C. The reaction was stirred at 50° C. for 3 hrs and concentrated. The residue was partitioned between water and ethyl acetate. The organic layer was washed with brine, dried over anhydrous MgSO4 and concentrated. The crude product was purified by flash chromatography on silica gel, eluting with 5% ethyl acetate in hexane to give title compound (1.328 g, 57%).

B

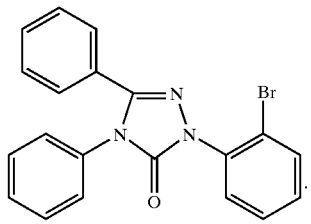

Following the same experimental procedure as in Example 28 Part H, hydrolysis of Part D compound afforded the title compound (yield 90%).

EXAMPLE 30

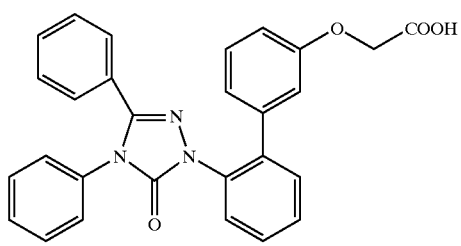

A solution of Part A compound (200 mg, 0.55 mmol) and triphosgene (248 mg, 0.82 mmol) in pyridine (600 μL) was heated to 160° C. in a sealed tube for 1 min. The reaction was cooled to room temperature and partitioned between water and ethyl acetate. The organic layer was washed with brine, dried over anhydrous MgSO4 and concentrated. The crude product was purified by flash chromatography on silica gel, eluting with 25% ethyl acetate in hexane to give title compound (203 mg, 94%).

-continued

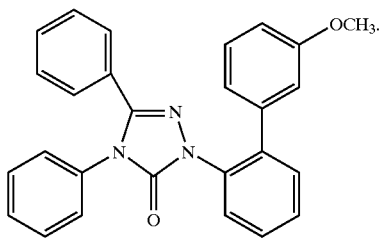

A

Following the same experimental procedure as in Example 28 Part D, the Suzuki coupling between Example 29 Part B compound and 3-methoxy phenyl boronic acid afforded the title compound (yield 87%).

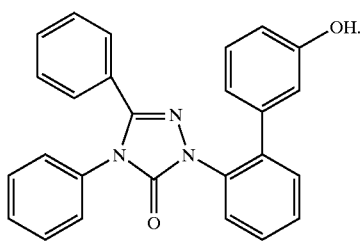

B

Following the same experimental procedure as in Example 28 Part E, Part A compound was treated with boron tribromide to afford the title compound (yield 73%).

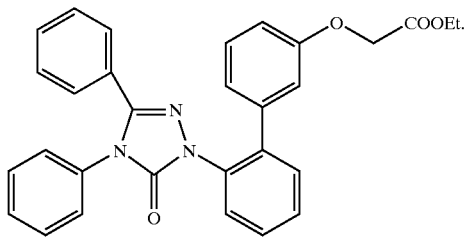

C

Following the same experimental procedure as in Example 28 Part G, alkylation of Part B compound with ethyl bromoacetate afforded the title compound (yield 96%).

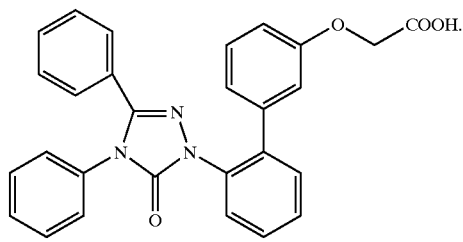

D

Following the same experimental procedure as in Example 28 Part H, hydrolysis of Part C compound afforded the title compound as a white solid (yield 98%).

EXAMPLE 31

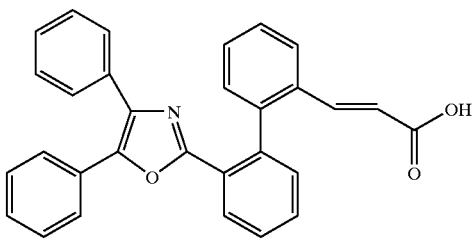

A

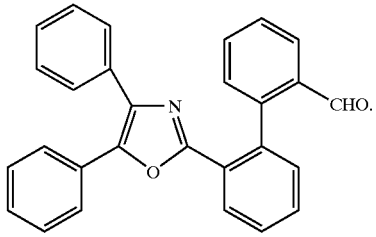

Example 1 Part A compound was coupled with 2-formyl-phenyl boronic acid by Suzuki coupling procedure described in Example 1 Part B to give the title compound in 84% yeild.

B

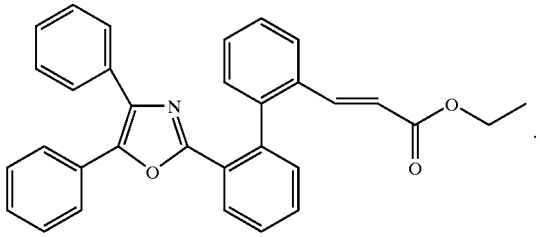

Triethyl phosphonoacetate (0.27 mL, 1.37 mmol) was added dropwise to a stirred suspension of sodium hydride (33 mg, 1.37 mmol) in THF (2 mL). The mixture was stirred for 1 hr, followed by dropwise addition of Part B compound (500 mg, 1.24 mmol) in THF(2 mL). The resulting yellow solution was stirred at room temperature overnight. Additional sodium hydride (20 mg, 0.83 mmol) was added and the reaction was stirred for 1 h. The reaction was diluted with water (50 mL) and ether(30 mL). The aqueous layer was extracted with ether twice. The combined organic layers were washed with brine dried over MgSO4 and concentrated to give the title compound (528 mg, 90%) which was used without purification in the next step.

C

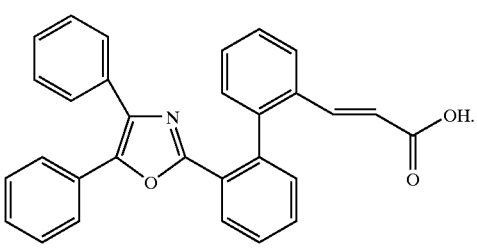

A mixture of Part B compound (100 mg, 0.212 mmol) in THF (1 mL) was treated with 1N NaOH solution (0.424 mL, 0.424 mmol). After refluxing overnight, the mixture was concentrated, and diluted with ethyl acetate/water. The reaction mixture was acidified with 1N HCl to pH of 1. The resulting light yellow precipitate was filtered, washed with hexane and water. The solid was purified by flash chromatography on silica gel eluting with 1:1 hexane:ethyl acetate to give title compound (42 mg, 45%).

EXAMPLE 32

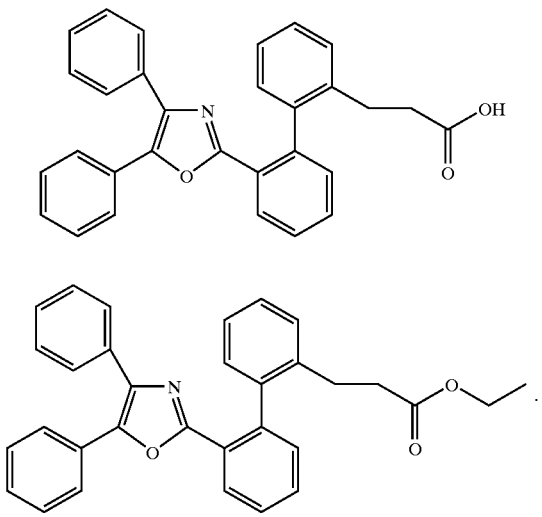

A

A suspension of Example 31 Part B compound (100 mg, 0.212 mmol) and 20% palladium on carbon (20 mg) in methanol was stirred under hydrogen (1 atm) overnight. The reaction mixture was filtered through a pad of Celite(545 and the filtrate was concentrated. The residue was purified by flash chromatography on silica gel eluting with a step gradient of 5% to 10% EtOAc in hexane to give title compound (92 mg, 92%).

B

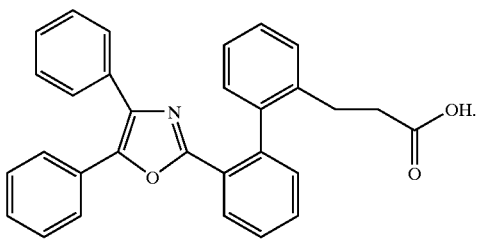

A mixture of Part A compound (90 mg, 0.190 mmol) in THF (0.5 mL) was treated with 1N NaOH solution (0.380 mL, 0.380 mmol). After stirring overnight at RT, the mixture was concentrated, diluted with water. The reaction mixture was acidified with 1N HCl to pH of 1. The tan precipitate was filtered, washed with hexane and water. The solid was dried to give the title compound (60 mg, 71%).

EXAMPLE 33

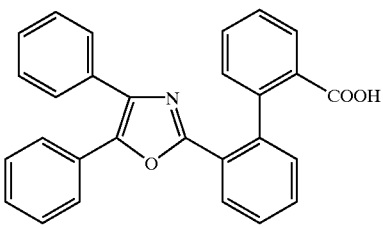

To a solution of Example 31 Part A compound (200 mg, 0.49 mmol) in THF (1.5 mL) and water (0.5 mL) at 0° C. was added sulfamic acid (48 mg, 0.49 mmol) and sodium chlorite (45 mg, 0.49 mmol). The reaction was stirred for 1.5 h and diluted with ether. The organic layer was washed with water, brine, dried over anhydrous MgSO4 and concentrated. The crude material was purified by preparative reverse phase HPLC to give the title compound (65 mg, 31%).

EXAMPLE 34

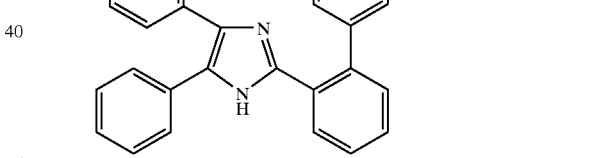

A

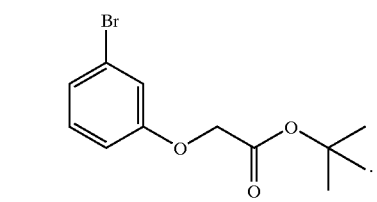

A mixture of 3-bromophenol (20 g, 116 mmol), $K_2CO_3$ (31.95 g, 231.2 mmol) and DMF (120 mL) was treated with tert-butyl bromoacetate (20 mL, 231 mmol) and the mixture stirred for 16 h. The reaction was concentrated and the residue was dissolved in ethyl actate. The organic fraction was washed with water, brine, dried (MgSO4) and concentrated. The residue was purified by flash column chromatography on silica gel eluting with 5% ethyl acetate in hexane to give the title compound as a colorless oil (30 g, 100%).

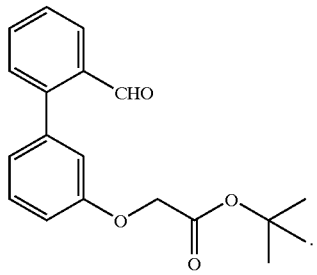
B

Part A compound was coupled with 2-formyl phenyl boronic acid by Suzuki coupling procedure described in Example 5 Part C to give the title compound in 69% yeild.

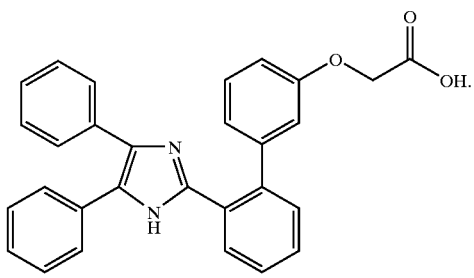
C

A mixture of benzil (5.5 g, 26.4 mmol) and ammonium acetate (12.94 g, 168 mmol) in glacial acetic acid (120 mL) was treated with Part B compound (7.5 g, 24.0 mmol) and stirred at 120° C. for 15 h. The reaction mixture was cooled, poured in water (300 mL) and precipitate was filtered. The solid was washed with hexane and dried to give the title compound as an off-white solid (12 g, 100%).

EXAMPLE 35

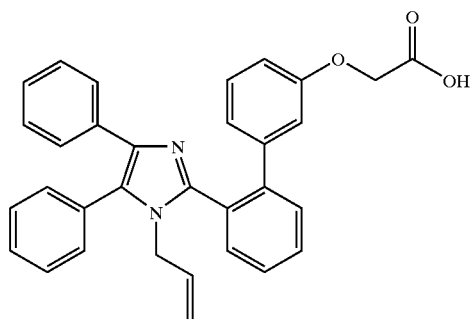

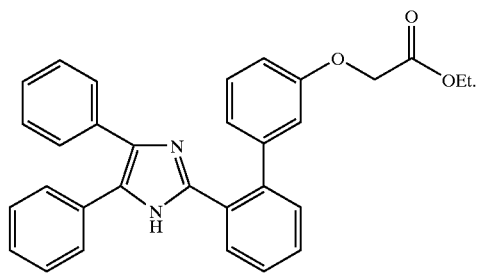
A

A solution of Example 34 compound (11.5 g, 22.8 mmol) in ethanol (300 mL) and sulfuric acid (3 mL) was stirred at room temperature overnight. The reaction was concentrated, diluted with ethyl acetate and neutralized with aqueous sodium carbonate solution. The organic layer was washed with water, aqueous sodium carbonate, and brine, dried over anhydrous MgSO4 and concentrated. The crude was triturated with hexane and ether to give the title compound as a light yellow solid (9.13 g, 84%).

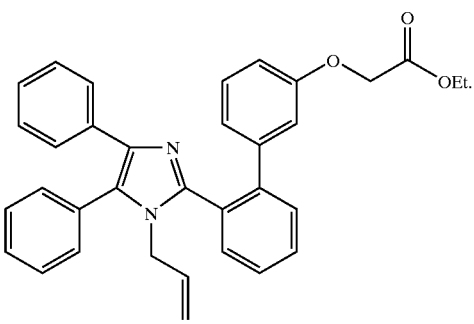
B

A mixture of Part A compound (0.100 g; 0.210 mmol), K2CO3 (0.058 g; 0.421 mmol) and DMF (1 mL) was treated with allyl bromide (20 µL, 0.231 mmol) and the mixture stirred for 16 h. Additional allyl bromide (20 µL, 0.023 mmol) was added. The mixture was stirred for 2 h. The mixture was diluted with equal amounts of ethyl acetate and water. The organic fraction was washed with water, brine, dried (MgSO4) and concentrated. The residue was purified by flash column chromatography with a step gradient of 10% to 20% ethyl acetate in hexane to give the title compound as a colorless oil. (0.095 g, 88%).

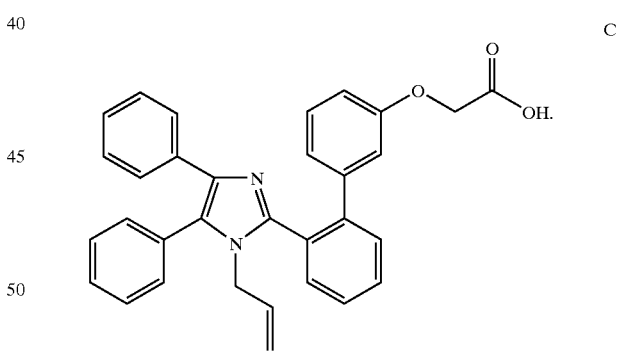
C

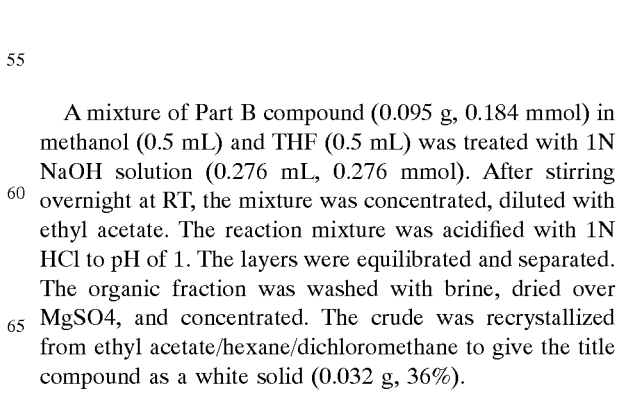

A mixture of Part B compound (0.095 g, 0.184 mmol) in methanol (0.5 mL) and THF (0.5 mL) was treated with 1N NaOH solution (0.276 mL, 0.276 mmol). After stirring overnight at RT, the mixture was concentrated, diluted with ethyl acetate. The reaction mixture was acidified with 1N HCl to pH of 1. The layers were equilibrated and separated. The organic fraction was washed with brine, dried over MgSO4, and concentrated. The crude was recrystallized from ethyl acetate/hexane/dichloromethane to give the title compound as a white solid (0.032 g, 36%).

EXAMPLE 36

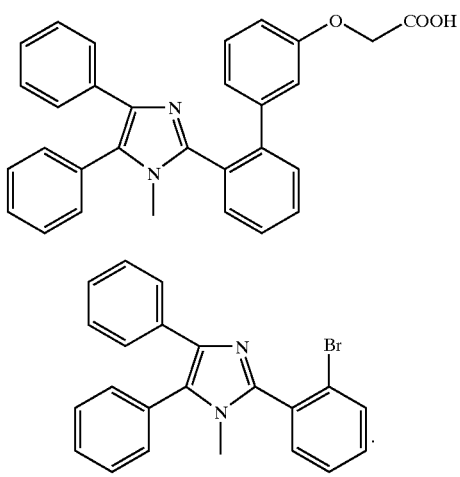

A mixture Example 5 Part A compound (3.75 g; 10.0 mmol) and sodium hydride (0.24 g, 10.0 mmol) in 35 mL of THF was stirred at RT for 15 min. The anion was slowly treated with methyl iodide (1.42 g, 10.0 mmol) and stirred overnight. The mixture was diluted with equal amounts of water and ethyl acetate. The layers were equilibrated. The organic fraction was washed with water (2×20 mL), brine, dried over MgSO4 and concentrated under vaccuum to give a white solid. The solid was recrystalized from hot methanol to give 2 g of product. The mother liquor was concentrated and recrystalized from methanol and a trace of water to give 1 g of additional material. The white solid was combined to give the title compound (3 g, 77%).

B

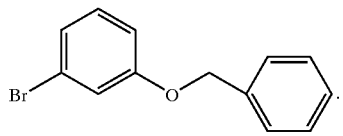

A mixture of 3-bromophenol (5 g, 29.0 mmol), potassium carbonate (4.0 g, 29.0 mmol) and benzyl bromide (4.87 g, 28.5 mmol) in 40 mL of DMF was stirred at RT for 18 hr. The mixture was diluted with water, the pH adjusted to 12 with KOH (pellets) and a white solid formed. The solid was triturated with water, filtered and washed with water to give the title compound (7.20 g, 96%).

C

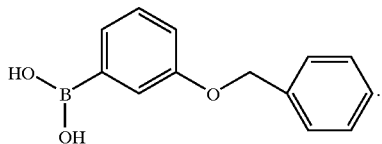

A mixture of Part B compound (3.20 g, 12.16 mmol) in 24 mL of THF at −78° C. was treated with n-butyllithium (5.8 mL, 14.6 mmol). After 1 h at −78° C. the anion was slowly treated with triisopropyl borate (2.28 g, 12.18 mmol) and the mixture warmed to RT. The mixture was diluted with a 3% acetic acid/water solution (60 mL). The mixture was stirred for 40 min. and the solid which formed was collected. The solid was triturated with a small volume of 5% ethyl acetate/hexane to give the title compound as a white powder (0.5 g, 18%).

D

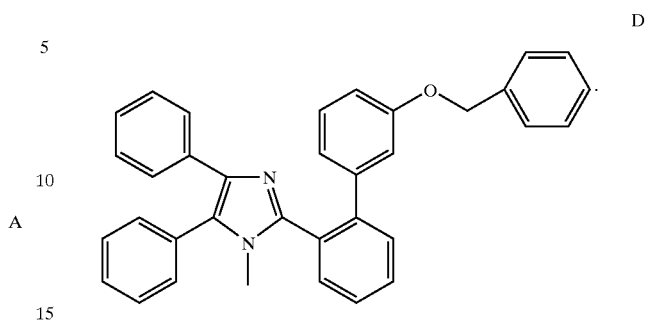

Following the general experimental procedure as in Example 8 Part A, Suzuki coupling between Part A and Part C compound afforded the title compound (yield 60%).

E

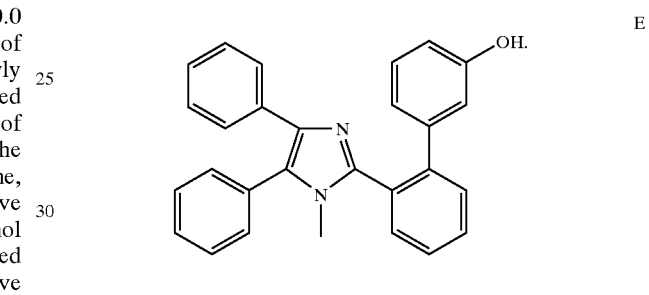

A mixture of Part D compound (0.50 g, 1.0 mmol) in ethanol (7 mL) was degassed and treated with 100 mg of 10% Pd on carbon. The mixture was put under an atmosphere of hydrogen gas (balloon pressure) and stirred overnight. The mixture was filtered and the colorless solution was mixed with 100 mg of Pearlman's catalyst and placed under an atmosphere of hydrogen for 4 h. The reaction was filtered and the filtrate concentrated to an oil. The oil was used without further purification.

F

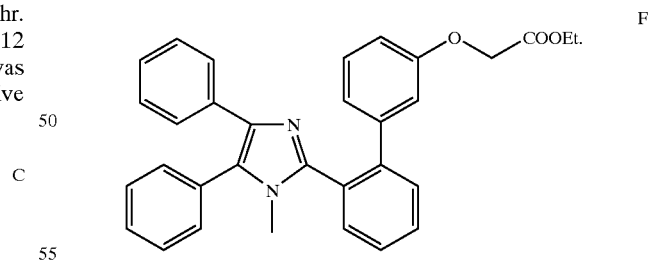

A mixture of the crude Part E compound (1 mmol), K2CO3 (0.138 g, 1.0 mmol) and ethyl bromoacetate (0.14 g, 0.8 mmol) in dimethyl formamide (3 mL) was stirred at RT overnight. The contents were diluted with equal amounts of water and ethyl acetate. The organic fraction was dried (MgSO4) and concentrated to provide a thick oil. The oil was purified on silica gel by flash column chromatography with 15% ethyl acetate:hexanes to give 0.28 g of crude material. The material was rechromatographed on silica with 7% ethyl acetate/dichloromethane to give the title compound (0.18 g, 36%).

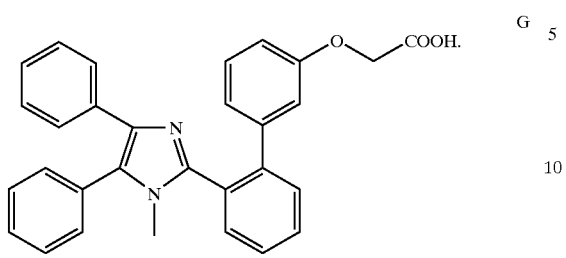

G

The Part F compound (0.18 g, 0.36 mmol) was dissolved in ethanol (2 mL) and treated with 1N NaOH (2 mL, 2 mmol). After 18 h at RT the mixture was acidified with citric acid until a pH of 3 was achieved. The mixture was diluted with equal volumes of ethyl acetate and water. The layers were equilibrated and the organic fraction dried (Na2SO4) and concentrated to give the title compound as a (0.17 g, 100%).

EXAMPLE 37

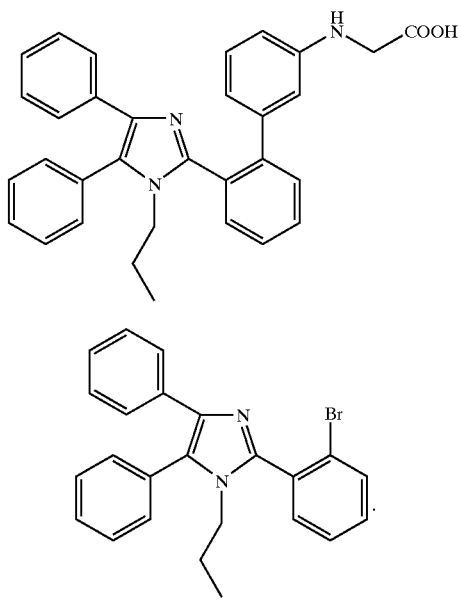

A

A mixture of Example 5 Part A compound (0.75 g, 2 mmol) in 5 mL of DMF at RT was treated with K$_2$CO (0.28 g, 2 mmol) and n-propyl iodide (0.3 mL, 3 mmol). The mixture was stirred for 18 h and poured into water. The water fraction was decanted from the thick residue. The residue was triturated with EtOH/water and the remainder was dried under vacuum to give the title compound as a white foam (380 mg, 50%).

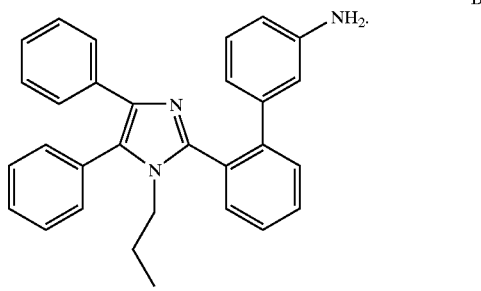

B

Nitrogen was bubbled through a solution of Part A compound (350 mg, 0.84 mm ol), 3-amino phenyl boronic acid (172 mg, 1.26 mmol) and aqueous sodium carbonate (840 µL, 2M, 1.68 mmol) in toluene (1.3 mL) and ethanol (700 µL) at room temperature for 15 min. Tetrakis (triphenylphosphine) palladium(0) (50 mg, 0.04 mmol) was added and the mixture was stirred at 80° C. for 36 h under argon. The reaction mixture was cooled to room temperature and extracted with ethyl acetate. The combined organic extracts were washed with brine, dried over anhydrous MgSO$_4$ and concentrated. The crude product was purified by flash chromatography on silica gel, eluting with 35:65 ethyl acetate/hexane to give title compound (310 mg, 88%).

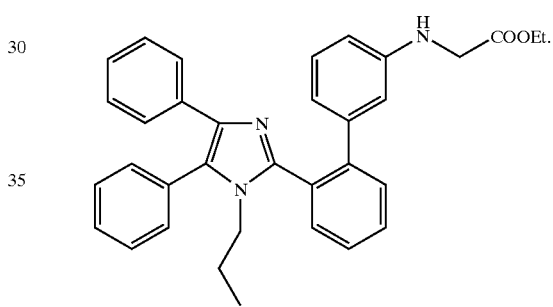

C

To a slurry of Part B compound (680 mg, 1.57 mmol) and potassium carbonate (420 mg, 3 mmol) in anhydrous dimethylformamide (3 mL) was added ethyl bromoacetate (250 mg, 1.50 mmol). The reaction mixture was stirred at room temperature for 18 h. The reaction was partitioned between diethyl ether and aqueous sodium bicarbonate solution. The organic layer was washed with water, and brine, then dried over anhydrous MgSO$_4$ and concentrated. The crude product was purified by flash chromatography eluting with 3:7 ethyl acetate/hexane to give title compound (450 mg, 55%).

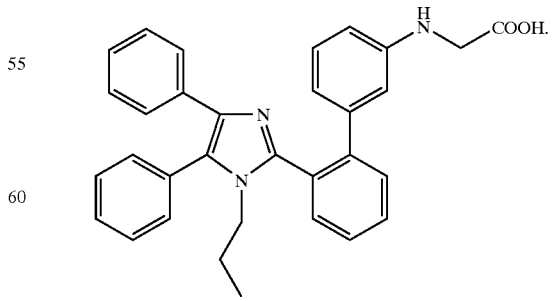

D

A mixture of Part C compound (0.35 g, 0.67 mmol) in methanol (3 mL) was treated with 1M NaOH solution (2

EXAMPLE 38

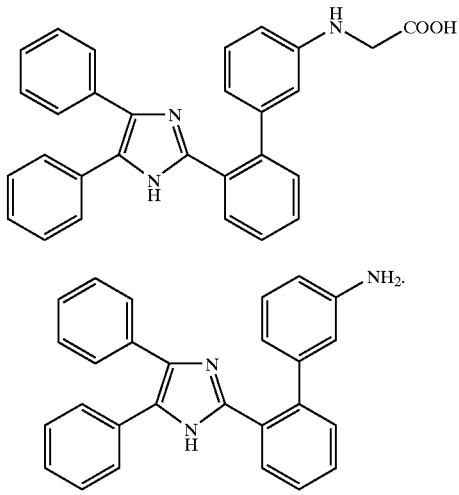

A

Followed the same experimental procedure as described in Example 37 Part B using Example 5 Part A compound and 3-amino phenyl boronic acid to give the title compound (yield 50%).

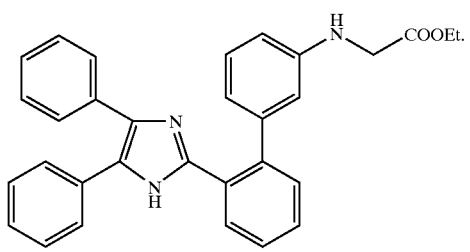

B

The experimental procedure as set out in Example 37 Part C employing the above Part B compound was followed to give the title compound (yield 55%).

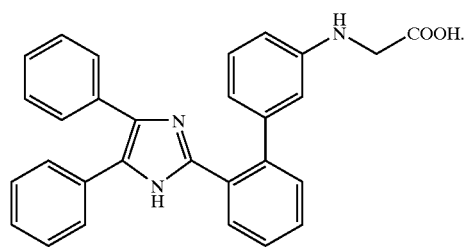

C

The experimental procedure as set out in Example 37 Part D employing the above Part B compound was followed to give the title compound (yield 75%).

EXAMPLE 39

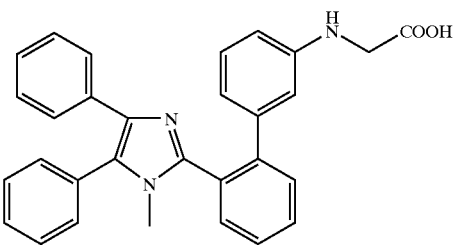

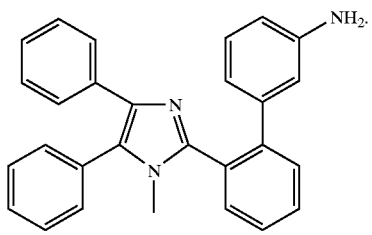

A

The experimental procedure as set out in Example 37 Part B was followed for Suzuki coupling between the Example 36 Part A compound and 3-amino phenyl boronic acid to give the title compound (yield 76%).

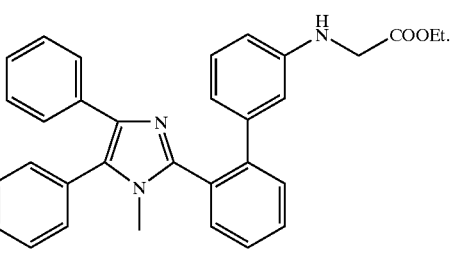

B

The experimental procedure as set out in Example 37 Part C employing the above Part B compound was followed to give the title compound (yield 75%).

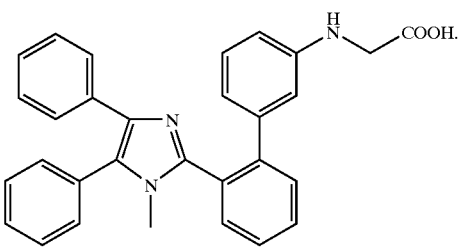

C

The experimental procedure as set out in Example 37 Part D employing the above Part B compound was followed to give the title compound (yield 60%).

EXAMPLE 40

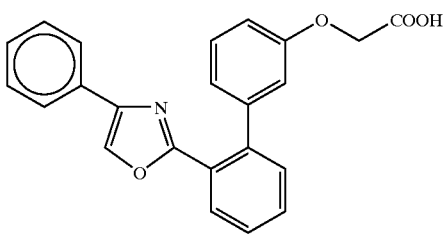

A

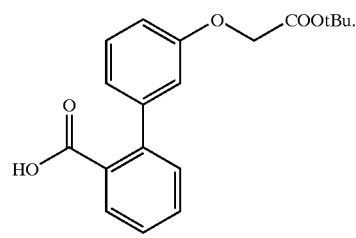

A mixture of Example 34 Part B compound (1.20 g, 3.84 mmol) in 10 mL of a 3:1 THF:water solution in ice bath was treated sequentially with sulfamic acid (1.31 g, 13.6 mmol) and sodium chlorite (1.22 g, 13.6 mmol). After 15 min the mixture was warmed to RT for 1 h and diluted with equal amounts of water and ether. The layers were equilibrated and the organic fraction washed with brine, dried (MgSO4) and concentrated to give the title compound (1.20 g, 95%).

B

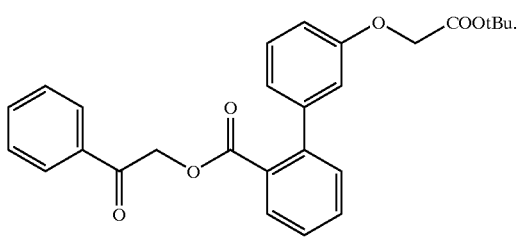

A mixture of Part A compound (0.53 g, 1.61 mmol), potassium carbonate (0.23 g, 1.70 mmol) and (a-bromo-acetophenone (0.29 g, 1.70 mmol) in 4 mL of DMF was stirred at RT overnight. The mixture was diluted with equal amounts of water and ether. The layers were equilibrated. The organic fraction was washed with water (2×20 mL), brine, dried over MgSO4 and concentrated under vacuum. The crude product was purified by flash chromatography on silica gel, eluting with 15:85 ethyl acetate/hexane to give title compound (590 mg, 82%).

C

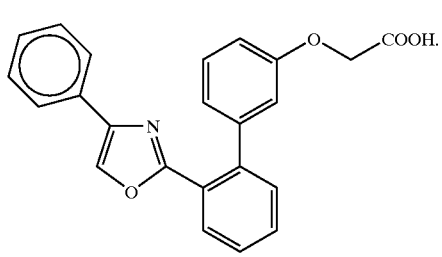

A mixture of Part B compound (0.59 g, 1.33 mmol) in 4 mL of acetic acid with ammonium chloride (0.60 g, 7.8 mmol) was heated to reflux for 48 h. The mixture was diluted with equal amounts of water and ethyl acetate. The organic fraction was washed with water, dried (MgSO4) and concentrated. The residue was purified by flash chromatography on silica gel eluting with 3:97:0.1 THF:dichloromethane:acetic acid to give title compound (70 mg, 14%).

EXAMPLE 41

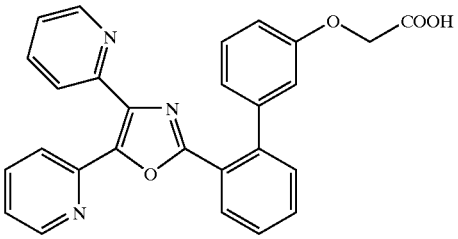

A

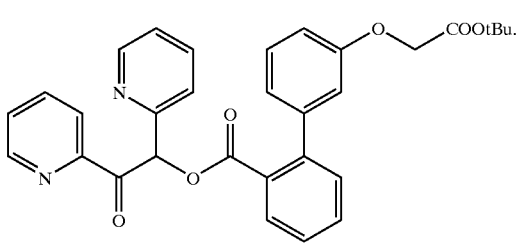

A solution of Example 40 Part A compound (0.32 g, 1 mmol), 4-dimethylamino pyridine (0.04 g, 0.3 mmol), 1-(3-dimethylaminopropyl)-3-ethylcarbodiimide hydrochloride (0.23 g, 1.20 mmol) and 2-pyridoin (0.21 g, 1.0 mmol) in dichloromethane (3 mL) was stirred at room temperature for 4 hr. The reaction mixture was washed with water, brine, dried over anhydrous MgSO$_4$ and concentrated. The crude product was purified by flash chromatography on silica gel, eluting with 3:7 ethyl acetate/hexane to give title compound (0.096 g, 20%).

B

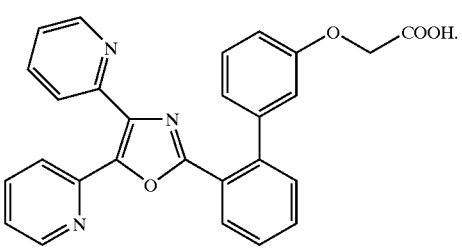

A mixture of Part A compound (0.096 g, 0.18 mmol) in 2 mL of acetic acid with ammonium chloride (0.096 g, 1.2 mmol) was heated to reflux for 4 h. The mixture was stripped under reduced pressure to an oil. The oil was purified on reverse phase column chromatography. The pure fractions were combined and concentrated to give the title compound (10 mg, 13%).

EXAMPLE 42

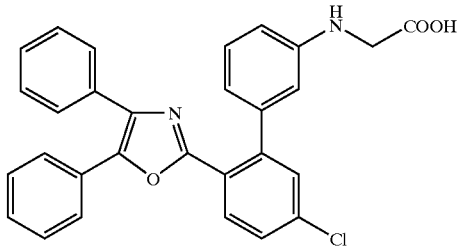

A

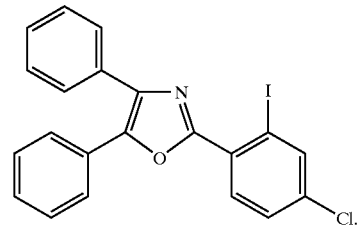

A solution of 2-iodo-4-chlorobenzoic acid (3.5 g, 12.4 mmol), 4-dimethylaminopyridine (1.65 g, 13.5 mmol), 1-(3-dimethylaminopropyl)-3-ethylcarbodiimide hydrochloride (2.6 g, 13.5 mmol) and benzoin (2.63 g, 12.4 mmol) in dichloromethane (20 mL) was stirred at room temperature for 4 h. The reaction mixture was washed with HCl (1N), NaOH (0.1 N), brine, dried over anhydrous MgSO$_4$ and concentrated to give the crude ketoester (5.9 gm, 99%).

A mixture of ketoester (5.9 g, 12 mmol) and ammonium chloride (5.50 g, 71 mmol) in glacial acetic acid (45 mL) was stirred at reflux for 4 hr. The reaction mixture was cooled and poured on ice. The tar-like solid was digested with hot ethanol (25 mL). The resulting beige solid was collected to give the title compound (4.5 g, 88%).

B

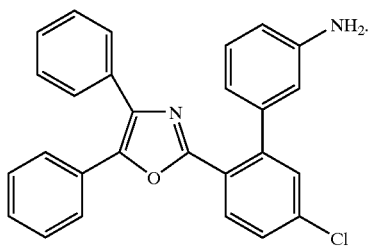

The experimental procedure as described in Example 37 Part B was followed employing the above Part A compound to give the title compound (yield 92%).

C

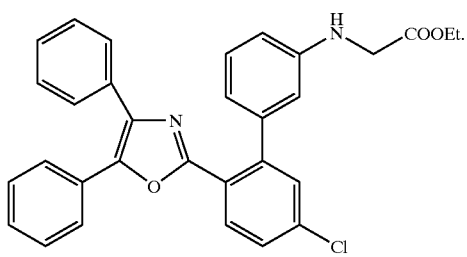

The experimental procedure as described in Example 37 Part C was followed, employing the above Part B compound, to give the title compound (yield 80%).

D

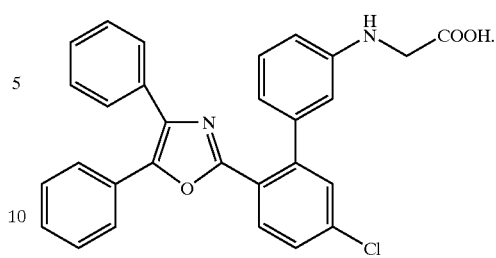

The Part C compound (0.48 g, 0.94 mmol) was diluted with ethanol (8 mL) and treated with NaOH (0.40 g; 10 mmol) and 3 mL of water. After 18 h at RT the mixture was acidified with citric acid to pH 3. The mixture was diluted with equal volumes of ethyl acetate and water. The layers were equilibrated and the organic fraction dried (Na2SO4) and concentrated. The residue was purified by preparative reverse phase column chromatography. The isolated material was further purified by flash column chromatography on silica gel with gradient elution from 4% ethanol in dichloromethane to 10% ethanol in dichloromethane with a trace of acetic acid to give the title compound (90 mg, 20%).

EXAMPLE 43

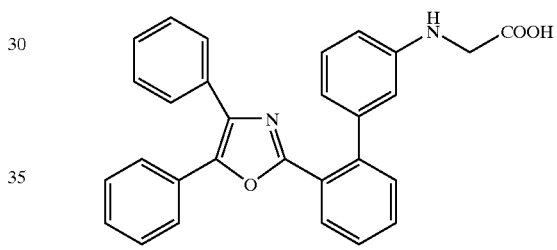

A

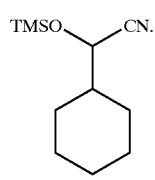

A mixture of cyclohexane carboxaldehyde (2.800 gm, 25 mmol) and trimethylsilyl cyanide (2.475 gm,25 mmol) was treated with zinc iodide (2 mg, 0.006 mmol). The mixture was stirred at RT for 3 h. The title compound was used without further purification, yield 100%.

B

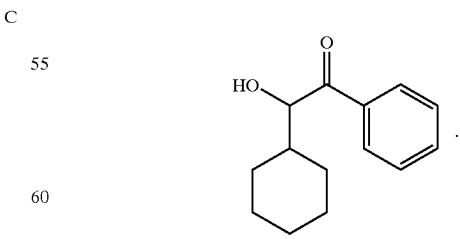

A mixture of Part A compound (2.00 g, 9.45 mmol) in THF (20 mL) at RT was treated with phenylmagnesiun chloride (3M in THF, 6.6 mL, 20 mmol). The mixture was stirred for 1 h at RT and then heated to reflux for 4 h. The reaction mixture was cooled and stirred with an excess of 1N HCl solution for 18 h. The mixture was partitioned between ether and water. The organics were dried over MgSO4, concentrated, and the residue purified by flash column chromatography on silica gel eluting with a step gradient of 1:9 to 3:7 ethyl acetate/hexane to give the title compound (750 mg, 34%).

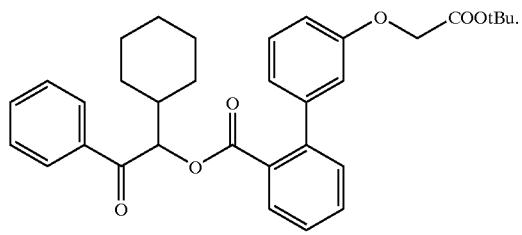

C

A solution of Example 40 Part A compound (330 mg, 1.0 mmol), 4-dimethylamino pyridine (40 mg, 0.3 mmol), 1-(3-dimethylaminopropyl)-3-ethylcarbodiimide hydrochloride (230 mg, 1.2 mmol) and Part B compound (220 mg, 1.0 mmol) in dichloromethane (2 mL) was stirred at room temperature for 4 h. The reaction mixture was washed with water (2×50 mL), brine (50 mL), dried over anhydrous MgSO$_4$ and concentrated. The residue was purified by flash column chromatography on silica gel eluting with a step gradient of 5:95 to 10:90 ethyl acetate/hexane to give title compound (400 mg, 75%).

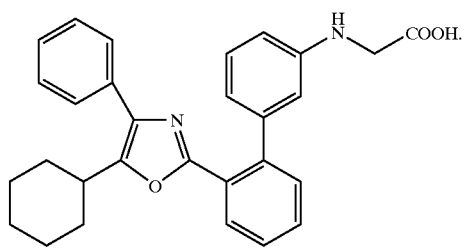

D

A mixture of Part C compound (400 mg, 0.75 mmol) and ammonium acetate (580 mg, 3.1 mmol) in glacial acetic acid (4 mL) was stirred at reflux for 18 h. The reaction mixture was cooled and concentrated. The crude oil was purified by flash column chromatography on silica gel eluting with 3:97:0.5 methanol/dichloromethane/acetic acid to the give the title compound (270 mg, 78%).

EXAMPLE 44

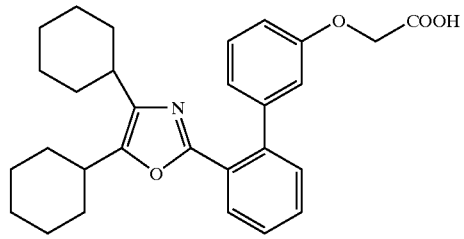

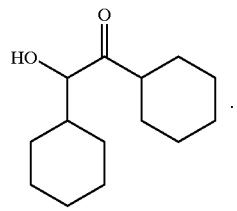

A

A mixture of Example 43 Part A compound (2.11 g, 10 mmol) in THF (10 mL) at RT was treated with cyclohexylmagnesiun chloride (2M in ether, 8 mL, 16 mmol). The mixture was stirred for 1 h at RT and then heated to reflux for 3 h. The reaction mixture was cooled and stirred with an excess of 1N HCl solution for 4 h. The mixture was partitioned between ether and water. The organics were dried over MgSO4, concentrated, and the residue purified by flash column chromatography on silica gel eluting with a step gradient of 1:9 to 4:6 ethyl acetate/hexane to give title compound as a foam (750 mg, 33%).

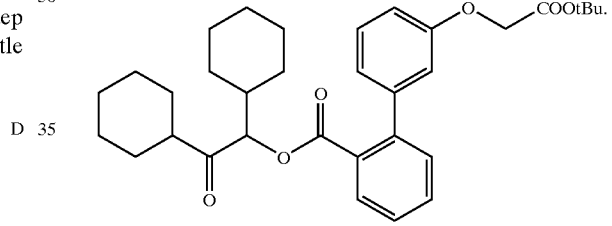

B

Part A compound was coupled with Example 40 Part A compound employing the procedure described in Example 43 Part C to obtain the title compound in 18% yeild.

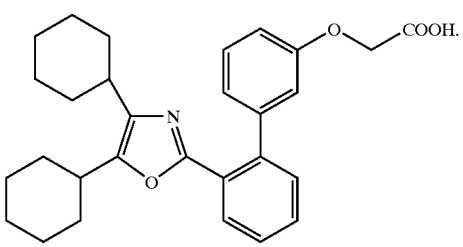

C

A mixture of Part B compound (240 mg, 0.45 mmol) and ammonium chloride (240 mg, 3.1 mmol) in glacial acetic acid (4 mL) was stirred at reflux for 24 h. The reaction mixture was cooled poured in water and filtered. The crude beige solid was triturated with water to get the title compound (180 mg, 87%).

EXAMPLE 45

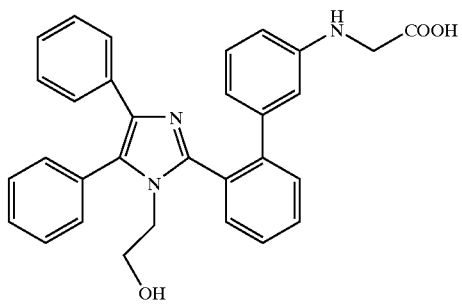

A

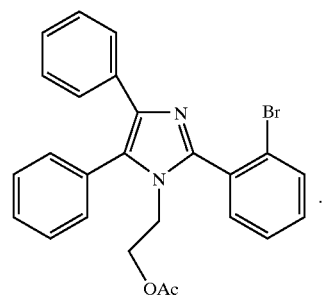

A mixture of Example 5 Part A compound (0.75 g, 2 mmol) in 5 mL of DMF at RT was treated with $K_2CO_3$ (0.28 g, 2 mmol) and bromoethyl acetate (1 mL, 6 mmol). The mixture was heated to 100° C. in a sealed tube stirred for 72 h. The mixture was cooled to RT and poured into water. The organics were extracted with ethyl acetate, dried over $Na_2SO_4$ and concentrated. The residue was purified on flash column chromatography with 15:85 ethyl acetate/hexane to give the title compound (0.40 g, 46%).

B

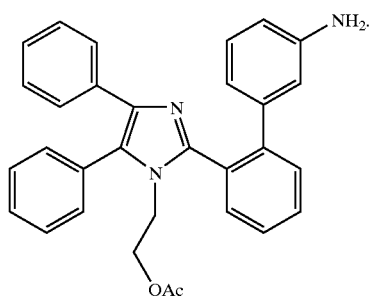

Nitrogen was bubbled through a solution of Part A compound (300 mg, 0.69 mmol), 3-aminophenyl boronic acid (158 mg, 1.00 mmol) and aqueous sodium carbonate (1 mL, 2M, 2 mmol) in toluene (2 mL) and ethanol (1 mL) at room temperature for 15 min. Tetrakis(triphenylphosphine)palladium(0) (550 mg, 0.04 mmol) was added and the mixture was stirred at 80° C. for 36 hr under argon. The reaction mixture was cooled to room temperature and extracted with ethyl acetate. The combined organic extracts were washed with brine, dried over anhydrous $MgSO_4$ and concentrated. The crude product was purified by flash chromatography on silica gel, eluting with 4:6 ethyl acetate/hexane to give title compound (150 mg, 46%).

C

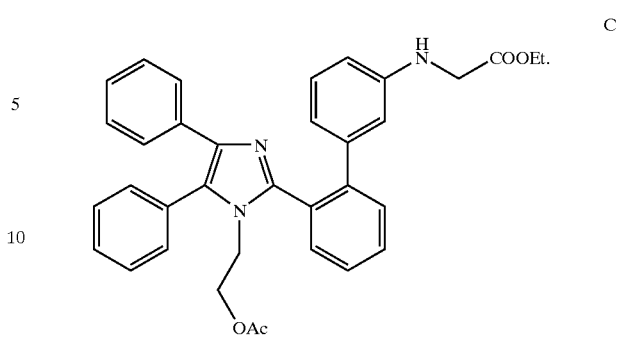

To a slurry of Part B compound (120 mg, 0.28 mmol) and potassium carbonate (40 mg, 0.28 mmol) in anhydrous dimethylformamide (3 mL) was added ethyl bromoacetate (50 mg, 0.28 mmol). The reaction mixture was stirred at room temperature for 18 h. The reaction was partitioned between diethyl ether and aqueous sodium bicarbonate solution. The organic layer was washed with water, and brine, then dried over anhydrous $MgSO_4$ and concentrated. The crude product was purified by flash chromatography eluting with 3:7 ethyl acetate/hexane to give title compound (95 mg, 60%).

D

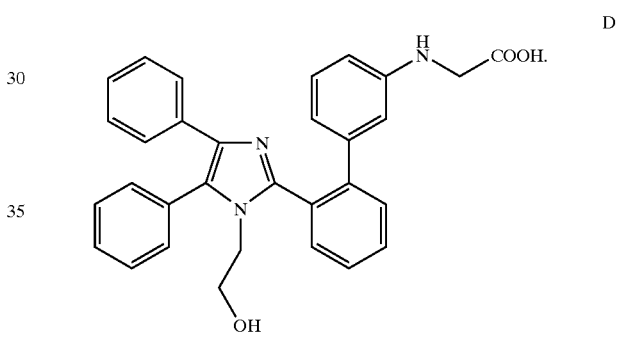

A mixture of Part C compound (90 mg, 0.16 mmol) in methanol (3 mL) was treated with 1M NaOH solution (1 mL, 1 mmol). After stirring for 3 h at reflux the mixture was cooled and diluted with ether. Citric acid was added until the aqueous fraction maintained a pH of 3. The layers were equilibrated and separated. The organic fraction was dried over $MgSO_4$, and concentrated to give the title compound (80 mg, 100%).

EXAMPLE 46

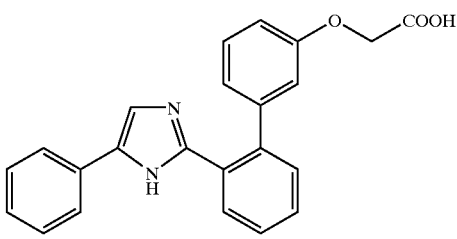

A mixture of Example 40 Part B compound (0.59 g, 1.33 mmol) in 4 mL of acetic acid with ammonium chloride (0.60 g, 7.8 mmol) was heated to reflux for 48 h. The mixture was diluted with equal amounts of water and ethyl acetate. The organic fraction was washed with water, dried ($MgSO_4$) and concetrated. The remainder was purified on silica by flash column chromatography with 3:97:0.1 THF:dichloromethane:acetic acid to give 15 mg (3%) title compound.

EXAMPLE 47

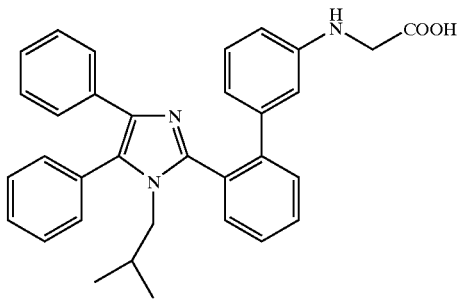

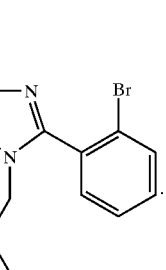

A

A mixture of Example 5 Part A compound (0.75 g, 2 mmol) in DMF (5 mL) was treated with K2CO3 (420 mg, 4 mmol) and isobutyl iodide (740 mg, 4 mmol). The mixture was heated in a sealed tube at 60° C. for 18 h. The tube was cooled, and the contents diluted with equal amounts of water and ether. The organic fraction was dried over anhydrous MgSO$_4$ and concentrated to a thick oil. The crude product was purified by flash chromatography on silica gel, eluting with a step gradient of 2:98 to 7:93 ethyl acetate/hexane to give title compound (250 mg, 30%).

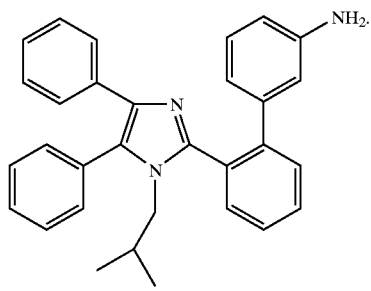

B

The experimental procedure as set out in Example 37 Part B employing the above Part A compound was followed to give the title compound (yield 62%).

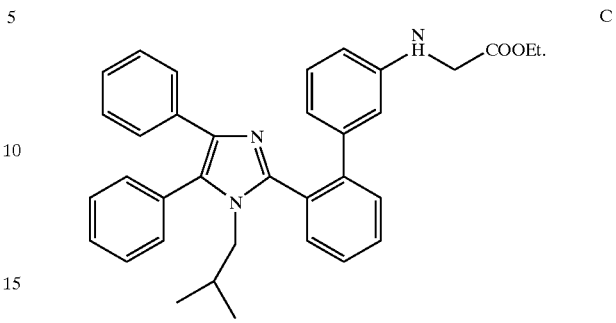

C

The experimental procedure as set out in Example 37 Part C employing the above Part B compound was followed to give the title compound (yield 72%).

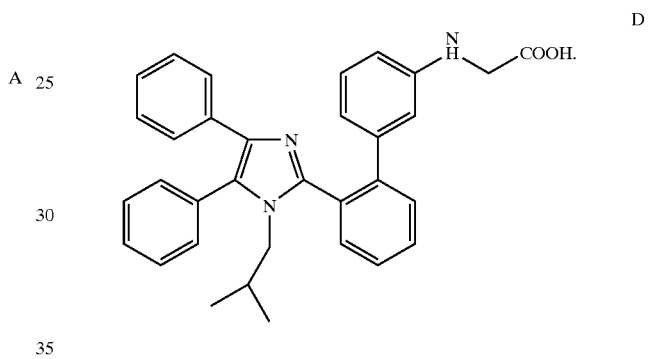

D

The experimental procedure as set out in Example 37 Part D employing the above Part C compound was followed to give the title compound (yield 61%).

EXAMPLE 48

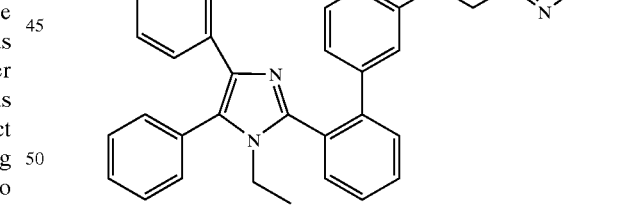

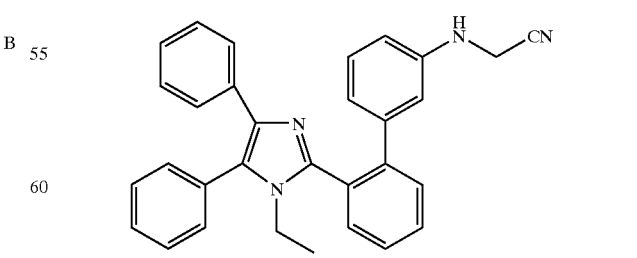

A.

A solution of Example 6 Part A compound (0.49 g, 1.18 mmol) in DMF (2 mL) at RT was treated with K$_2$Co$_3$ (0.28 g, 2 mmol) and bromoacetonitirile (0.14 g; 1.20 mmol). The mixture was stirred overnight at RT and then heated to 60° C. for 4 h. The reaction mixture was cooled to RT and poured into water. The solid was collected and dried overnight to give the title compound (0.45 g, 85%).

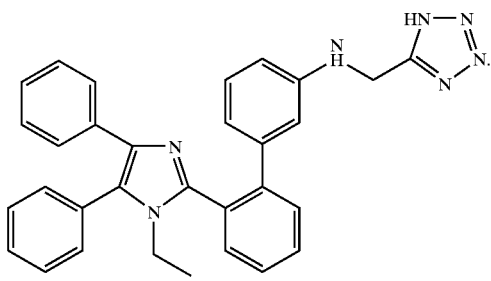

B

A solution of Part A compound (0.40 g, 0.88 mmol) in xylene (2 mL) was treated with azidotrimethyltin (0.23 g, 1.14 mmol) and the mixture was heated under N2 for 18 h at 135° C. The reaction was quenched with methanol and the mixture concentrated to an oil. The oil was purified by flash column chromatography on silica with a step wise gradient using 15/85 ethyl acetate/hexane then 5/95 methanol/dichloromethane to give 0.30 g of the title compound as a white foam (68%).

EXAMPLE 49

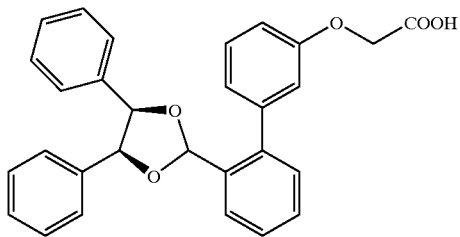

A mixture of Example 34 Part B compound (0.20 g, 0.64 mmol), pyridinium p-toluenesulfonate (40 mg), and meso-1,2-dihydroxy-1,2-diphenylethane (0.14 g, 0.64 mmol) in toluene (5 mL) was heated to 80° C. for 36 h and then brought to reflux for 3 h. The mixture was cooled to RT and diluted with water and ethyl acetate. The organics were dried (MgSO4) and carried on to the next step without further characterization.

The crude ester (~0.64 mmol) in methanol (4 mL) was treated with 1M NaOH (1 mL, 1 mmol) and stirred overnight. The mixture was concentrated and the residue purified by chromatograpy on SP207 gel with a stepwise gradient from water to 80% methanol/water in 20% increments (70 mL portions). The pure fractions were combined and freeze dried to give the title compound as a white lyophilate (130 mg, 45%).

EXAMPLE 50

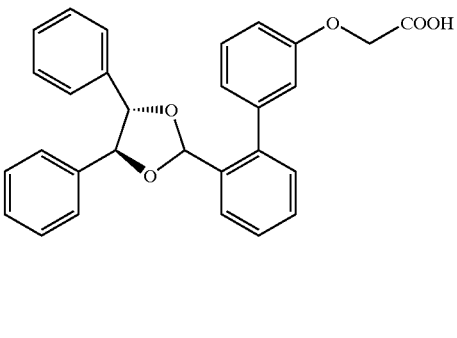

A mixture of Example 34 Part B compound (0.20 g, 0.64 mmol), pyridinium p-toluenesulfonate (40 mg), and (R,R)-1,2-dihydroxy-1,2-diphenylethane (0.14 g, 0.64 mmol) in toluene (5 mL) was heated to 80° C. for 36 h and then brought to reflux for 3 h. The mixture was cooled to RT and diluted with water and ethyl acetate. The organics were dried (MgSO4) and carried on to the next step without further characterization.

The crude ester (~0.64 mmol) in methanol (4 mL) was treated with 1M NaOH (1 mL, 1 mmol) and stirred overnight. The mixture was concentrated and the residue purified by chromatograpy on SP207 gel with a stepwise gradient from water to 80% methanol/water in 20% increments (70 mL portions). The pure fractions were combined and freeze dried to give the title compound as a white lyophilate (200 mg, 65%).

EXAMPLE 51

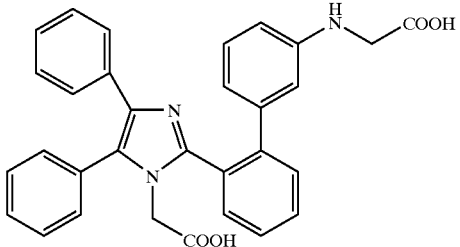

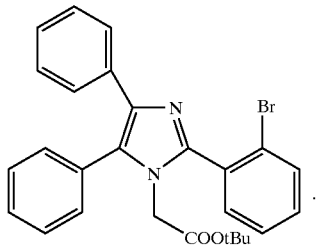

A

The experimental procedure as set out in Example 37 Part A using tert-butyl bromoacetate as the alkylating agent was followed to give the title compound (yield 92%).

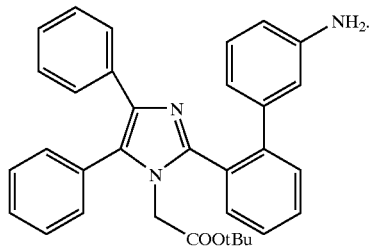

The experimental procedure as set out in Example 37 Part B employing the above Part A compound was followed to give the title compound (yield 76%).

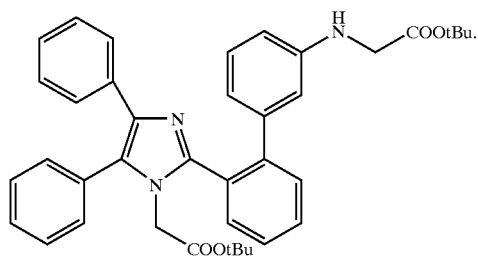

The experimental procedure as set out in Example 37 Part C employing the above Part B compound was followed using tert-butyl bromoacetate to give the title compound (yield 75%).

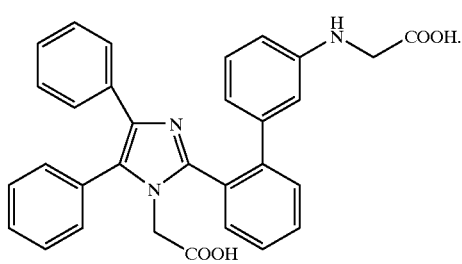

Part C compound (0.16 g, 0.26 mmol) in a 1:1 mixture of trifluoroacetic acid/dichloromethane (4 mL) was stirred at room temperature overnight. The mixture was concentrated and the residue adjusted to pH 13 with 1N NaOH solution. The solution was purified by chromatograpy on SP207 gel with a stepwise gradient from water to 60% methanol/water in 20% increments (80 mL portions). The pure fractions were combined, the pH of the combined fractions were adjusted to pH 6.5 with 0.1 N NaOH and freeze dried to give 83 mg (62%) of title compound as a white lyophilate.

EXAMPLE 52

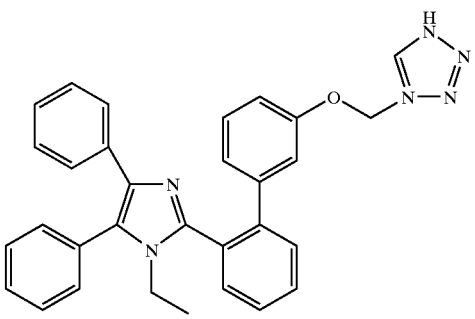

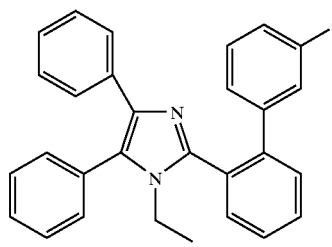

A mixture of Example 8 Part B compound (0.25 g, 0.6 mmol), K2CO3 (0.12 g, 0.9 mmol) and DMF (3 mL) was treated with bromoacetonitrile (0.11 g; 0.9 mmol) and the mixture stirred for 72 h. TLC indicated that the reaction was not complete and additional bromoacetonitrile (0.11 g, 0.9 mmol) and K2CO3 (0.12 g, 0.9 mmol) were added. The mixture was stirred for 18 h. The mixture was diluted with equal amounts of ethyl acetate and water. The organic fraction was washed with water, dried (MgSO4) and concentrated. The remainder was purified by flash column chromatography with 20% ethyl acetate in hexane to give 0.22 g (80%) of the title compound.

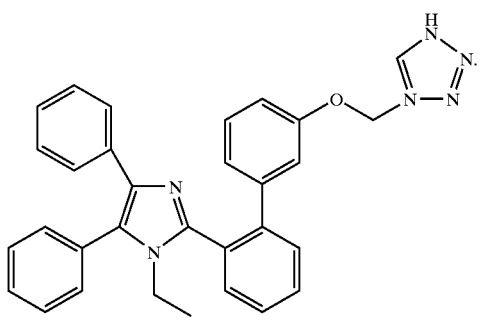

A mixture of Part A compound (0.20 g, 0.44 mmol) in xylenes (2 mL) was treated with azidotrimethyltin (0.11 g, 0.53 mmol) and warmed to 135° C. (bath temp) for 18 h. The mixture was concentrated and stirred with methanol for 45 min. The methanol solution was concentrated and the residue purified by flash column chromatography with a step gradient elution using dichloromethane (80 mL), 1% methanol/dichloromethane (200 mL) and 2% methanol/dichloromethane (200 mL) to give 36 mg (16%) of the title compound.

EXAMPLE 53

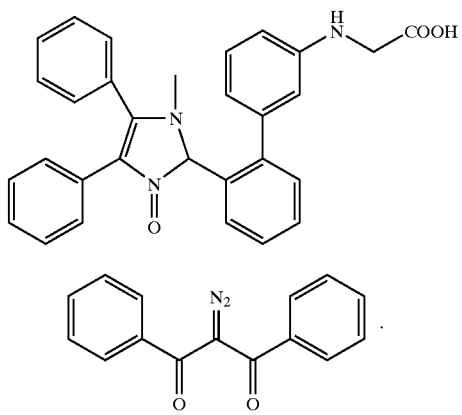

A

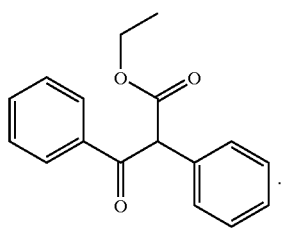

A solution of 1,3-diphenyl-1,3-propanedione (4.50 g, 20 mmol) in 150 mL of dichloromethane was mixed with triethylamine (2.07 g, 20 mmol) and cooled to −5° C. (internal temperature). The mixture was then treated with 4-aetamidobenzenesulfonyl azide (4.80 g, 21 mmol). The reaction was maintained at −4° C. for 4 h and then warmed to RT overnight. The mixture was diluted with water and the organic fraction was washed with 1 N NaOH solution (4×125 mL), water (2×50 mL), dried (Na2SO4) and concentrated to an oil. The oil was diluted with a small volume (15 mL) of methanol and 3 drops of water. The resulting solid was collected and dried to give 1.50 g (30%) of the title compound.

(Reference Meier, H. Chem Ber. 119, 3382–3393, 1986.)

B

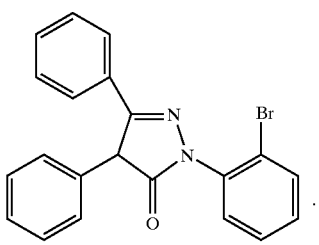

A mixture of the Part A compound (1.5 g; 6 mmol) in 50 mL of ethanol was refluxed for 18 h. The ethanol was stripped off under reduced pressure to leave a thick oil. The oil was solidified by mixing with hexane (10 mL) and concentrating under reduced pressure. After drying 1.6 g (100%) of the title compound was obtained as a beige solid.

C

A mixture of Part B compound (0.1 g, 0.37 mmol) in 3 mL of ethanol was treated with 2-bromophenylhydrazine hydrochloride (84 mg, 0.37 mmol) and heated to reflux overnight. The ethanol was removed and the remainder was purified on silica gel by flash column chromatography with 65:35 ethyl acetate:hexane to give 90 mg (62%) of the title compound.

D

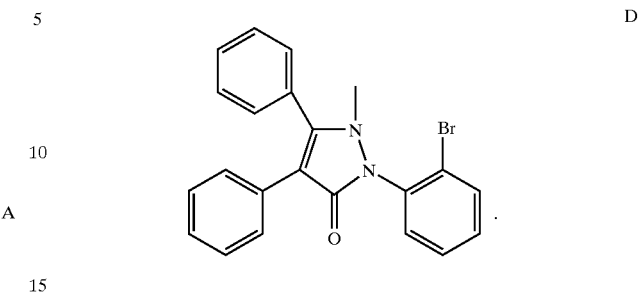

A mixture of Part C compound (0.13 g, 0.33 mmol), K$_2$CO$_3$ (0.10 g, 0.73 mmol) and DMF (3 mL) was treated with methyl iodide (0.10 g, 0.70 mmol) and the mixture stirred for 18 h. The mixture was diluted with equal amounts of ethyl acetate and water. The organic fraction was washed with water, dried (MgSO$_4$) and concentrated. The remainder was purified by flash column chromatography with 10% ethyl acetate in hexane to give 80 mg (60%) of the title compound.

E

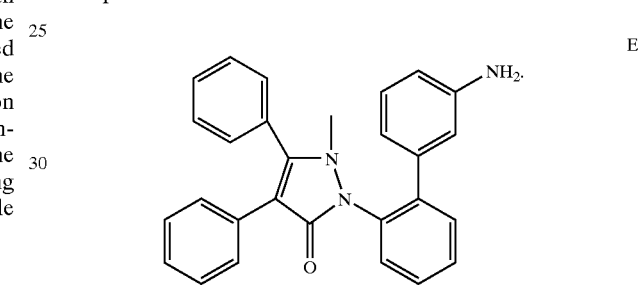

A mixture of Part D compound (80 mg, 0.19 mmol), toluene (1 mL), ethanol (0.5 mL), 3-aminophenyl boronic acid (35 mg, 0.25 mmol), and 2 N Na2CO3 solution (0.125 µL, 0.25 mmol) was degassed with a gentle N2 flow for 10 min. The mixture was treated with terakis (triphenylphosphine)-palladium (0) (10 mg) and the mixture heated to 80° C. for 18 h. The mixture was cooled to RT and diluted with equal portions of water and ethyl acetate. The organic fraction was dried over MgSO$_4$ and concentrated. The remainder was purified on silica gel by flash column chromatography with 65:35 ethyl acetate:hexane as a mobile phase to give 66 mg (80%) of the title compound.

F

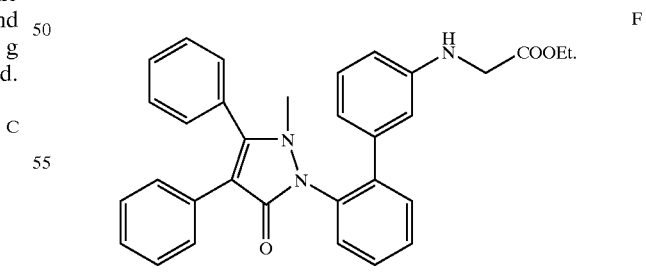

A mixture of DMF (0.5 mL), potassium carbonate (30 mg, 0.21 mmol) and Part E compound (60 mg, 0.15 mmol) was treated with ethyl bromoacetate (17 µL, 0.15 mmol). The mixture was stirred overnight and diluted with equal potions of ethyl acetate and water. The layers were equilibrated, the organic fraction dried (MgSO$_4$) and concentrated. The residue was purified on silica gel by flash column chromatography with 20:80 ethyl acetate:hexane as a mobile phase to give 60 mg (80%) of the title compound.

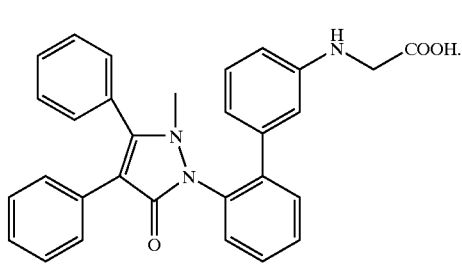

A solution of Part F compound (60 mg, 0.12 mmol) and methanol (3 mL) was treated with 1 N NaOH solution (1 mL, 1 mmol) and stirred overnight. The mixture was acidified with citric acid until a pH of 3 was maintained. The resulting slurry was diluted with equal portions of ethyl acetate and water and the layers equilibrated. The orgainc fraction was dried over $Na_2SO_4$ and concentrated. Pumping overnight gave 50 mg (88%) of the title compound.

EXAMPLE 54

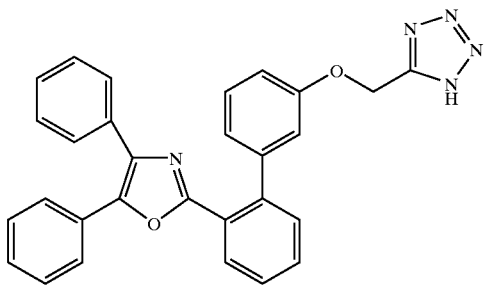

The title compound was generated by the procedure described in Example 19 starting/with Compound A Example 13.

EXAMPLE 55

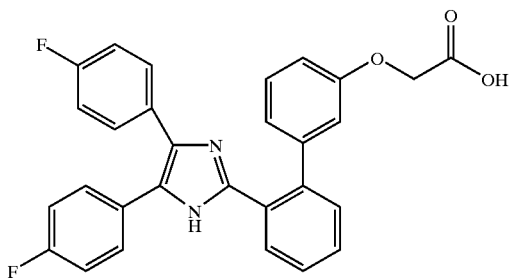

The title compound was generated following the procedure described in Example 34 utilizing 4,4'-difluorobenzil.

EXAMPLE 56

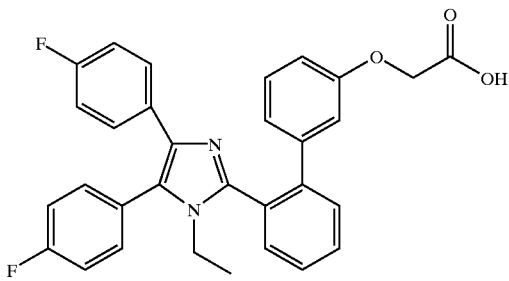

The title compound was generated from Example following the procedure described in Example 35.

EXAMPLE 57

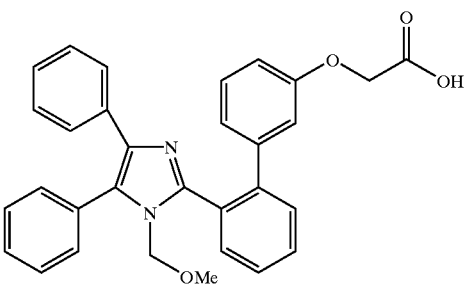

Following the procedure described in Example 35, Compound A Example 35 was alkylated with chloromethyl methyl ether and hydrolyzed to give the title compound.

EXAMPLE 58

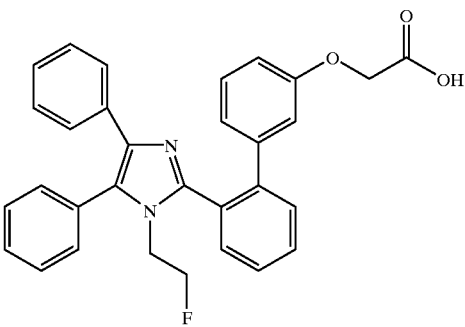

Following the procedure described in Example 35, Compound A Example 35 was alkylated with 1-bromo-2-fluoroethane and hydrolyzed to give the title compound.

EXAMPLE 59

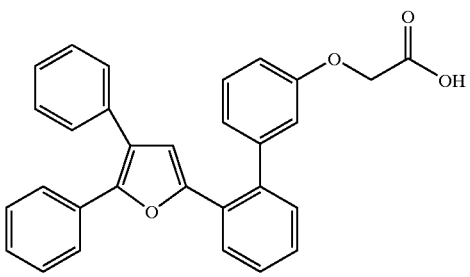

The title compound was generated by the procedure described in Example 8 starting with Example 19 Part E compound.

EXAMPLE 60

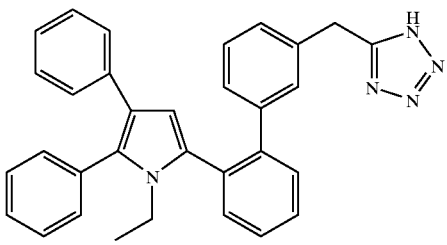

The title compound was generated following the procedure described in Example 23, starting with Example 21 Part A compound.

EXAMPLE 61

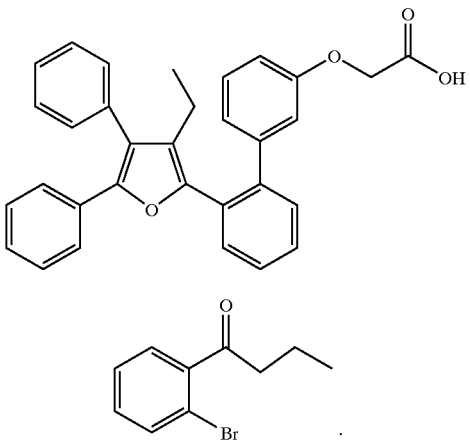

A

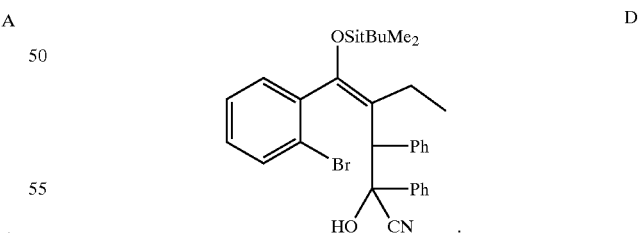

To a stirred solution of 2-bromobenzoyl chloride (1.31 mL, 10.0 mmol) in THF (10 mL) under argon at −22° C. was added tributylphosphine (2.74 mL, 11.0 mmol) over 10 min. The temperature was not allowed to rise above −15° C. After 20 min, a solution of n-propylmagnesium chloride (5.0 mL, 10.0 mmol, 2 M in ether) was added in one portion. The reaction temperature rose almost at once to 34° C. and subsided to −20° C. over 10 min. After an additional 10 min, 1 M aqueous HCl (18 mL) was added and the mixture was extracted with ether (100 mL). The ether extract was washed once with brine, once with saturated sodium bicarbonate solution, dried (MgSO$_4$) and evaporated. Purification by flash chromatography on silica gel (5×25 cm column, 38:62 CH$_2$Cl$_2$/hexanes) gave the title compound as a yellow oil, 2.28 g, 100% yield.

B

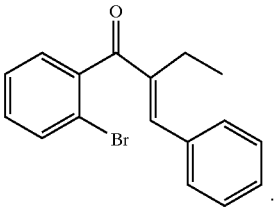

To a stirred solution of potassium hydroxide (1.23 g, 22 mmol) in methanol (10 mL) at room temperature under argon was added Part A compound (1.00 g, 4.40 mmol). After five min, benzaldehyde (1.34 mL, 13.2 mmol) was added in one portion. After 4 h, the reaction mixture was cooled to 0° C., treated with 1 M aqueous HCl to bring the solution to pH 7.5 and then evaporated at <30° C. The residue was partitioned between CH$_2$Cl$_2$ and brine. The aqueous phase was extracted twice with CH$_2$Cl$_2$, and the extracts were combined, dried (MgSO$_4$) and evaporated. Purification by flash chromatography on silica gel (5×15 cm column, 2:3 CH$_2$Cl$_2$/hexanes) gave the title compound as a light yellow oil, 1.29 g, 95% yield.

C

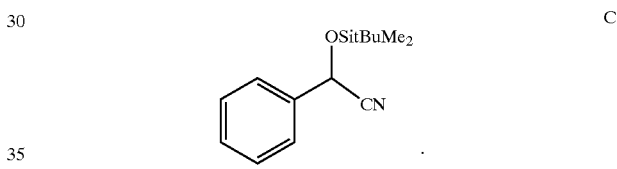

To a stirred slurry of benzaldehyde (5.1 mL, 50.0 mmol), potassium cyanide (13 g, 200 mmol), and t-butyldimethylsilyl chloride (9.0 g, 60 mmol) in acetonitrile (100 mL) at room temperature under argon was added zinc iodide (250 mg, 0.8 mmol). After 14 h, the reaction mixture was filtered and the filtrate evaporated. The evaporate was slurried in hexanes for 1 h under nitrogen, refiltered and evaporated. The oily residue was distilled (80–83° C., 0.8 torr) to give the title compound as a colorless oil, 7.68 g, 62% yield.

D

A solution of lithium diisopropylamide was prepared at 0° C. under argon from diisopropylamine (1.2 mL, 8.1 mmol) and n-butyllithium (3.2 mL, 8.0 mmol, 2.5 M in hexanes) in ether (20 mL). To this solution at −72° C. was added a solution of Part C compound (1.80 g, 7.30 mmol) in ether (5 mL). The temperature was not allowed to rise above −67° C. After 1 h, a solution of Part B compound (2.30 g, 7.30 mmol) was added over the course of 10 min. The reaction was stirred at −78° C. for 2 h and then stored at −40° C. for 14 h. The reaction was then warmed to 0° C. for 30 min and then quenched with saturated ammonium chloride solution. The reaction mixture was extracted with ether (100 mL). The extract was dried (MgSO$_4$) and evaporated. Purification by flash chromatography on silica gel (5×25 cm column, 1:1 CH$_2$Cl$_2$/hexanes) gave the title compound as a white amorphous solid, 1.88 g, 46% yield.

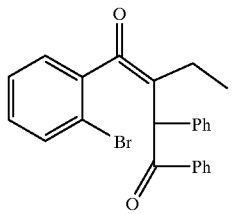

E

To a solution of Part D compound (1.65 g, 2.93 mmol) in THF (5 mL) at room temperature under argon was added tetrabutylammonium fluoride solution (3.6 mL, 3.6 mmol, 1 M in THF). After 1 h, the reaction was quenched with saturated sodium bicarbonate solution and extracted twice with CH$_2$Cl$_2$ (50 mL). The extracts were combined, dried (MgSO$_4$) and evaporated. Purification by flash chromatography on silica gel (5×25 cm column, 1:1 CH$_2$Cl$_2$/hexanes) gave the title compound (as a mixture of diastereomers) as a colorless oil, 1.05 g, 85% yield.

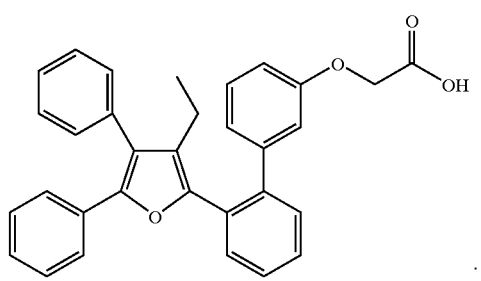

F

Analogous to the procedure described in Example 19 Part C, Compound E (600 mg, 1.42 mmol) gave the title compound as a colorless oil, 557 mg, 97% yield.

G

Analogous to the procedures described in Example 8, Part F compound gave the title compound.

EXAMPLE 62

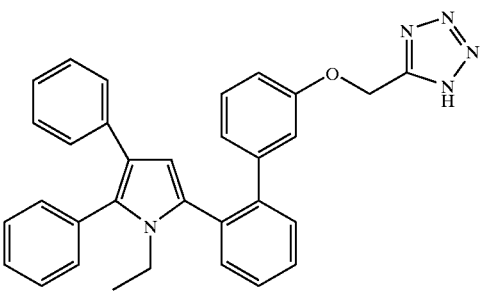

Analogous to the procedure described in Example 19, Example 21 Part A compound gave the title compound.

EXAMPLE 63

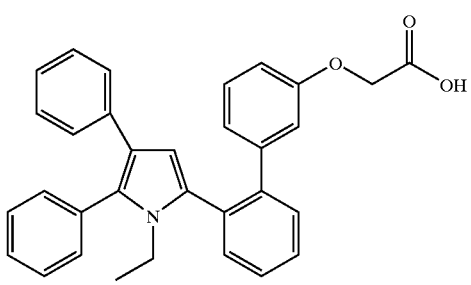

Analogous to the procedure described in Example 8, Example 21 Part A compound gave the title compound

EXAMPLE 64

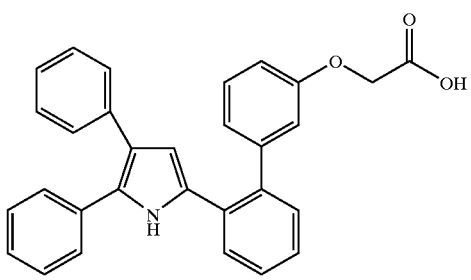

Analogous to the procedure described in Example 8, Example 20 Part A compound gave the title compound

EXAMPLE 65

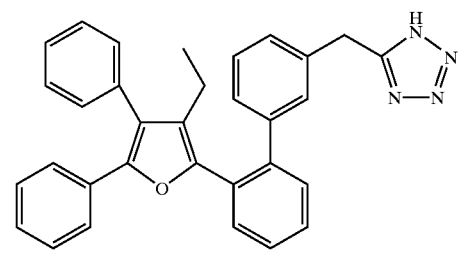

Analogous to the procedure described in Example 23, Example 61 Part F compound gave the title compound.

EXAMPLE 66

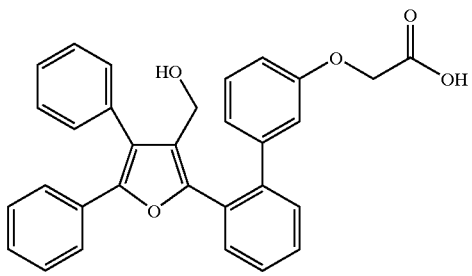

A.

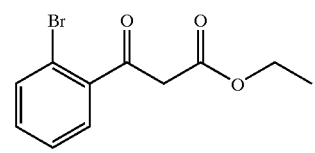

To a stirred slurry of NaH (60% oil dispersion, 10.0 g, 250 mmol) in diethyl carbonate (40 mL) and toluene (15 mL) at room temperature under argon, was added absolute ethanol (150 µL) and then a solution of 2-bromoacetophenone (24.88 g, 125 mmol) in toluene (20 mL) over 20 min. The reaction temperature rose autogenously to 80° C. and then was maintained at that temperature for 2 h. The mixture was cooled to room temperature and acetic acid (15 mL) was added. The resulting bulky solid was treated with ice-cold water (100 mL) and then extraced twice with ether (250 mL). The extracts were combined, dried (MgSO$_4$) and evaporated to give the crude ketoester as a yellow oil, 29.75 g. Purification of a portion of the crude product (log) by flash chromatography on silica gel (5×25 cm column, 9:1 CH$_2$Cl$_2$/hexanes) gave the title compound as a light yellow oil, 7.83 g, 70% calculated yield.

B

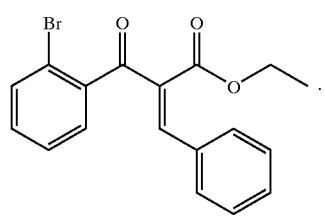

A solution of Part A compound (5.42 g, 20.0 mmol), benzaldehyde (2.24 mL, 22 mmol), 6-aminocaproic acid (100 mg, 0.76 mmol) and acetic acid (3 mL) in benzene (10 mL) was heated to reflux for 1 h using a Dean-Stark trap. The reaction mixture was cooled to room temperature, diluted with ethyl acetate and washed four times with saturated sodium bicarbonate solution until the washings were pH 8. The organic phase was dried (MgSO$_4$) and evaporated. Purification of the crude product by flash chromatography on silica gel (5×25 cm column, 7:3 CH$_2$Cl$_2$/hexanes) gave the title compound (55:45 mixture of geometric isomers) as a white amorphous solid, 4.38 g, 61% yield.

C

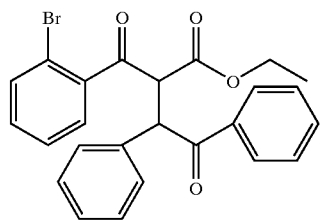

Analogous to the procedure described in Example 19 Part B, Part B compound was used to prepare the title compound.

D

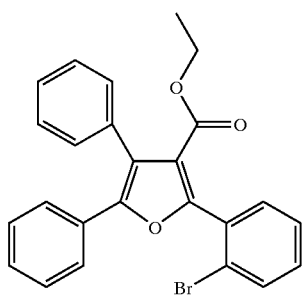

Analogous to the procedure described in Example 19 Part C, Part C compound was used to prepare the title compound.

E

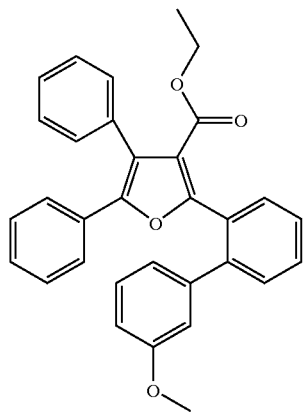

Analogous to the procedure described in Example 8 Part A, Part D compound was used to prepare the title compound.

F

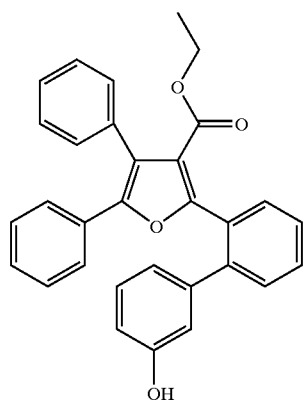

Analogous to the procedure described in Example 8 Part B, Part E compound was used to prepare the title compound.

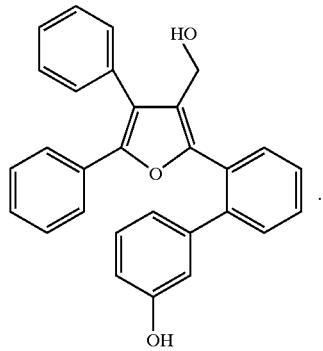

G

To a stirred solution of Example 66 Part F compound (497 mg, 1.08 mmol) in THF (2 mL) at room temperature under argon was added a solution of lithium aluminum hydride (1.5 mL, 1.5 mmol, 1 M in THF) over 30 sec. The resulting light yellow solution was stirred for 15 min, whereupon a gelatinous mixture formed. This was quenched cautiously with 5% potassium hydrogen sulfate solution and extracted three times with ethyl acetate (20 mL). The organic extracts were combined, dried (MgSO$_4$) and evaporated to give a light pink solid, 440 mg, 97% yield.

H

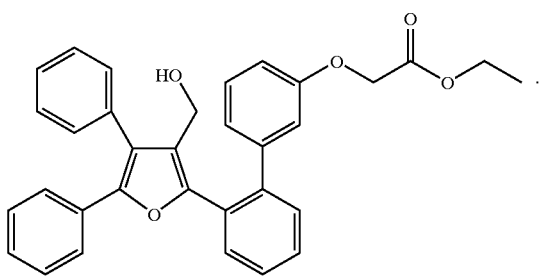

Analogous to the procedure described in Example 8 Part C, Part G compound was used to prepare the title compound.

I

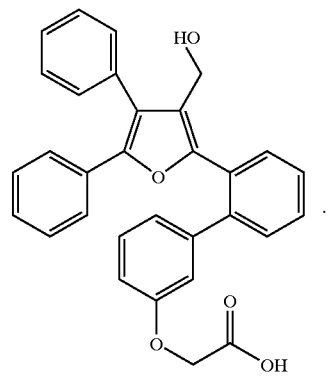

By the procedure described in Example 8 Part D, Part H compound was used to prepare the title compound.

EXAMPLE 67

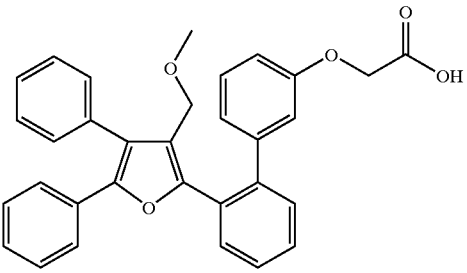

A

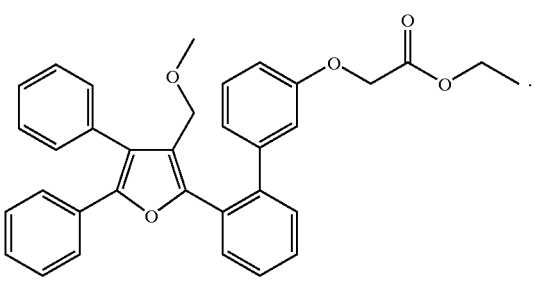

To a stirred solution of Example 66 Part H compound (112 mg, 0.222 mmol) in methanol (5 mL) was added concentrated sulfuric acid (2 drops). The mixture was heated in a sealed tube at 100° C. for 9 h. The reaction mixture was cooled to room temperature, treated with saturated sodium bicarbonate solution and evaporated to dryness. The residue was dissolved in CH$_2$Cl$_2$, dried (MgSO$_4$) and evaporated to give the title. compound as a colorless oil, 98 mg, 88% yield.

B

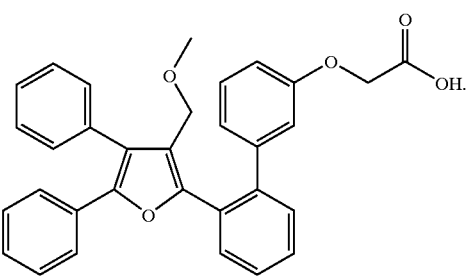

Analogous to the procedure described in Example 8 Part D, Part A compound was used to prepare the title compound.

EXAMPLE 68

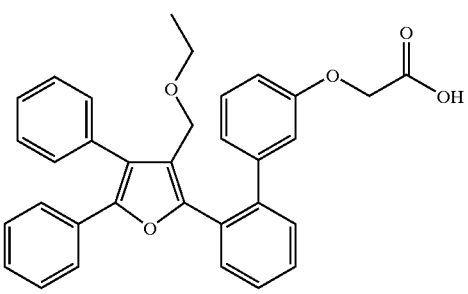

By the procedure described in Example 67, Example 66 Part H compound was used to prepare the title compound, substituting ethanol for methanol in the procedure.

EXAMPLE 69

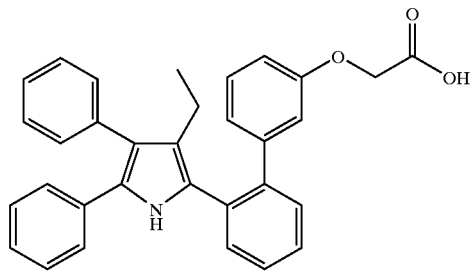

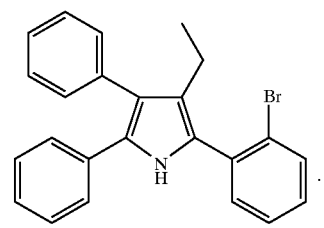

Analogous to the procedure described in Example 20, Example 61 Part E compound was used to prepare the title compound.

B

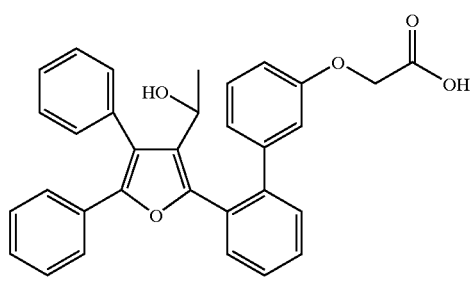

Analogous to the procedure described in Example 8, Example 69 Part A compound was used to prepare the title compound.

EXAMPLE 70

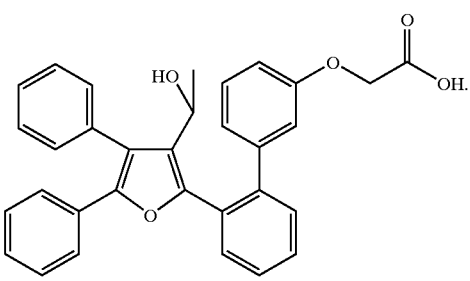

A.

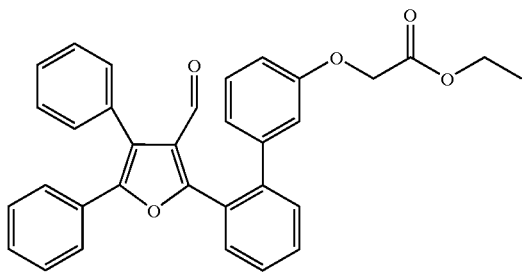

A steady stream of dried air was bubbled into a stirred slurry consisting of Example 66 Part H compound (504 mg, 1.0 mmol), powdered 4 A molecular sieves (200 mg) and tetrapropylammonium perruthenate (30 mg, 0.085 mmol) in toluene (3.5 mL) as the reaction was heated to 65° C. After 1 h, the reaction was cooled to room temperature, diluted with $CH_2Cl_2$ and filtered through silica gel (~20 g). Evaporation gave the title compound as a colorless oil, 490 mg, 97%).

B

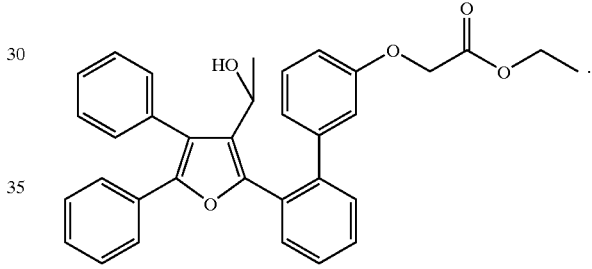

To a solution of Part A compound (125 mg, 0.25 mmol) in $CH_2Cl_2$ at room temperature under argon, was added a solution of trimethylaluminum (0.25 mmol, 0.5 mmol, 2 M in $CH_2Cl_2$), dropwise over 5 min. After 1 h, the reaction was quenched cautiously with 10% citric acid solution and extracted once with $CH_2Cl_2$. The organic phase was dried ($MgSO_4$) and evaporated. Purification of the crude product by flash chromatography on silica gel (2.5×15 cm column, 3:97 ether/$CH_2Cl_2$) gave the title compound as a colorless oil, 124 mg, 96% yield.

C

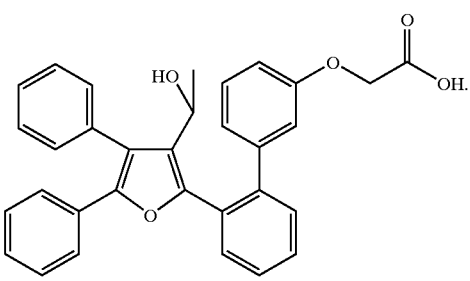

Analogous to the procedure described in Example 8 Part D, Part B compound was hydrolyzed to prepare the title compound.

EXAMPLE 71

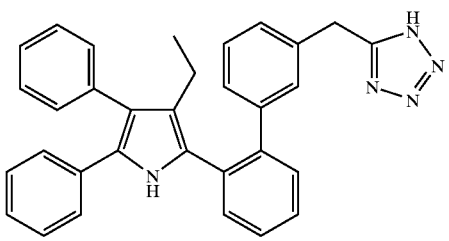

Analogous to the procedure described in Example 23, Example 69 Part A compound was used to prepare the title compound.

EXAMPLE 72

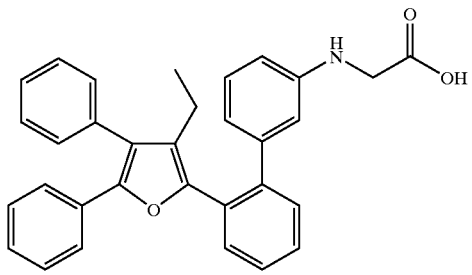

Analogous to the procedure described in Example 3, Example 61 Part F compound was used to prepare the title compound.

EXAMPLE 73

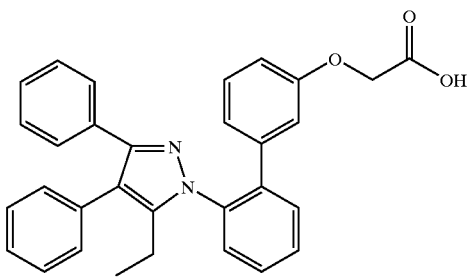

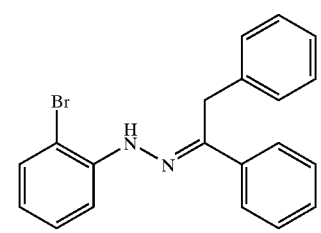

A

To a stirred slurry of 2-bromophenylhydrazine hydrochloride (31.02 g, 0.139 mol) at room temperature under nitrogen in 95% ethanol (500 mL) was added sodium acetate trihydrate (18.87 g, 0.139 mol) and deoxybenzoin (30.96 g, 0.139 mol). The mixture was heated to reflux for 2 h and then partially cooled and evaporated. The residue was slurried in saturated sodium bicarbonate solution (300 mL), filtered, washed with water and dried in vacuo at 60° C. for 16 h. The resulting solids were triturated in hot methanol (200 mL), filtered and dried to provide the title compound (96:4 mixture of Z/E isomers) as a white solid, mp 126–128° C., 36.84 g, 76% yield.

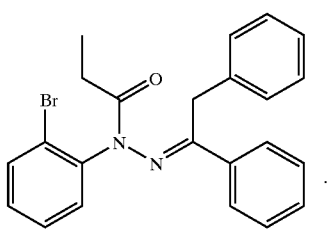

B

To a stirred slurry of sodium hydride (60% dispersion, 1.43 g, 35.8 mmol) in N-methylpyrrolidone (NMP, 25 mL) at room temperature under nitrogen, was added a solution of Part A compound (10.0 g, 27.4 mmol) in NMP (15 mL) over 5 min. The temperature autogenously rose to 54° C. as gas was evolved and a deep red solution formed. The reaction mixture was heated to 60° C. for 3 h and then cooled to room temperature. To this solution was added freshly distilled propionic anhydride (4.6 mL, 35.9 mmol) at a rate to keep the reaction temperature below 35° C. The reaction mixture was stirred 2 h, then quenched with 5% potassium hydrogen sulfate solution and extracted four times with ether (100 mL). The ether extracts were combined, washed twice with water, once with brine, dried (MgSO$_4$) and evaporated to give an orange oil, 12.9 g. Purification of the crude product by flash chromatography on silica gel (12×30 cm column, 1:4 ethyl acetate/hexanes) gave the title compound as a light yellow oil, 8.15 g, 71% yield.

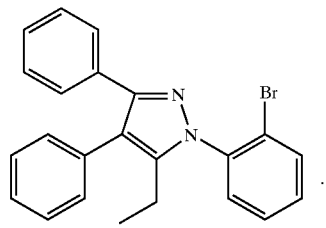

C

To a solution of Part B compound (2.33 g, 5.53 mmol) in DMF (15 mL) at room temperature under nitrogen was added sodium hydride (60% dispersion, 550 mg, 13.8 mmol)

in several portions over 1 min. The reaction warmed autogenously to 38° C. and was further heated to 50° C. for 20 min. The deep red reaction mixture was cooled in a water ice bath and quenched by adding 5% potassium hydrogen sulfate solution (10 mL) dropwise over 10 min. The mixture was then acidified with 1 N hydrochloric acid to bring the mixture to pH 2 and then extracted three times with ether (50 mL). The combined organic extracts were washed twice with water and once with brine, dried (MgSO₄) and evaporated. Purification of the crude product by flash chromatography on silica gel (5×25 cm column, 1:3 ethyl acetate/hexanes) gave the title compound as a light yellow amorphous solid, 1.63 g, 73% yield.

D

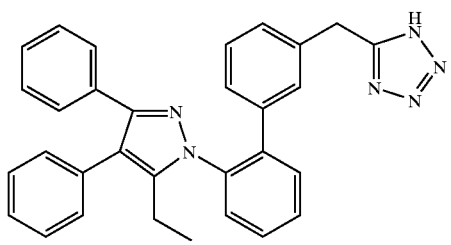

The title compound was generated by the procedure described in Example 8 starting with Compound C Example 73.

EXAMPLE 74

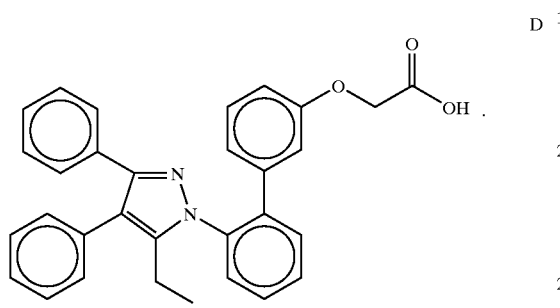

The title compound was generated by the procedure described in Example 23 starting with Example 73 Part C compound.

EXAMPLE 75

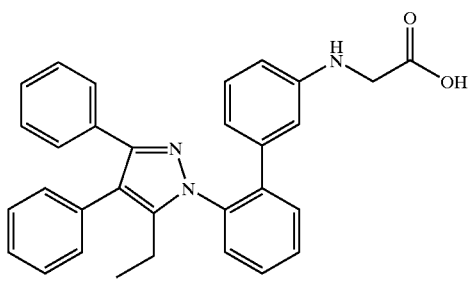

The title compound was generated by the procedure described in Example 3 starting with Example 73 Part C compound.

EXAMPLE 76

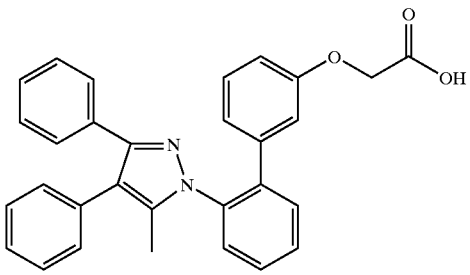

A

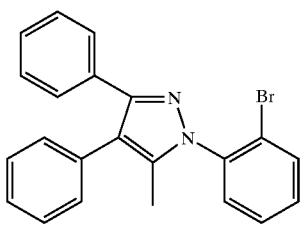

A stirred slurry of sodium hydride (60% dispersion, 1.64 g, 41.1 mmol) in N-methylpyrrolidone (NMP, 13 mL) at room temperature under nitrogen, was heated to 40° C. for 30 min. To this mixture was added Example 73 Part A compound (5.00 g, 13.7 mmol) in NMP (30 mL) in one portion. The reaction mixture was heated to 60° C. for 4 h and then cooled to room temperature. To this solution was added freshly distilled acetyl chloride (4.3 mL, 57.5 mmol) in NMP (5 mL) at a rate to keep the reaction temperature below 50° C. The reaction mixture was stirred 30 min, then quenched with water (300 mL), extracted twice with ether (100 mL) and twice with ethyl acetate. The organic extracts were combined, washed with saturated sodium bicarbonate solution, water, and brine, dried (MgSO₄) and evaporated. Purification of the crude product by flash chromatography on silica gel (5×20 cm column, 1:2 hexanes/CH₂Cl₂) gave the title compound as a white amorphous solid, 1.20 g, 23% yield.

B

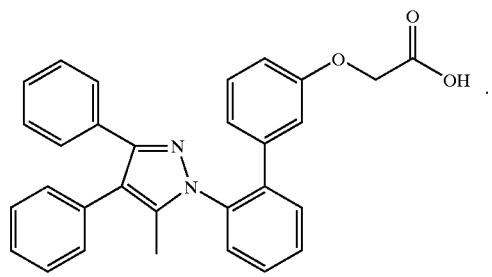

The title compound was generated by the procedure described in Example 8 starting with Part A compound.

EXAMPLE 77

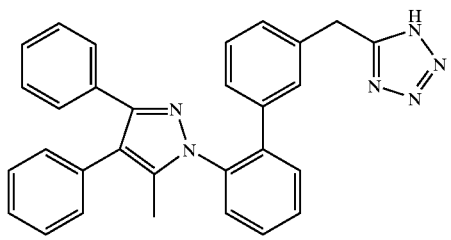

The title compound was generated by the procedure described in Example 23 starting with Example 76 Part A compound.

EXAMPLE 78

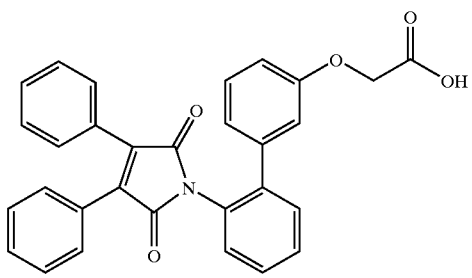

A

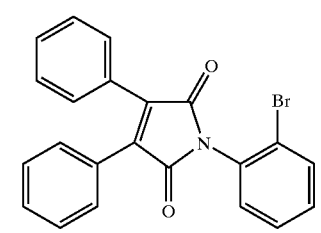

A mixture of 2-bromoaniline (2.18 g, 12.7 mmol) and 2,3-diphenylmaleic anhydride (3.17 g, (12.7 mmol) were stirred and heated under argon to 200° C. for 6 h. The mixture was cooled to room temperature, dissolved in $CH_2Cl_2$ (50 mL), dried ($MgSO_4$) and evaporated. Purification of the crude product by flash chromatography on silica gel (5×25 cm column, 2 L of 3:7 hexanes/$CH_2Cl_2$, then $CH_2Cl_2$) gave first 4-(2-bromoanilino)-2,3-diphenyl-4-hydroxybutyrolactone (2.16 g, 40% yield) as a yellow solid, mp 162–164° C. and then the title compound as a bright yellow solid, mp 178–180° C., 2.00 g, 39% yield.

B

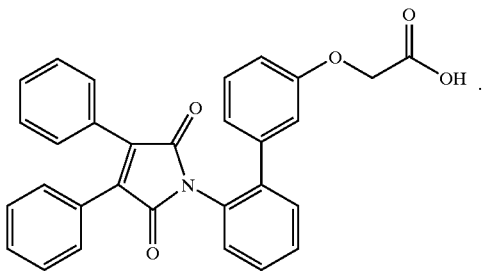

The title compound was generated by the procedure described in Example 8 starting with Example 78 Part A compound.

EXAMPLE 79

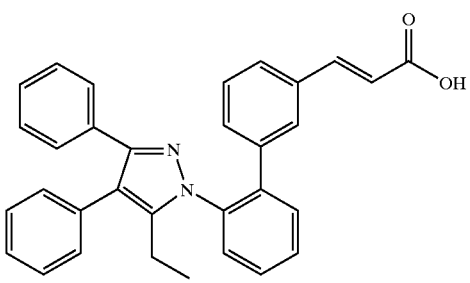

A

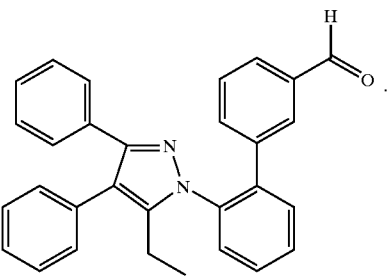

Analogous to the procedure described in Example 23 Part A, Example 73 Part C compound was used to prepare the title compound.

B

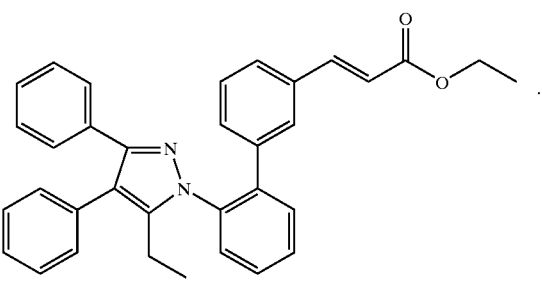

To a stirred solution of triethylphosphonoacetate (0.50 mL, 2.5 mmol) in THF (2.5 mL) under nitrogen at room temperature was added sodium hydride (60% dispersion, 100 mg, 2.5 mmol). After 10 min, the reaction was heated to 50° C. After an additional 20 min, a solution of Example 73 Part C compound (775 mg, 1.80 mmol) in THF (2 mL) was added as one portion. The reaction mixture was stirred for 2 h, cooled to room temperature and partitioned between ethyl acetate (50 mL) and 5% potassium hydrogen sulfate solution. The organic phase was dried (MgSO$_4$) and evaporated. Purification of the crude product by flash chromatography on silica gel (5×15 cm column, 1:49 ether/CH$_2$Cl$_2$) gave the title compound as a colorless oil, 785 mg, 88% yield.

C

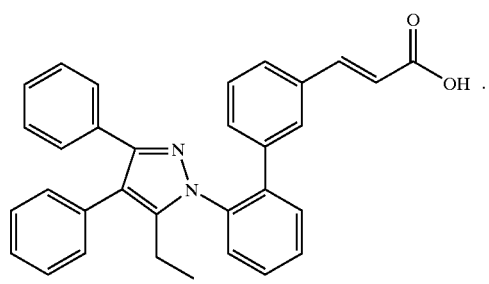

Analogous to the procedure described in Example 8 Part D, Part B compound was used to prepare the title compound.

EXAMPLE 80

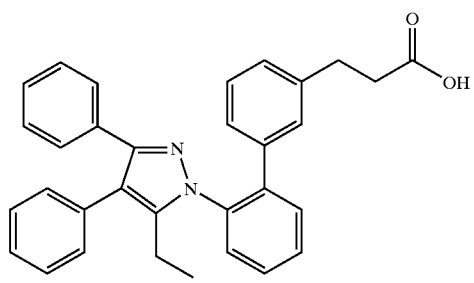

A

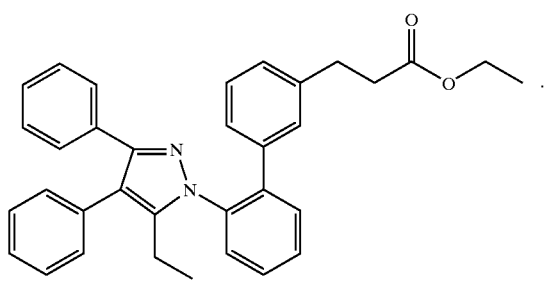

Hydrogenation of Example 79 Part B compound (765 mg, 1.53 mmol) was performed at room temperature and atmospheric pressure in ethanol (10 mL) using 10% palladium/charcoal (100 mg). After 4 h, the reaction mixture was purged with nitrogen, filtered (0.45 p nylon filter) and the filtrate evaporated to provide the title compound as a colorless oil, 770 mg, 100% yield.

B

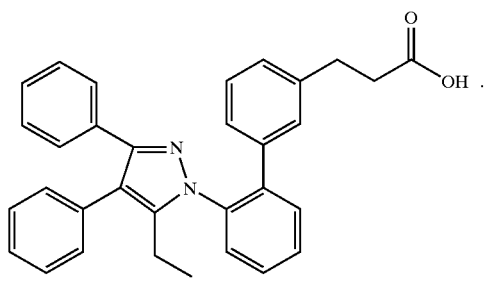

Analogous to the procedure described in Example 8 Part D, Part A compound was used to prepare the title compound.

EXAMPLE 81

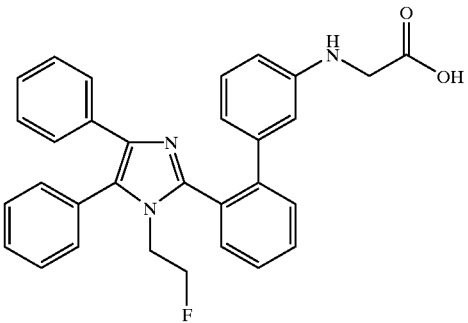

The title compound was generated in analogy to the procedures described in Examples 5, 9, and 11.

EXAMPLE 82

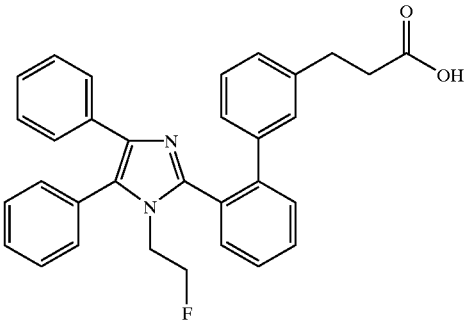

The title compound was generated in analogy to the procedures described in Examples 5 and 6.

EXAMPLE 83

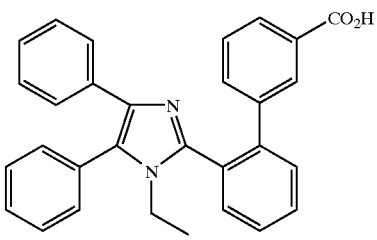

In analogy to the procedure described in Example 15, oxidation of Example 5 Part C compound afforded the title compound.

EXAMPLE 84

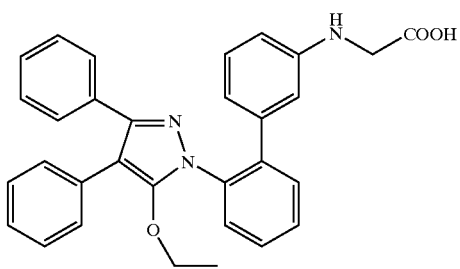

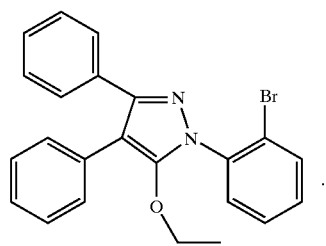

A

A mixture of Example 53 Part C compound (50 mg, 0.13 mmol), K$_2$CO$_3$ (26 mg, 0.19 mmol) and DMF (3 mL) was treated with ethyl iodide (60 mg, 0.38 mmol) and the mixture stirred for 18 h. The mixture was diluted with equal amounts of ethyl acetate and water. The organic fraction was washed with water, dried (MgSO$_4$) and concentrated. The remainder was purified by flash column chromatography with 20% ethyl acetate in hexane to give 48 mg (94%) of the title compound.

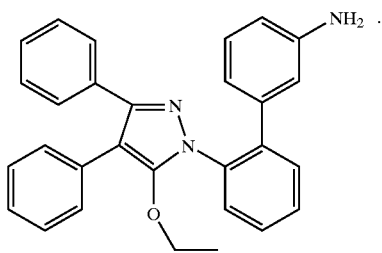

B

The experimental procedure as described in Example 53 Part E was followed for Suzuki coupling between the above Part A compound and 3-aminophenyl boronic acid to give the title compound (yield 91%).

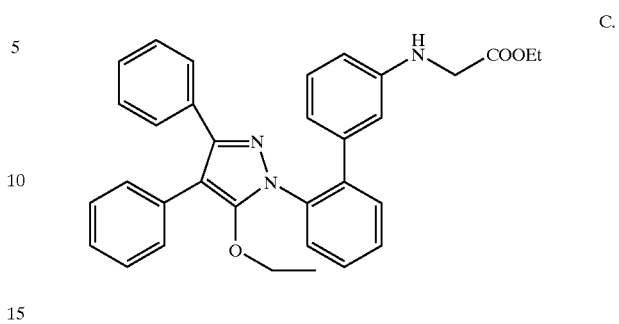

C.

The experimental procedure as set out in Example 53 Part F was followed employing the above Part B compound to give the title compound (yield 68%).

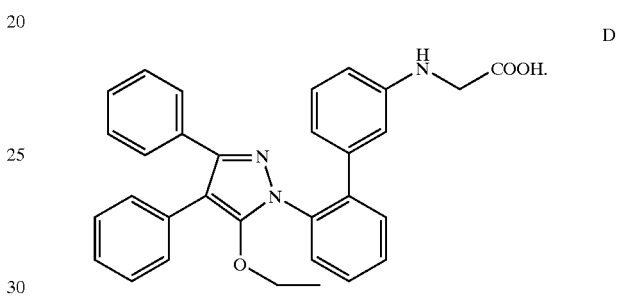

D

The experimental procedure as set out in Example 53 Part G was followed employing the above Part C compound to give the title compound (yield 92%).

The molecular weight and mass spectral analysis of each of the compounds prepared in Examples 1 to 84 are set out in the following tables.

TABLE 1

Linker variations in the oxazole series

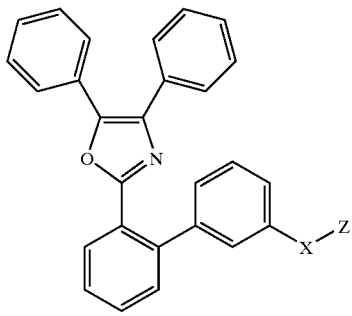

| Ex. | X | Z | MW | MS observed (M + H)$^+$ |
|---|---|---|---|---|
| 13 | —OCH(Me)— | CO$_2$H | 461.52 | 462 |
| 54 | —OCH$_2$— | tetrazole | 471.52 | 472 |
| 16 | —CH═CH— | CO$_2$H | 443.51 | 441 |
| 17 | —CH$_2$CH$_2$— | CO$_2$H | 445.52 | 446 |
| 3 | —NHCH$_2$— | CO$_2$H | 446.51 | 447 |
| 4 | —NHCO— | CO$_2$H | 460.49 | 461 |
| 18 | cyclopropyl | CO$_2$H | 457.53 | 458 |
| 25 | —N(Me)CH$_2$— | CO$_2$H | 460.54 | 461 |
| 15 | bond | CO$_2$H | 417.47 | 418 |
| 14 | —CH$_2$— | CO$_2$H | 431.5 | 432 |

TABLE 1-continued

Linker variations in the oxazole series

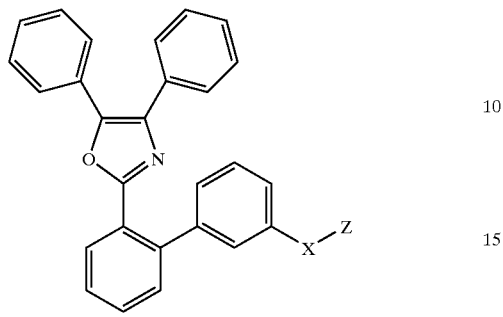

| Ex. | X | Z | MW | MS observed (M + H)+ |
|---|---|---|---|---|
| 2 | bond | tetrazole | 441.5 | 442 |
| 1 | —CH$_2$— | tetrazole | 455.52 | 456 |

TABLE 2

Ring substitution

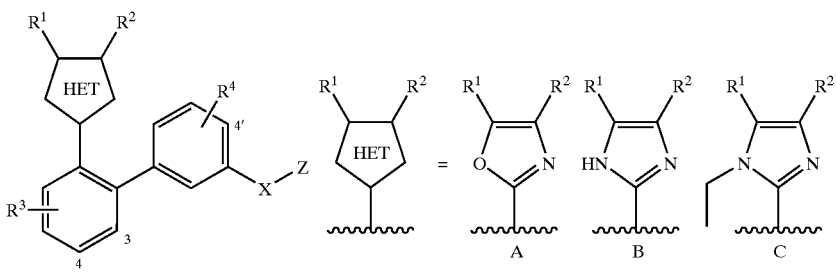

| Ex. | HET | R$^1$ | R$^2$ | R$^3$ | R$^4$ | X—A | MW | MS observed (M + H)+ |
|---|---|---|---|---|---|---|---|---|
| 26 | A | phenyl | phenyl | 3-Me | H | —NHCH$_2$CO$_2$H | 460.54 | 461 |
| 27 | A | phenyl | phenyl | H | 4'-Me | —NHCH$_2$CO$_2$H | 460.54 | 461 |
| 24 | A | phenyl | phenyl | 3-Me | H | —OCH$_2$CO$_2$H | 461.52 | 462 |
| 42 | A | phenyl | phenyl | 4-Cl | H | —NHCH$_2$CO$_2$H | 480.96 | 481 |
| 41 | A | 2-pyridyl | 2-pyridyl | H | H | —OCH$_2$CO$_2$H | 449.47 | 449 (M)+ |
| 44 | A | c-C$_6$H$_{11}$ | c-C$_6$H$_{11}$ | H | H | —OCH$_2$CO$_2$H | 459.59 | 460 |
| 40 | A | H | phenyl | H | H | —OCH$_2$CO$_2$H | 371.4 | 372 |
| 43 | A | c-C$_6$H$_{11}$ | phenyl | H | H | —OCH$_2$CO$_2$H | 453.54 | 454 |
| 46 | B | Ph | H | H | H | —OCH$_2$CO$_2$H | 370.41 | 371 |
| 55 | B | 4-F—Ph | 4-F—Ph | H | H | —OCH$_2$CO$_2$H | 482.49 | 483 |
| 56 | C | 4-F—Ph | 4-F—Ph | H | H | —OCH$_2$CO$_2$H | 510.54 | 511 |

TABLE 3

X-Z variation at the ortho position

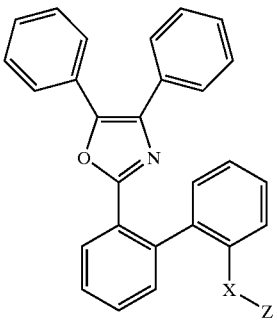

| Ex. | X | Z | MW | MS observed (M + H)+ |
|---|---|---|---|---|
| 31 | —CH=CH— | CO₂H | 443.51 | 444 |
| 32 | —CH₂CH₂— | CO₂H | 445.5 | 446 |
| 33 | bond | CO₂H | 417.47 | 418 |
| 12 | bond | tetrazole | 441.5 | 442 |

TABLE 4

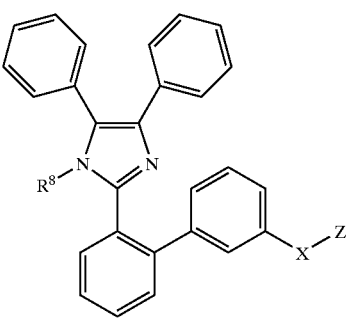

| Ex. | R⁸ | X | Z | MW | MS observed (M + H)+ |
|---|---|---|---|---|---|
| 36 | Me | —OCH₂— | CO₂H | 460.54 | 461 |
| 38 | H | —NHCH₂— | CO₂H | 445.53 | 446 |
| | | Imidazole based analogs | | | |
| 39 | Me | —NHCH₂— | CO₂H | 459.55 | 460 |
| 6 | Et | —NHCH₂— | CO₂H | 473.58 | 474 |
| 37 | Propyl | —NHCH₂— | CO₂H | 487.61 | 488 |
| 45 | —CH₂CH₂OH | —NHCH₂— | CO₂H | 489.58 | 490 |
| 9 | Et | —CH=CH— | CO₂H | 470.58 | 471 |
| 47 | —CH₂CH(Me)₂ | —NHCH₂— | CO₂H | 501.63 | 502 |
| 48 | Et | —NHCH₂— | tetrazole | 497.61 | 498 |
| 11 | Et | —CH₂CH₂— | CO₂H | 472.59 | 473 |
| 7 | Et | bond | tetrazole | 468.57 | 469 |
| 8 | Et | —OCH₂— | CO₂H | 474.56 | 475 |
| 51 | CH₂CO₂H | —NHCH₂— | CO₂H | 503.56 | 504 |
| 5 | Et | —CH₂— | tetrazole | 482.59 | 483 |
| 10 | Et | —CH₂— | CO₂H | 458.57 | 459 |
| 83 | Et | bond | CO₂H | 444.54 | 445 |
| 52 | Et | —OCH₂— | tetrazole | 498.59 | 499 |
| 34 | H | —OCH₂— | CO₂H | 446.51 | 447 |
| 35 | allyl | —OCH₂— | CO₂H | 486.58 | 487 |
| 57 | —CH₂OMe | —OCH₂— | CO₂H | 490.56 | 491 |
| 58 | —CH₂CH₂F | —OCH₂— | CO₂H | 492.55 | 493 |
| 81 | —CH₂CH₂F | —NHCH₂— | CO₂H | 491.57 | 492 |
| 82 | —CH₂CH₂F | —CH₂CH₂— | CO₂H | 490.58 | 491 |

TABLE 5

Furan, thiophene, and pyrrole derivatives

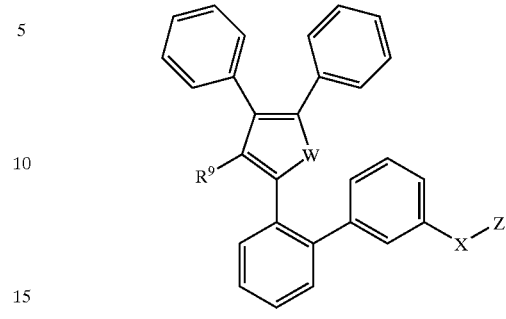

| Ex. | W | R⁹ | X | Z | MW | MS observed (M + H)+ |
|---|---|---|---|---|---|---|
| 23 | O | H | —CH₂— | tetrazole | 454.54 | 455 |
| 21 | N—Et | H | —NHCH₂— | tetrazole | 496.62 | 497 |
| 22 | S | H | —NHCH₂— | CO₂H | 461.59 | 462 |
| 20 | NH | H | —CH2— | tetrazole | 453.55 | 454 |
| 19 | O | H | —OCH₂— | tetrazole | 470.54 | 471 |
| 59 | O | H | —OCH₂— | CO₂H | 446.51 | 447 |
| 60 | N—Et | H | —CH₂— | tetrazole | 481.61 | 482 |
| 61 | O | Et | —OCH₂— | CO₂H | 474.56 | 475 |
| 62 | N—Et | H | —OCH₂— | tetrazole | 497.6 | 498 |
| 63 | N—Et | H | —OCH₂— | CO₂H | 473.58 | 474 |
| 64 | NH | H | —OCH₂— | CO₂H | 445.52 | 446 |
| 65 | O | Et | —CH₂— | tetrazole | 482.59 | 483 |
| 66 | O | —CH₂OH | —OCH₂— | CO₂H | 476.53 | 477 |
| 68 | O | —CH₂OEt | —OCH₂— | CO₂H | 504.59 | 505 |
| 69 | NH | Et | —OCH₂— | CO₂H | 473.58 | 474 |
| 70 | O | —CH(OH)Me | —OCH₂— | CO₂H | 490.56 | 491 |
| 67 | O | —CH₂OMe | —OCH₂— | CO₂H | 490.56 | 491 |
| 71 | NH | Et | —CH₂— | tetrazole | 481.61 | 482 |
| 72 | O | Et | —NHCH₂— | CO₂H | 473.58 | 474 |

TABLE 6

Pyrazole based analogs

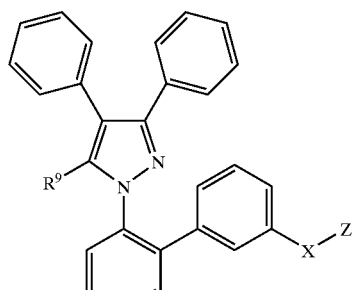

| Ex. | R⁹ | X | Z | MW | MS observed (M + H)+ |
|---|---|---|---|---|---|
| 73 | Et | —OCH₂— | CO₂H | 474.56 | 475 |
| 74 | Et | —CH₂— | tetrazole | 482.59 | 483 |
| 84 | OEt | —NHCH₂— | CO₂H | 489.58 | 490 |
| 75 | Et | —NHCH₂— | CO₂H | 473.58 | 474 |

TABLE 6-continued

Pyrazole based analogs

| Ex. | R⁹ | X | Z | MW | MS observed (M + H)⁺ |
|---|---|---|---|---|---|
| 76 | Me | —OCH$_2$— | CO$_2$H | 460.54 | 461 |
| 77 | Me | —CH$_2$— | tetrazole | 468.57 | 469 |
| 80 | Et | —CH$_2$CH$_2$— | CO$_2$H | 472.59 | 473 |
| 79 | Et | —CH=CH— | CO$_2$H | 470.58 | 471 |

TABLE 7

Various heterocyclic based analogs

| Ex. | Het | X-Z | MW | MS observed (M + H)⁺ |
|---|---|---|---|---|
| 49 | dioxolane-CH | —OCH$_2$CO$_2$H | 452.51 | 475 (M + Na)⁺ |
| 50 | dioxolane-CH | —OCH$_2$CO$_2$H | 452.51 | 475 (M + Na)⁺ |

TABLE 7-continued

Various heterocyclic based analogs

| Ex. | Het | X-Z | MW | MS observed (M + H)⁺ |
|---|---|---|---|---|
| 28 | pyrazole-CH$_2$OH | —OCH$_2$CO$_2$H | 476.54 | 477 |
| 30 | triazolone | —OCH$_2$CO$_2$H | 463.5 | 464 |
| 29 | triazolone | —NHCH$_2$CO$_2$H | 462.51 | 463 |
| 78 | maleimide | —OCH$_2$CO$_2$H | 475.51 | 476 |
| 53 | pyrazolone-N-Me | —NHCH$_2$CO$_2$H | 475.55 | 476 |

EXAMPLE 85

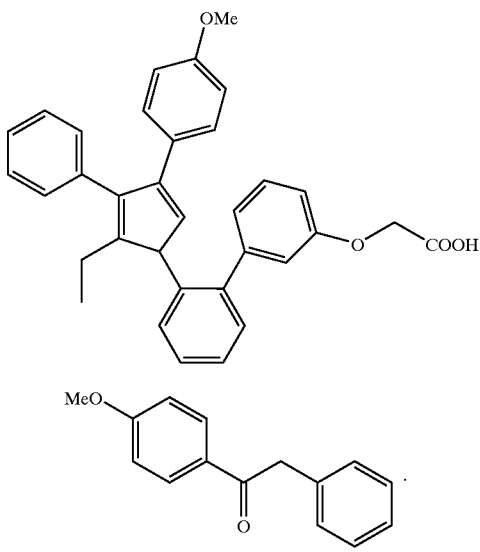

A

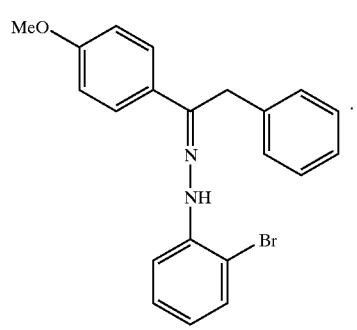

A mixture of 4-methoxy-benzonitrile (1.33 g, 10.0 mmol) and THF at −78° C. was treated with benzylmagnesium chloride in THF (5.1 mL, 10.2 mmol) over 5 min. The mixture was warmed to 45° C. for 2 h and cooled to ice bath temperature. The mixture was then treated slowly with 5 mL of 3N HCl and stirred for 2 h. Extraction with ethyl acetate (3×30 mL) drying (MgSO4) and concentrating gave a yellow oil. The oil was purified by flash column chromatography on silica gel with 4:6 hexane:dichloromethane to give 1.54 g (68%) of the title compound as a light yellow solid.

B

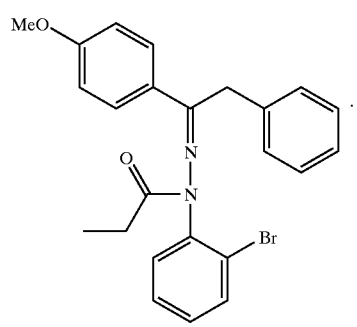

Analogous to the procedure described in Example 73 Part A, Part A compound and potassium acetate were used to prepare the title compound in 82% yield.

C

To a stirred solution of Part B compound (1.00 g, 2.53 mmol) in N-methylpyrrolidone (NMP, 2 mL), 4-dimethylamino-pyridine (DMAP, 0.31 g, 2.53 mmol), and N,N'-diisopropylethylamine (0.89 mL, 5.10 mmol) was added freshly distilled propionic anhydride (0.64 mL, 5.10 mmol) and the reaction heated to 90° C. for 2 h. The mixture was then treated every 24 h for 72 h with three additional amounts of DMAP (0.31 g, 2.53 mmol), N,N'-diisopropylethylamine (0.89 mL, 5.10 mmol) and propionic anhydride (0.64 mL, 5.10 mmol). After the final addition the mixture was stirred overnight at 90° C. and cooled to room temperature. The mixture was diluted with equal portions (50 mL) of 4N HCl and ethyl acetate and equilibrated. The organic fraction was washed with brine, saturated NHCO3 and brine, dried (MgSO4) and concentrated to give 1.49 g of the title compound as a crude brown oil.

D

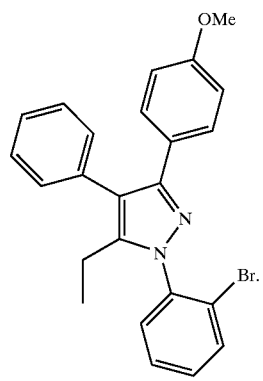

Analogous to the procedure described in Example 73 Part C, Part C compound was used to prepare the title compound in 50% yield.

E

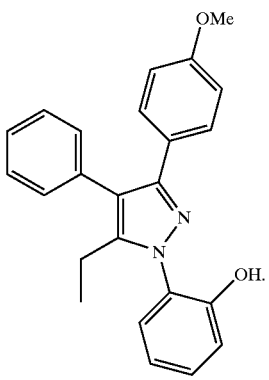

A solution of Part D compound (1.00 g, 2.3 mmol) and tris(dibenzylidene acetone)dipalladium(0) (0.13 g, 0.14 mmol) in a mixture of 1:3:1 THF:DME:water (10 mL) was treated with 3-hydroxyphenylboronic acid (0.45 g, 3.24 mmol) followed by the addition of aqueous Na2CO3 (6.4 mL, 1.5 M, 9.63 mmol). The mixture was heated to 50° C. for 2 h, cooled to room temperature and acidified to pH=3 with 2N HCl. The mixture was diluted with equal portions of ethyl acetate and brine (50 mL) and equilibrated. The organic fraction was washed with brine and 1N HCl, dried over Na$_2$SO$_4$ and concentrated to a solid. The solid was recrystallized from hot ethyl acetate to give 700 mg (68%) of the title compound.

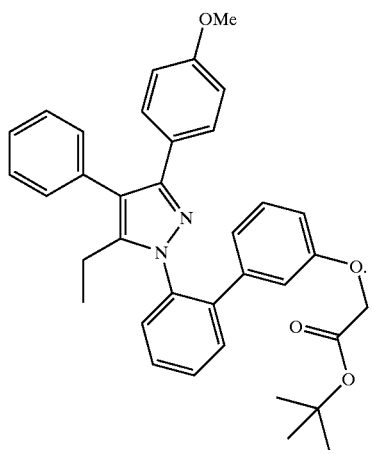

F

A slurry of Part E compound (0.70 g, 1.57 mmol) in DMF (6 mL) was treated with t-butyl bromoacetate (0.25 mL, 1.72 mmol) and cesium carbonate (0.51 g, 1.57 mmol) and stirred for 18 h. The reaction mixture was partitioned between ethyl acetate and water. The organic layer was washed with water, and brine, dried over MgSO$_4$ and concentrated. The crude product was purified by flash column chromatography on silica gel with 3:7 ethyl acetate/hexane to give the title compound as a white solid (0.70 g, 80%).

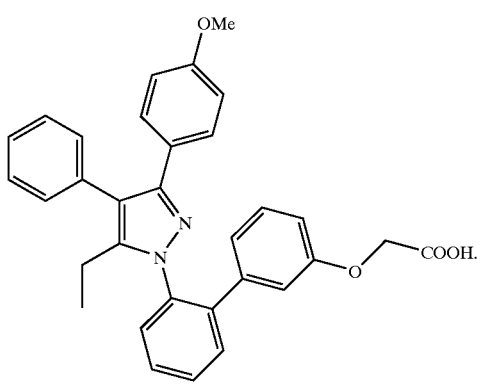

G

To a solution of Part F compound (0.33 g, 0.6 mmol) in dry dichloromethane (2 mL) at 0° C. was added boron tribromide in dichloromethane (1M, 2.7 mL, 2.7 mmol). The solution was stirred at 0° C. for 3 h and at room temperature overnight. The mixture was diluted with water followed by 1N HCl and extracted with ethyl acetate. The combined organic extracts were washed with brine, dried over MgSO4 and concentrated. The crude product was purified by preparative reverse phase chromatography to give the title compound as a white solid (0.05 g, 15%) and Example 86 part A compound (0.18 g, 55%). MS (title compound) [M+H]=505.

EXAMPLE 86

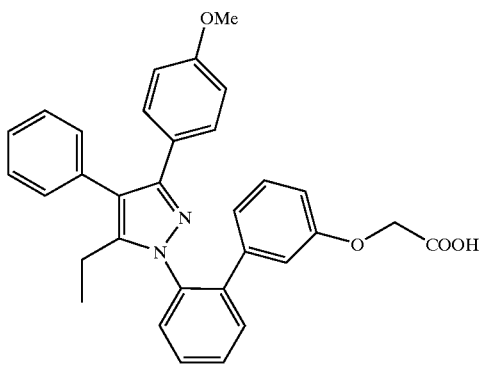

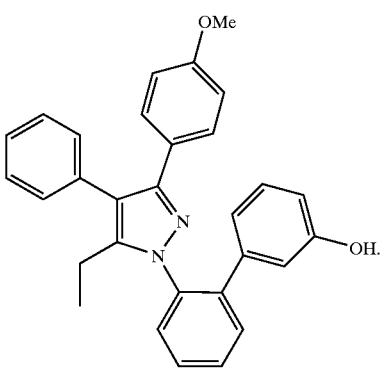

A

Following the procedure in Example 85 Part F afforded the title compound (yield 55%).

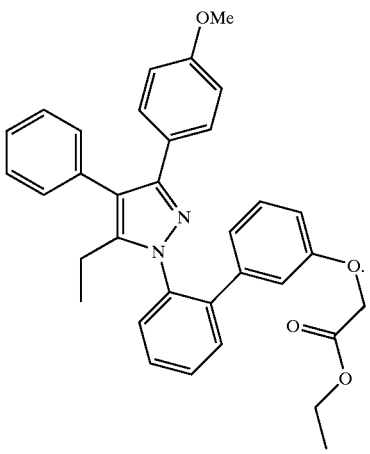

B

Following the procedure as in Example 28 Part G, alkylation of Part A compound with ethyl bromoacetate and cesium carbonate afforded the title compound (15%).

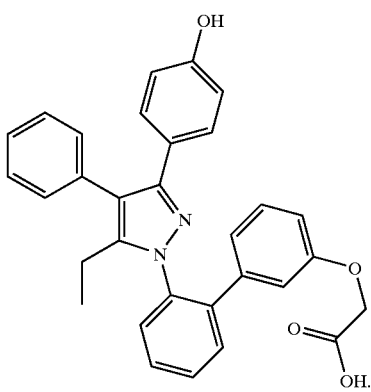

Following the experimental procedure as in Example 28 Part H, hydrolysis of Part B compound afforded the title compound as a white solid (85%). MS [M+H]=491.

What is claimed is:

1. A compound having the structure

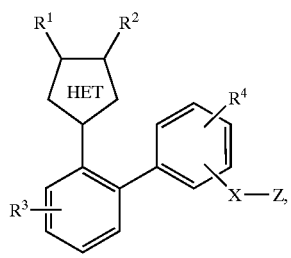

its stereoisomers, a pharmaceutically acceptable salt or prodrug ester thereof, wherein $R^1$ and $R^2$ are the same or different and are independently selected from, alkyl, cycloalkyl, cycloalkenyl, aryl, aralkyl, or;

$R^3$ is selected from hydrogen, halogen, alkyl, alkenyl, alkynyl, alkoxy, cycloalkyl, cycloalkylalkyl, cycloalkenyl, alkylcarbonyl, cycloalkenylalkyl, haloalkyl, polyhaloalkyl, cyano, nitro, hydroxy, amino, alkanoyl, alkylthio, alkylsulfonyl, alkoxycarbonyl, alkylaminocarbonyl, alkylcarbonylamino, alkylcarbonyloxy, alkylaminosulfonyl, alkylamino, dialkylamino, all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkoxycarbonylamino, alkylsulfonyl, aminosulfinyl, aniinosulfonyl, alkylsulfinyl, sulfonamido or sulfonyl;

$R^4$ is selected from hydrogen, halogen, alkyl, alkenyl, alkynyl, alkoxy, aryl, arylalkyl, arylalkenyl, arylalkynyl, cycloalkyl, cycloalkylalkyl, polycycloalkyl, polycycloalkylaikyl, cycloalkenyl, cycloalkynyl, alkylcarbonyl, arylcarbonyl, cycloheteroalkyl, cycloheteroalkylalkyl, cycloalkenylalkyl, polycycloalkenyl, polycycloalkenylalkyl, polycycloalkynyl, polycycloalkynylalkyl, haloalkyl, polyhaloalkyl, cyano, nitro, hydroxy, amino, alkanoyl, aroyl, alkylsulfonyl, arylsulfonyl, alkoxycarbonyl, aryloxycarbonyl, alkylaminocarbonyl, arylaminocarbonyl, alkylcarbonylamino, alkoxycarbonyloxy, alkylaminosulfonyl, arylaminosulfonyl, alkylamino, dialkylamino, all optionally substituted through available carbon atoms with 1, 2, 3, 4 or 5 groups selected from hydrogen, halo, haloalkyl, polyhaloalkyl, alkoxy, haloalkoxy, polyhaloalkoxy, alkoxycarbonyl, alkenyl, alkynyl, cycloalkyl, cycloalkylalkyl, aryl, arylalkyl, arylcycloalkyl, arylalkenyl, arylalkynyl, aryloxy, aryloxyalkyl, arylalkoxy, arylazo, hydroxy, hydroxyalkyl, nitro, cyano, amino, substituted amino, alkylamino, dialkylamino, thiol, alkylthio, arylthio, arylthioalkyl, alkylcarbonyl, arylcarbonyl, acyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, alkoxycarbonylamino, arylsulfinyl, arylsulfmylalkyl, arylsulfonyl, alkylsulfonyl, aminosulfinyl, aminosulfonyl, arylsulfonylamino, alkylsulfinyl, sulfonamido or sulfonyl;

X is a bond or a linker group selected from $(CH_2)_n$, $O(CH_2)_n$, $S(CH_2)_n$, cycloalkylene, $N(R^5)(CH_2)_n$, NHCO, or CH=CH where n=0–5 and $R^5$ is hydrogen, alkyl, or alkanoyl;

Z is $CO_2H$ or tetrazole of the formula

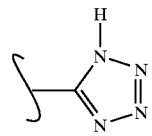

or its tautomer; and
the group

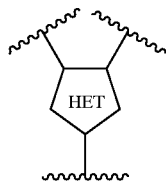

represents a heteroaryl group of the formula

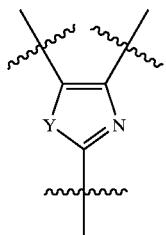

where Y is $NR^8$ or O;

which may further be optionally substituted with one or two groups, which may be the same or different and are independently selected from alkyl, alkenyl, hydroxyalkyl, keto, carboxyalkyl, carboxy, cycloalkyl, alkoxy, forrnyl, alkanoyl, alkoxyalkyl or alkoxycarbonyl, with the provisos that
(1) n≈o when Z is CO₂H and X is O(CH₂)ₙ, S(CH₂)ₙ or N(R⁵)(CH₂)ₙ); and
(2) when

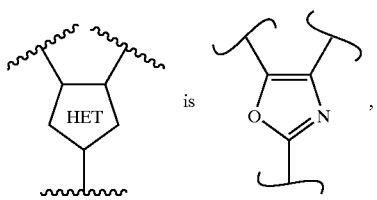

is then X—Z may not be O-lower alkylene-CO₂H or —O— lower alkylene-CO₂alkyl when R¹ and R² are both aryl or substituted aryl and R² and R⁴ are each hydrogen.

2. The compound as defined in claim 1 wherein

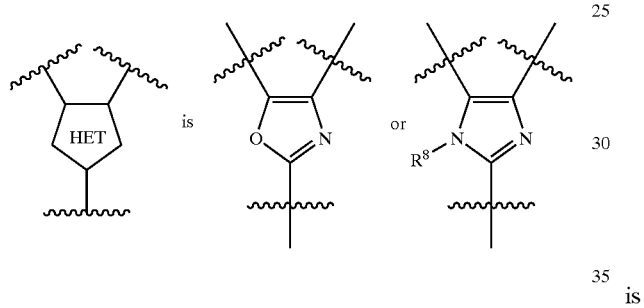

where R⁸ is selected from H, alkyl, haloalkyl, hydroxyalkyl, alkoxyalkyl, alkenyl, and R⁹ is selected from H, alkyl, alkenyl, formyl, CO₂(lower alkyl), hydroxyalkyl, alkoxyalkyl, CO(alkyl), carboxyalkyl, haloalkyl, alkenyl or cycloalkyl.

3. The compound as defined in claim 1 wherein R¹ and R² are the same or different and are independently selected from aryl, cycloalkyl, or hydrogen.

4. The compound as defined in claim 1 wherein R¹ and R² are the same or different and are independently selected from phenyl, cyclohexyl, or hydrogen.

5. The compound as defined in claim 1 wherein R³ and R⁴ are the same or different and are independently selected from hydrogen, alkyl or halogen.

6. The compound as defined in claim 1 wherein —X—Z is

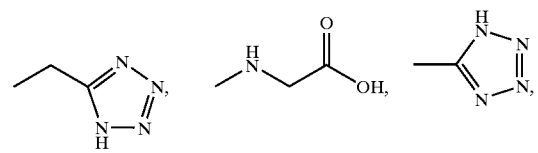

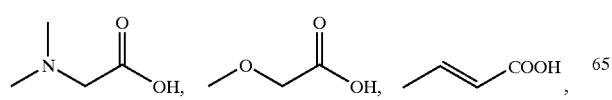

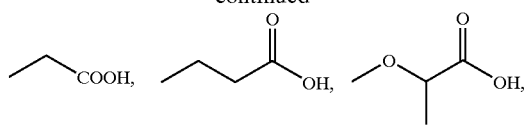

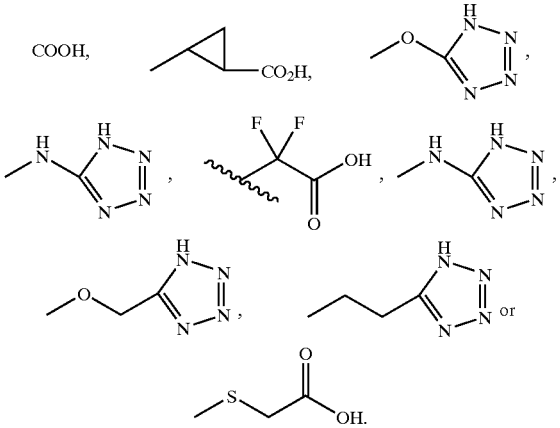

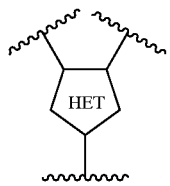

7. The compound as defined in claim 1 wherein

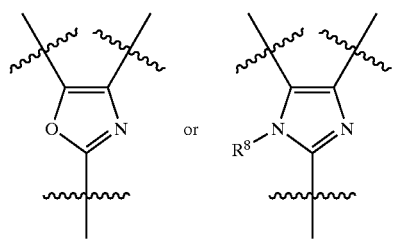

is

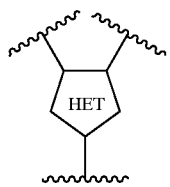

where R⁸ is H, lower alkyl, fluoroalkyl, or alkoxyalkyl, and R⁹ is H, lower alkyl, fluoroalkyl, alkoxy or hydroxyalkyl;

R¹ and R² are the same or different and are independently selected from phenyl or substituted phenyl;

R³ and R⁴ are the same or different are independently selected from H, halo, alkyl or alkoxy;

X is OCH₂, NHCH₂, CH₂ or CH₂CH₂; and

Z is CO₂H or tetrazole.

8. The compound as defined in claim 1 where is
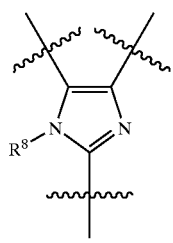
where $R^8$ is H, lower alkyl or fluoroalkyl, and $R^9$ is H, lower alkyl, fluoroalkyl, or alkoxy;
$R^1$ and $R^2$ are each phenyl;
$R^3$ and $R^4$ are each H;
X is $OCH_2$, $CH_2$ or $NHCH_2$; and
Z is $CO_2H$ or tetrazole.
9. The compound as defined in claim 1 wherein
$R^1$ is 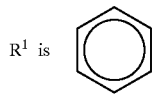   $R^2$ is 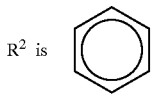
$R^3$ is H
$R^4$ is H and —X—Z is
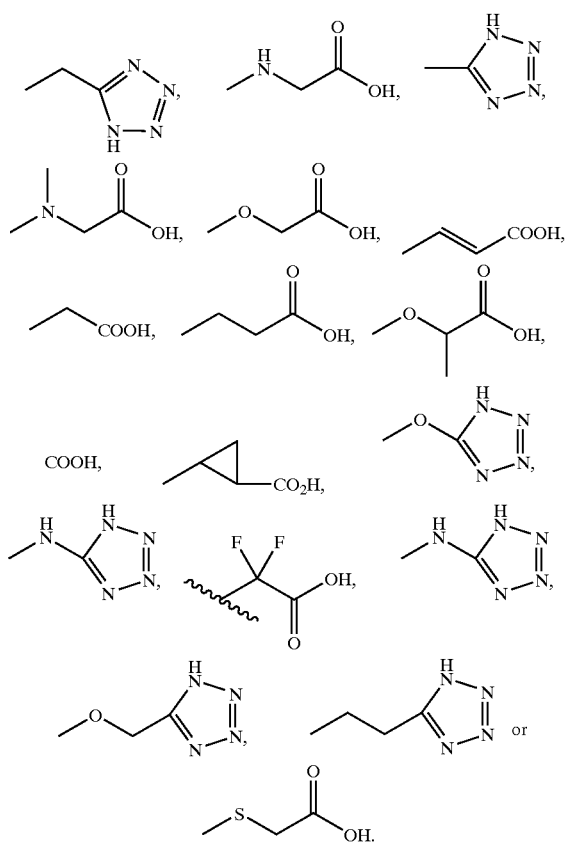
10. The compound as defined in claim 1 which is
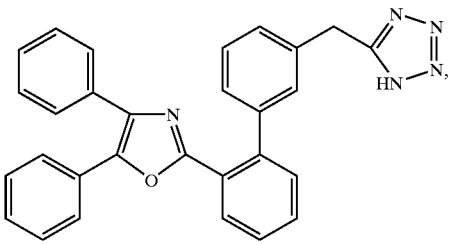
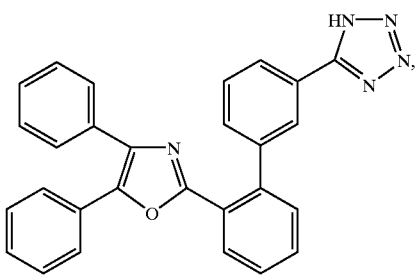
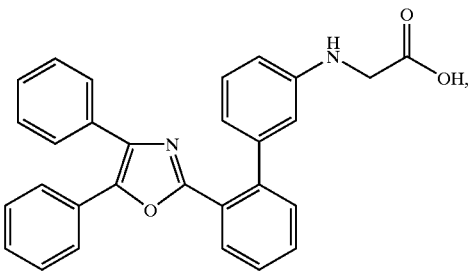
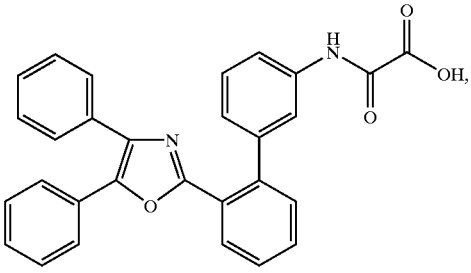
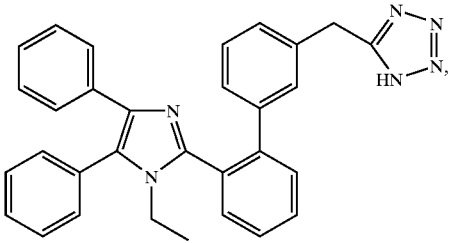
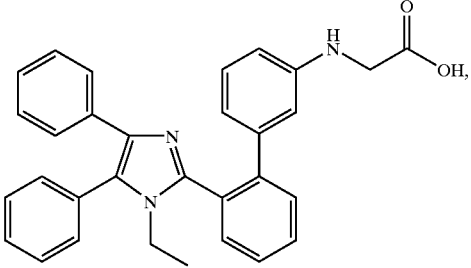

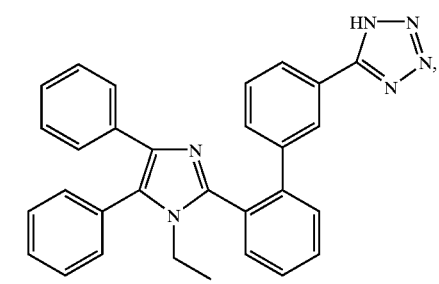
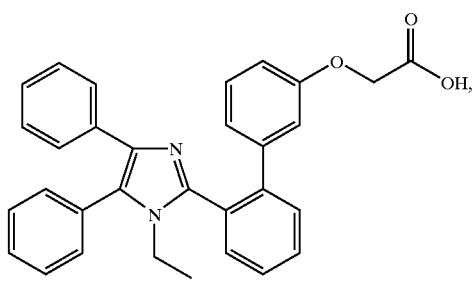
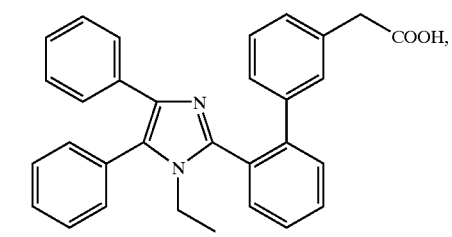
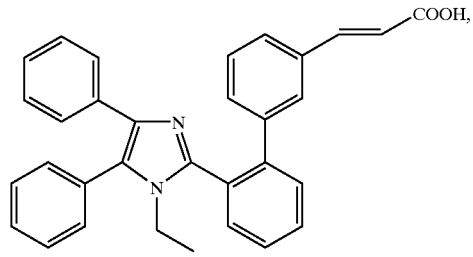
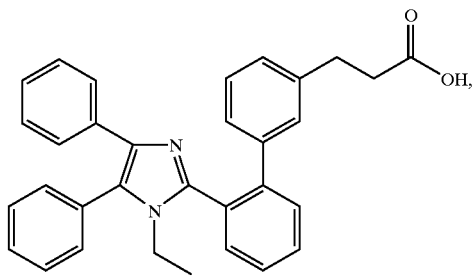
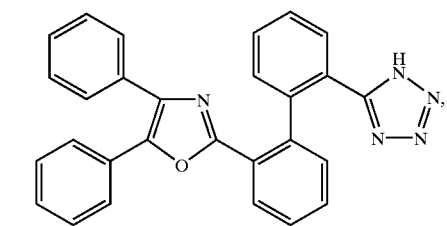
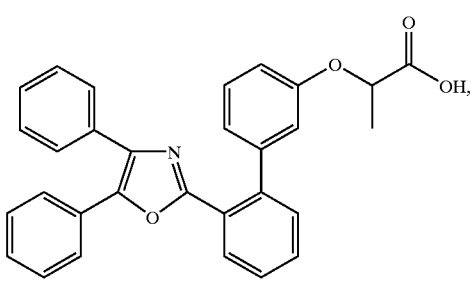
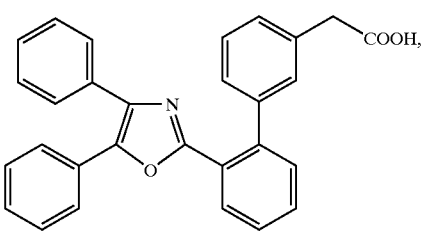
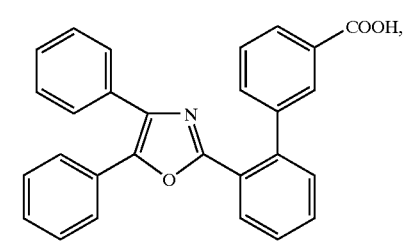
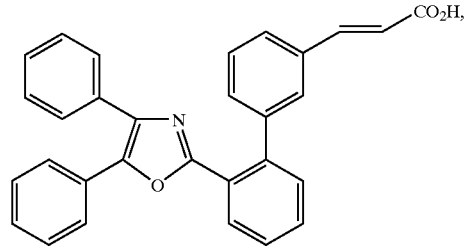
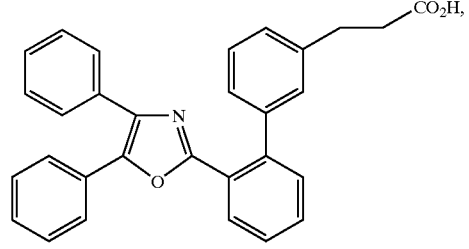
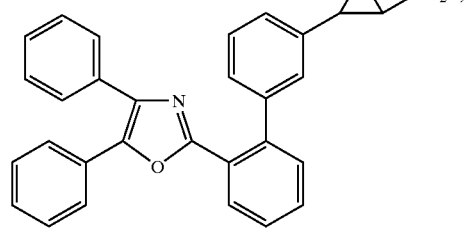

141
-continued

142
-continued

-continued
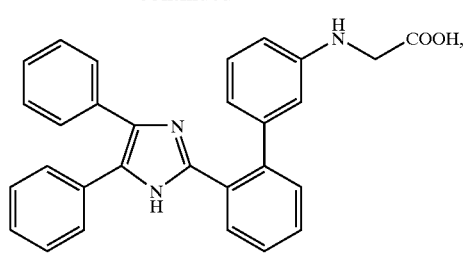
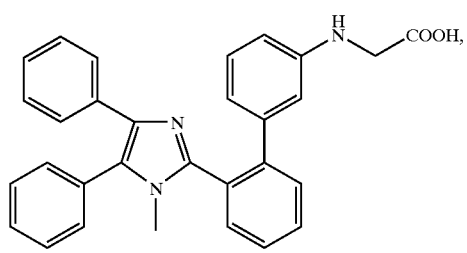
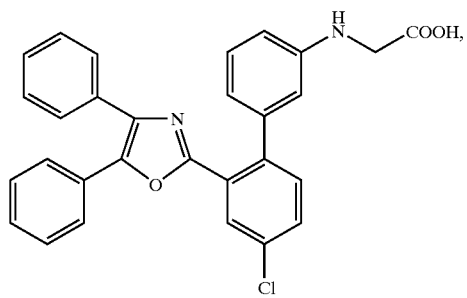
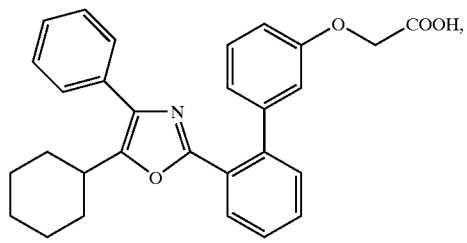
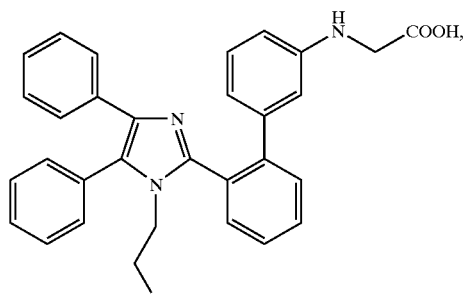
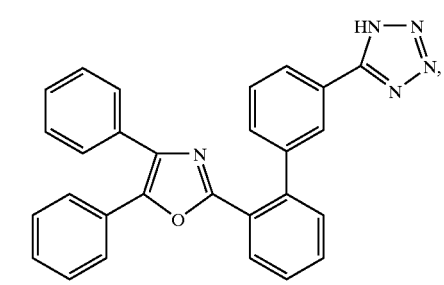
-continued
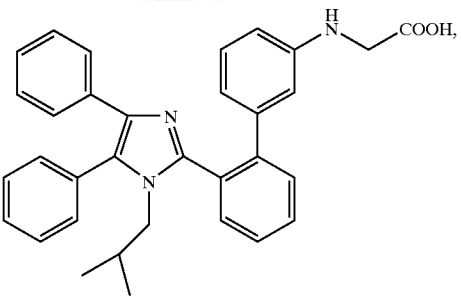
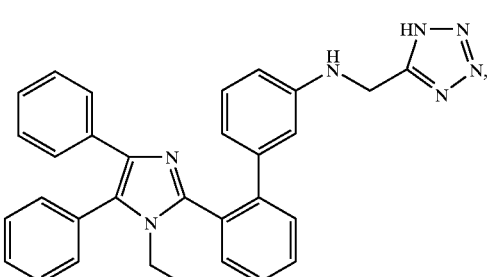
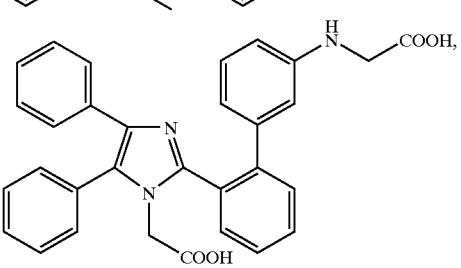
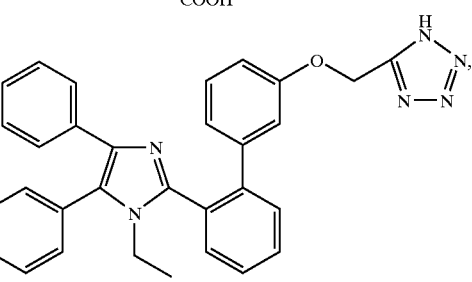
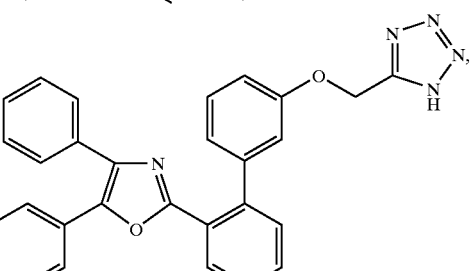
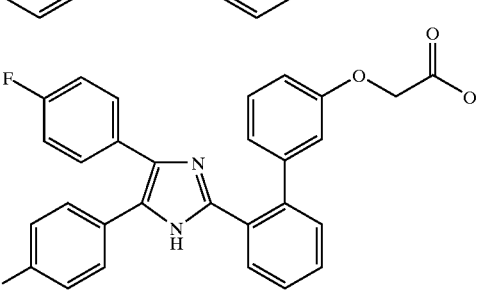

-continued
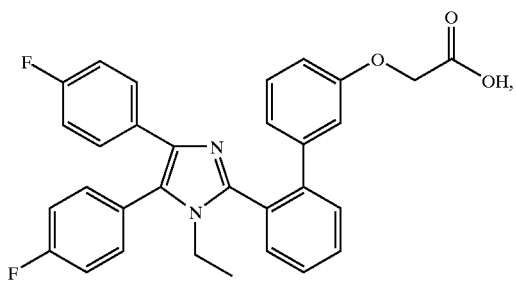
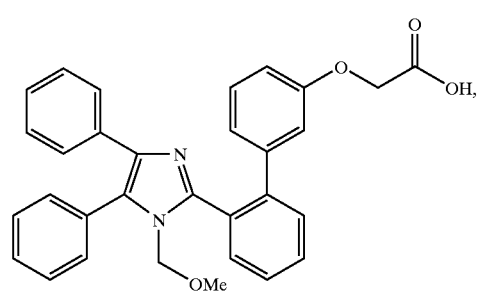
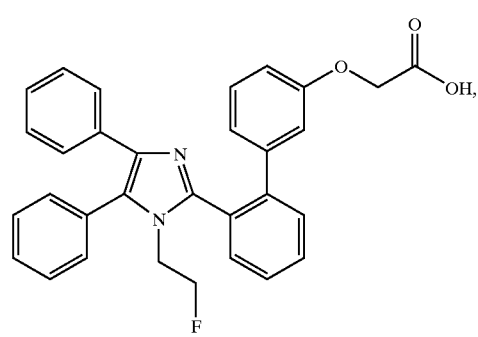
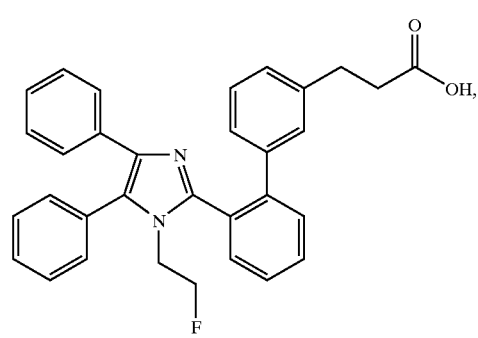
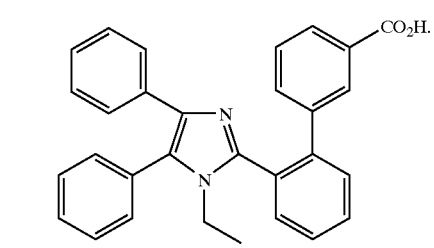
11. The compound as defined in claim 1 which is
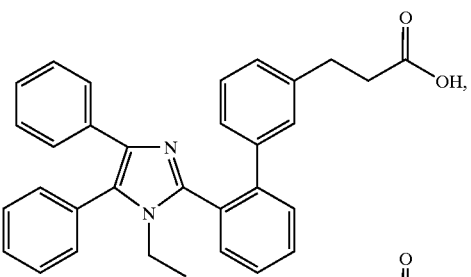
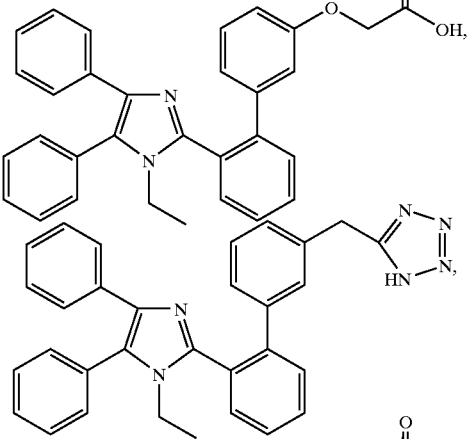
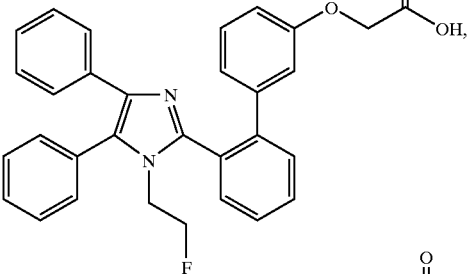
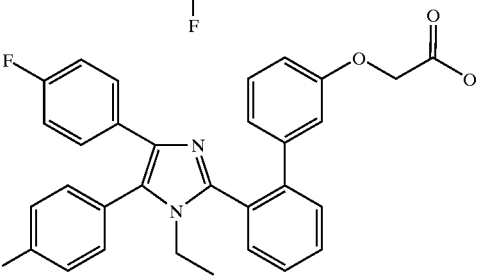
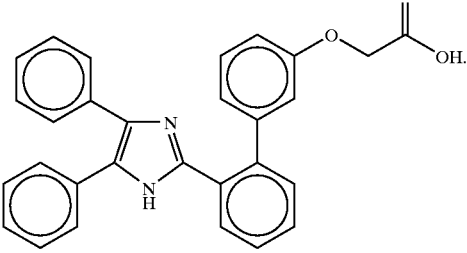
12. A pharmaceutical composition comprising a compound as defined in claim 1 and a pharmaceutically acceptable carrier therefor.
* * * * *

UNITED STATES PATENT AND TRADEMARK OFFICE
CERTIFICATE OF CORRECTION

PATENT NO. : 6,927,227 B2
DATED : August 9, 2005
INVENTOR(S) : Robl et al.

It is certified that error appears in the above-identified patent and that said Letters Patent is hereby corrected as shown below:

Column 133,
Lines 39-40, "independently selected from, alkyl, cycloalkyl, cycloalkenyl, aryl, aralkyl, or;" should read -- independently selected from cycloalkyl, cycloalkenyl, aryl, or aralkyl; --.
Line 60, "aniinosulfonyl, alkylsulfinyl, sulfonamido or sulfonyl" should read
-- aminosulfonyl, alkylsulfinyl, sulfonamido or sulfonyl --.
Line 64, "polycycloalkyl, polycycloalkylaikyl, cycloalkenyl," should read
-- polycycloalkyl, polycycloalkylalkyl, cycloalkenyl, --.

Column 134,
Line 10, "with 1, 2, 3, 4 or 5 groups selected from hydrogen, halo," should read
-- with 1, 2, 3, 4 or 5 groups selected from hydrogen, halo, alkyl --.
Line 24, "arylsulfmyalkyl, arylsulfonyl, alkylsulfonyl," should read -- arylsulfinylalkyl, arylsulfonyl, alkylsulfonyl, --.

Column 135,
Line 5, "(1) n≈0 when Z is CO$_2$H and X is O(CH$_2$)$_n$, S(CH$_2$)$_n$ or" should read
-- (1) n≠0 when Z is CO$_2$H and X is O(CH$_2$)$_n$, S(CH$_2$)$_n$ or --.

Column 136,
Line 15,

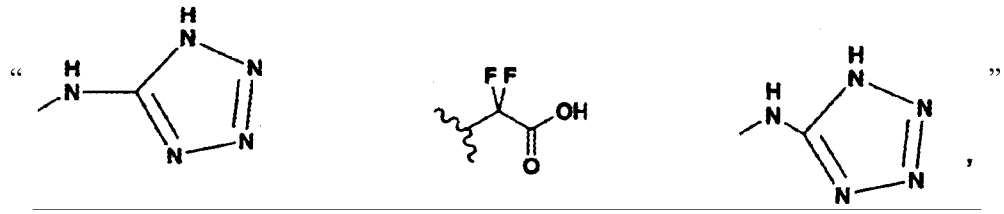

should read

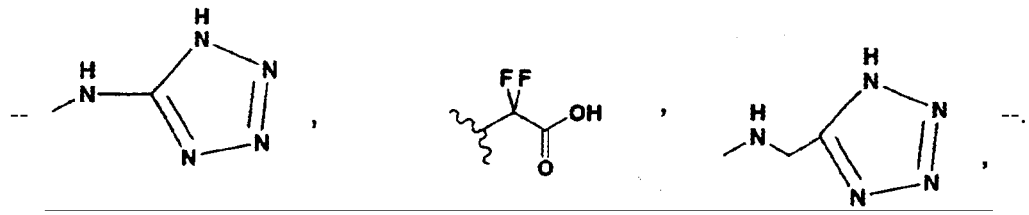

UNITED STATES PATENT AND TRADEMARK OFFICE
CERTIFICATE OF CORRECTION

PATENT NO. : 6,927,227 B2
DATED : August 9, 2005
INVENTOR(S) : Robl et al.

It is certified that error appears in the above-identified patent and that said Letters Patent is hereby corrected as shown below:

Column 137,
Line 55,

" 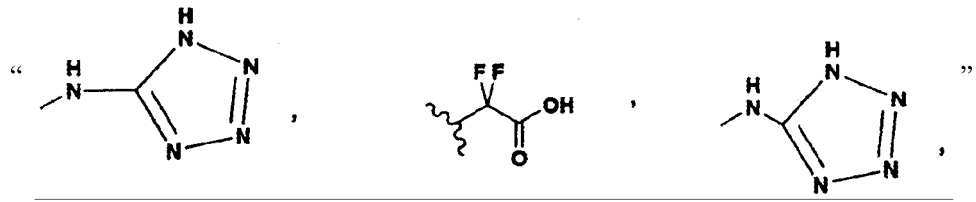 "

should read

-- 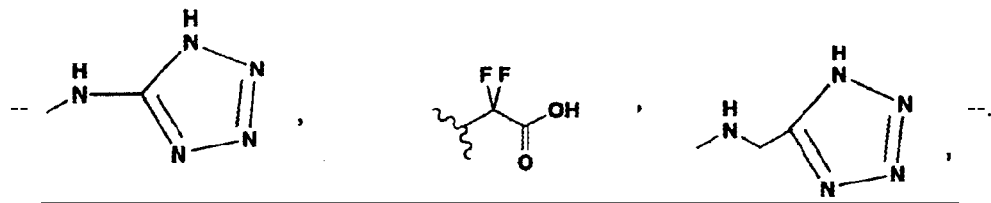 --.

Signed and Sealed this

Seventh Day of February, 2006

JON W. DUDAS
*Director of the United States Patent and Trademark Office*